(12) United States Patent
Scheer et al.

(10) Patent No.: US 8,809,619 B2
(45) Date of Patent: Aug. 19, 2014

(54) KNOCKOUT MICE FOR A P450 GENE CLUSTER

(75) Inventors: Nico Scheer, Cologne (DE); Charles Roland Wolf, Dundee (GB)

(73) Assignee: ITI Scotland Limited, Glasgow (GB)

( * ) Notice: Subject to any disclaimer, the term of this patent is extended or adjusted under 35 U.S.C. 154(b) by 313 days.

(21) Appl. No.: 12/679,570

(22) PCT Filed: Oct. 17, 2008

(86) PCT No.: PCT/GB2008/003531
§ 371 (c)(1),
(2), (4) Date: Sep. 9, 2010

(87) PCT Pub. No.: WO2009/050484
PCT Pub. Date: Apr. 23, 2009

(65) Prior Publication Data
US 2010/0333222 A1 Dec. 30, 2010

(30) Foreign Application Priority Data
Oct. 19, 2007 (GB) .................................. 0720552.9

(51) Int. Cl.
*A01K 67/027* (2006.01)

(52) U.S. Cl.
USPC .................................. 800/18; 800/3; 435/325

(58) Field of Classification Search
USPC ............... 800/18, 21, 8, 3; 435/325
See application file for complete search history.

(56) References Cited

FOREIGN PATENT DOCUMENTS

| EP | 1 206 906 | * | 5/2002 |
| EP | 1 362 911 | | 11/2003 |
| WO | WO 2006/064197 | * | 6/2006 |

OTHER PUBLICATIONS

Guengerich (Annu. Rev. Pharmacol. Toxicol., 1999, vol. 39, p. 1-17).*
Van Herwaarden (J. Clin. Invest. Nov. 2007, vol. 117, No. 17, p. 3583-3592).*
Waterschoot (Mol. Pharmac. 2008, vol. 73, p. 1029-1036, printed online Dec. 21, 2007).*
Waterschoot (FASEB J. 2009, vol. 23, p. 224-231).*
Lynch (Am. Family Physician, Aug. 1, 2007, vol. 76, No. 3, p. 391-396).*
European Patent Office, Examination Report, Patent Application No. EP 08806623.8, Mar. 1, 2011, fourteen pages.
Gonzalez, F.J., "Role of Gene Knockout and Transgenic Mice in the Study of Xenobiotic Metabolism," *Drug Metabolism Reviews*, Nov. 2003, pp. 319-335, vol. 35, No. 4.
Henderson, C. et al., "Inactivation of the Hepatic Cytochrome P450 System by Conditional Deletion of Hepatic Cytochrome P450 Reductase," *The Journal of Biological Chemistry*, Apr. 11, 2003, pp. 13480-13486, vol. 278, No. 15.
Henderson, C. et al., "The Hepatic Cytochrome P450 Reductase Null Mouse as a Tool to Identify a Successful Candidate Entity," *Toxicology Letters*, 2006, pp. 111-117, vol. 162.
Henderson, C. et al., "Transgenic Analysis of Drug-Metabolizing Enzymes: Preclinical Drug Development and Toxicology," *Molecular Interventions*, Sep. 2003, pp. 331-344, vol. 3, Issue 6.
Nelson, D. et al., "Comparison of Cytochrome P450 (CYP) Genes from the Mouse and Human Genomes, Including Nomenclature Recommendations for Genes, Pseudogenes and Alternative-splice Variant," *Pharmacogenetics and Genomics*, Jan. 2004, pp. 1-18, vol. 14, No. 1.
PCT International Search Report, PCT Application No. PCT/GB2008/003531, Mar. 9, 2009, four pages.
PCT International Written Opinion, PCT Application No. PCT/GB2008/003531, Apr. 19, 2010, ten pages.
Stanley, L. et al., "PXR and CAR: Nuclear Receptors Which Play a Pivotal Role in Drug Disposition and Chemical Toxicity," *Drug Metabolism Reviews*, Jan. 1, 2006, pp. 515-597, vol. 38, No. 3.
Van Herwaarden, A. et al., "Knockout of Cytochrome P450 3A Yields New Mouse Models for Undertanding Xenobiotic Metabolism," *The Journal of Clinical Investigation*, Nov. 1, 2007, pp. 3583-3592, vol. 117, No. 11.
Wolf, C. et al., "The Application of Transgenic and Humanised Nuclear Receptor Models in Drug Development," *Drug Metabolism Reviews, 9th European Meeting of the International Society for the Study of Xenobiotics (ISSX)*, Jan. 1, 2006, pp. 7-8, vol. 38, No. Suppl. 1.
Zaher, H. et al., "Protection Against Acetaminophen Toxicity in CYP1A2 and CYP2E1 Double Null Mice," *Toxicology and Applied Pharmacology*, 1998, pp. 193-199, vol. 152.

* cited by examiner

*Primary Examiner* — Michael C. Wilson
(74) *Attorney, Agent, or Firm* — Fenwick & West LLP

(57) ABSTRACT

The invention relates to the generation of mouse models of drug metabolism in which clusters of genes that are involved in drug metabolism have been knocked out. The development of new drugs and chemicals for therapeutic use or for other purposes is extremely complex. Of particular importance is the understanding of how these chemical agents are handled in the body, whether they have appropriate pharmacokinetics and whether, as a consequence of metabolism, any safety issues arise. Many of the proteins that are involved in the metabolism, disposition and elimination of drugs are members of multigene families that exhibit very marked species differences in gene number, function and regulation. For these reasons, experiments carried out in laboratory animals to establish routes of metabolism or toxicity can be severely compromised and, as a consequence, do not faithfully represent the human situation. One example of this complexity is reflected in the mammalian cytochrome P450 system, where the sizes of multigene families of proteins which carry out particular metabolic functions vary enormously between species.

3 Claims, 37 Drawing Sheets

PCR No. 1398

(Detects the deletion of the mouse Cyp3a Cluster)

Primers used to detect Cyp3a Cluster deletion:
1398_1: oC2cCdf1 GACATTGACATCCACTTGCC
1398_2: oC3a11dr2 GGGAGGGAAACTTGGAGG
Expected fragment: 319bp

PCR control primers:
1260_1: GAGACTCTGGCTACTCATCC
1260_2: CCTTCAGCAAGAGCTGGGAC
Expected fragment: 585bp IDs: 1=Marker, 2=219678, 3=219679, 4=219680, 5=219681, 6=219682, 7= H2O, 8=pos. Control, 9=B6 Wt DNA

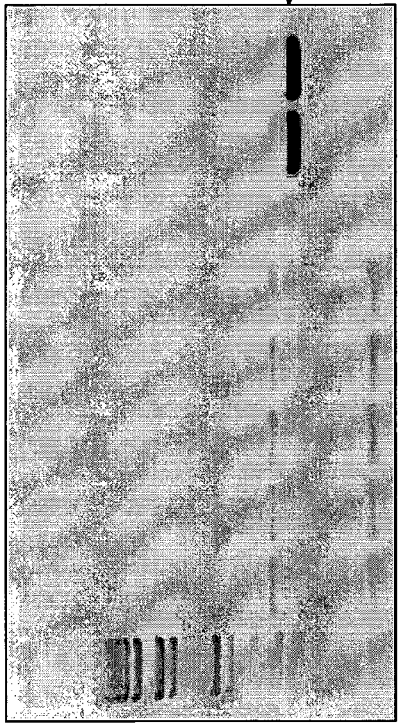
Fig.1b (contd.)

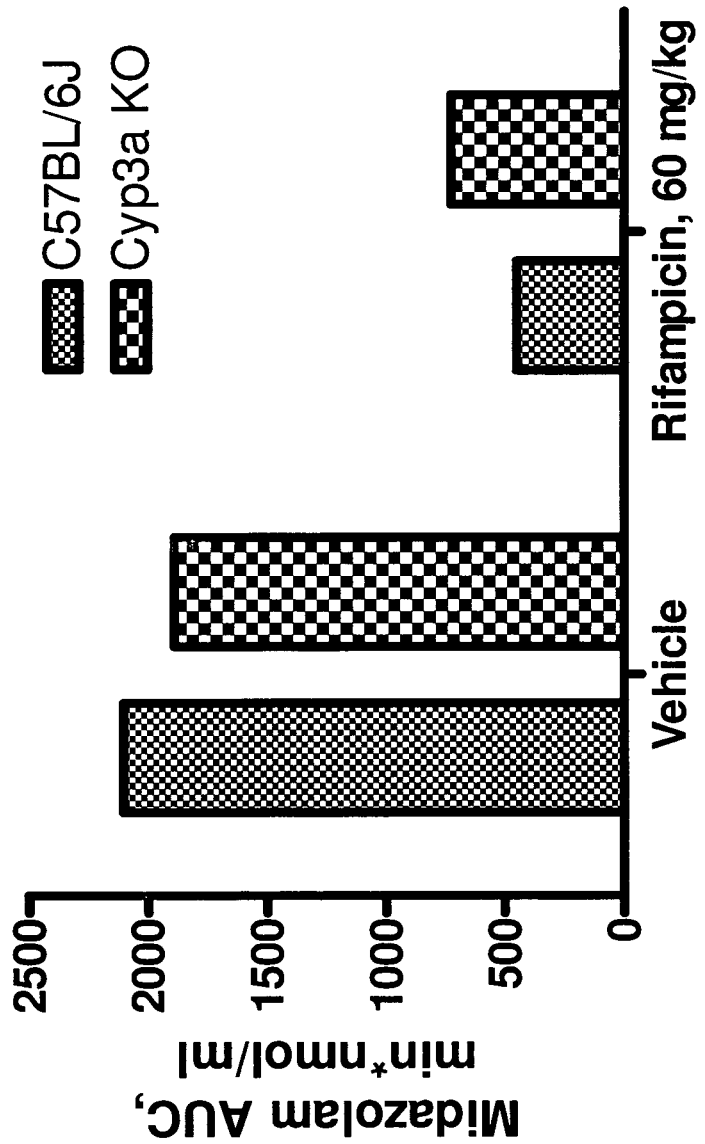

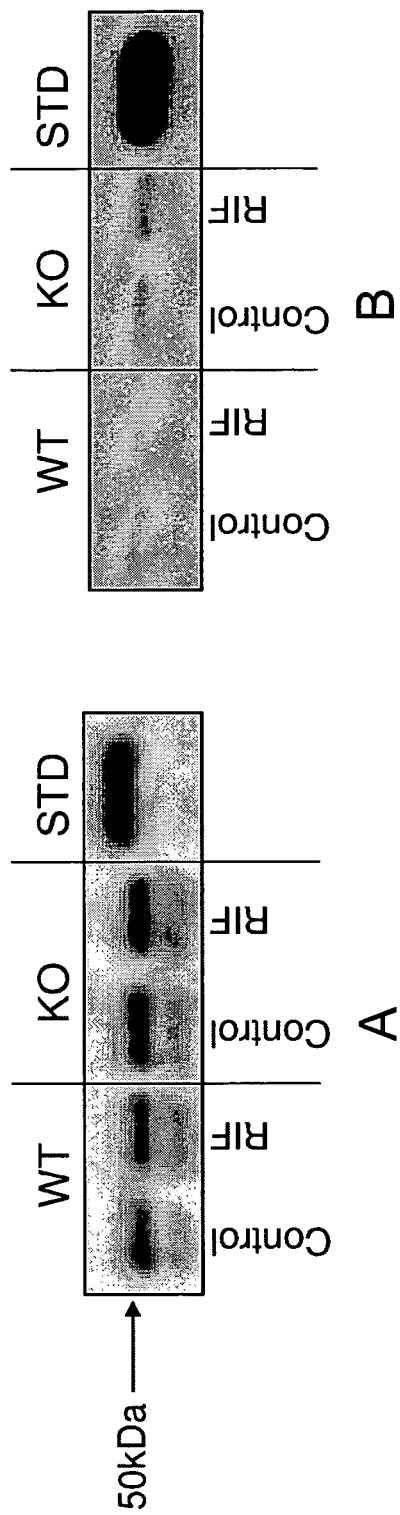
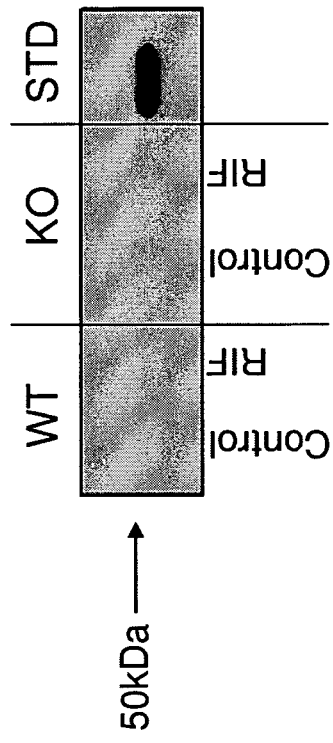
Fig.1o
Fig.1p

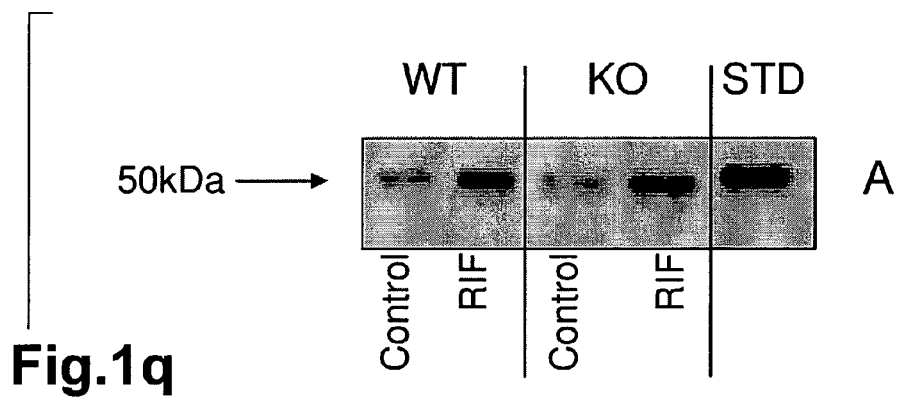
Fig.1q
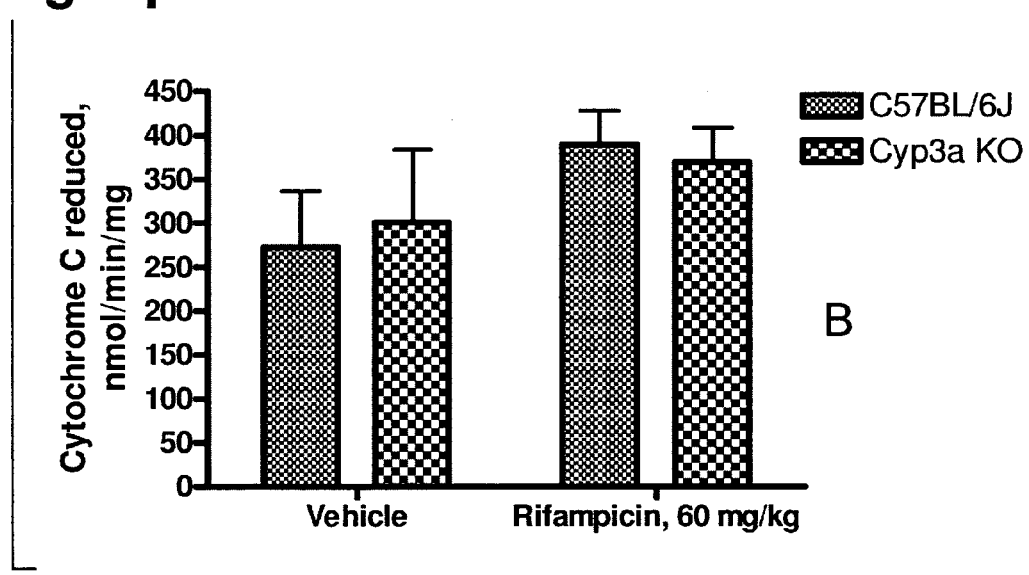
Fig.1r
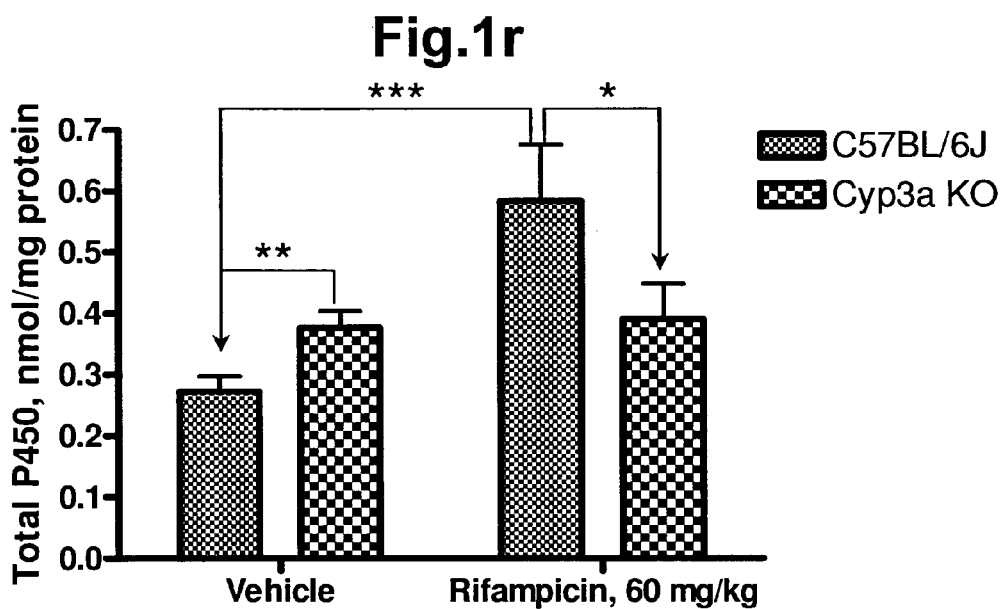

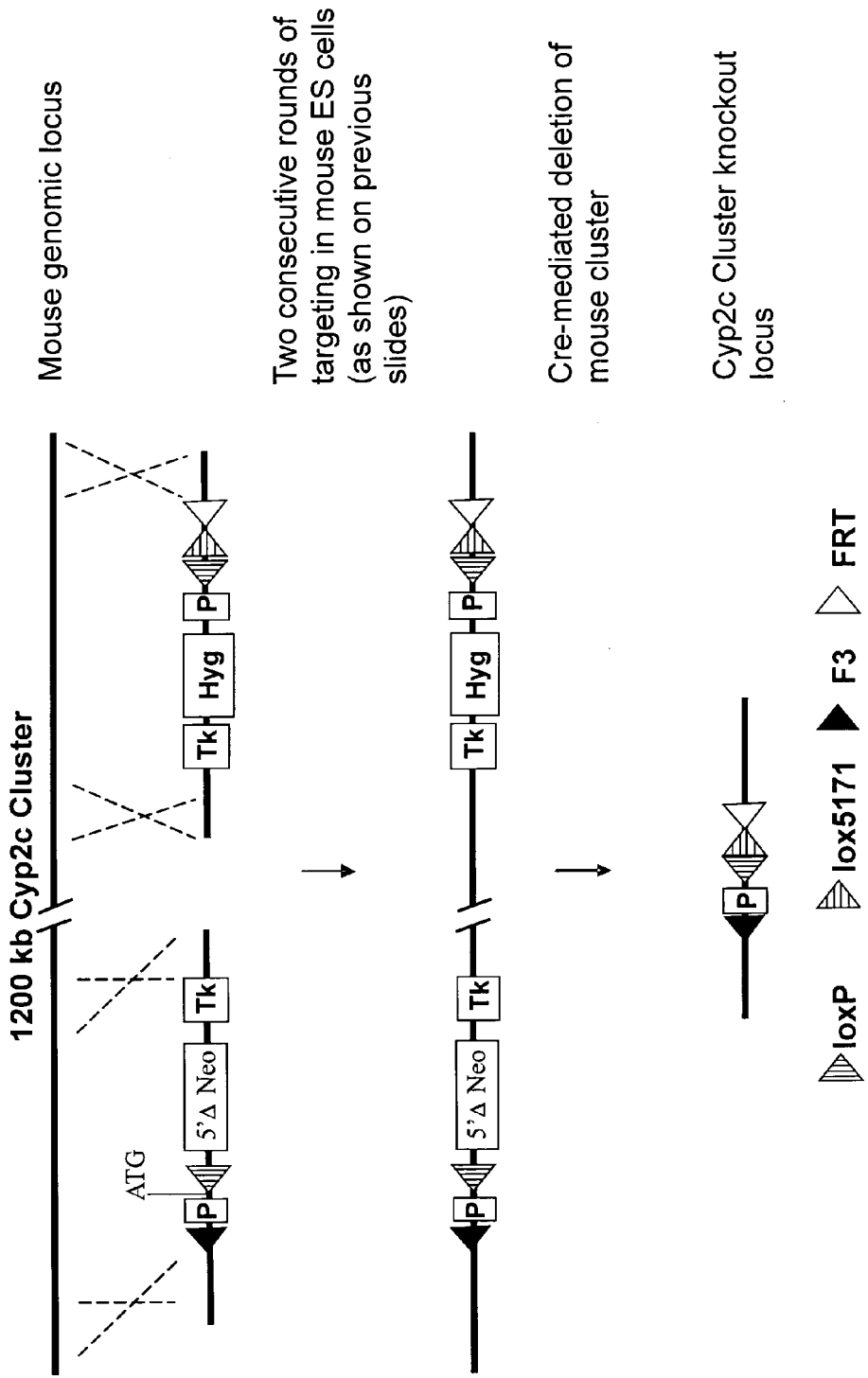

PCR No. 1527
(Detects the deletion of the mouse Cyp2c Cluster)

Primers used to detect Cyp2c Cluster deletion:
1398_1: oC2cCdf1 GACATTGACATCCACTTTGCC
1527_2: oC2cCdr1 GATGGATGTGTGGAATGAAGAG
Expected fragment: 559bp

PCR control primers:
1281_1: GTGGCACGGAACTTCTAGTC
1281_2: CTTGTCAAGTAGCAGGAAGA
Expected fragment: 335bp IDs: 1=Marker, 2=234258, 3=234259, 4=236201, 5=236205, 6=236206, 7=H2O, 8=pos. Control, 9=B6 Wt DNA PCR No. 1560
(Detects the wild type mouse Cyp2c Cluster)

585bp
307bp

Primers used to detect the wt Cyp2c Cluster:
1560_1: o2C9i55o6 CTACAATGCTCTGCCTACCC
1560_2: o2C9i55o7 AAATCTGACTCCCTCTTCTGG
Expected fragment: 307bp

PCR control primers:
1260_1: GAGACTCTGGCTACTCATCC
1260_2: CCTTCAGCAAGAGCTGGGAC
Expected fragment: 585bp IDs: 1=Marker, 2=234258, 3=234259, 4=236201, 5=236205, 6=236206, 7=H2O, 8=pos. Control, 9=B6 Wt DNA 1. Confirmation of the absence of the mouse Cyp3a Cluster

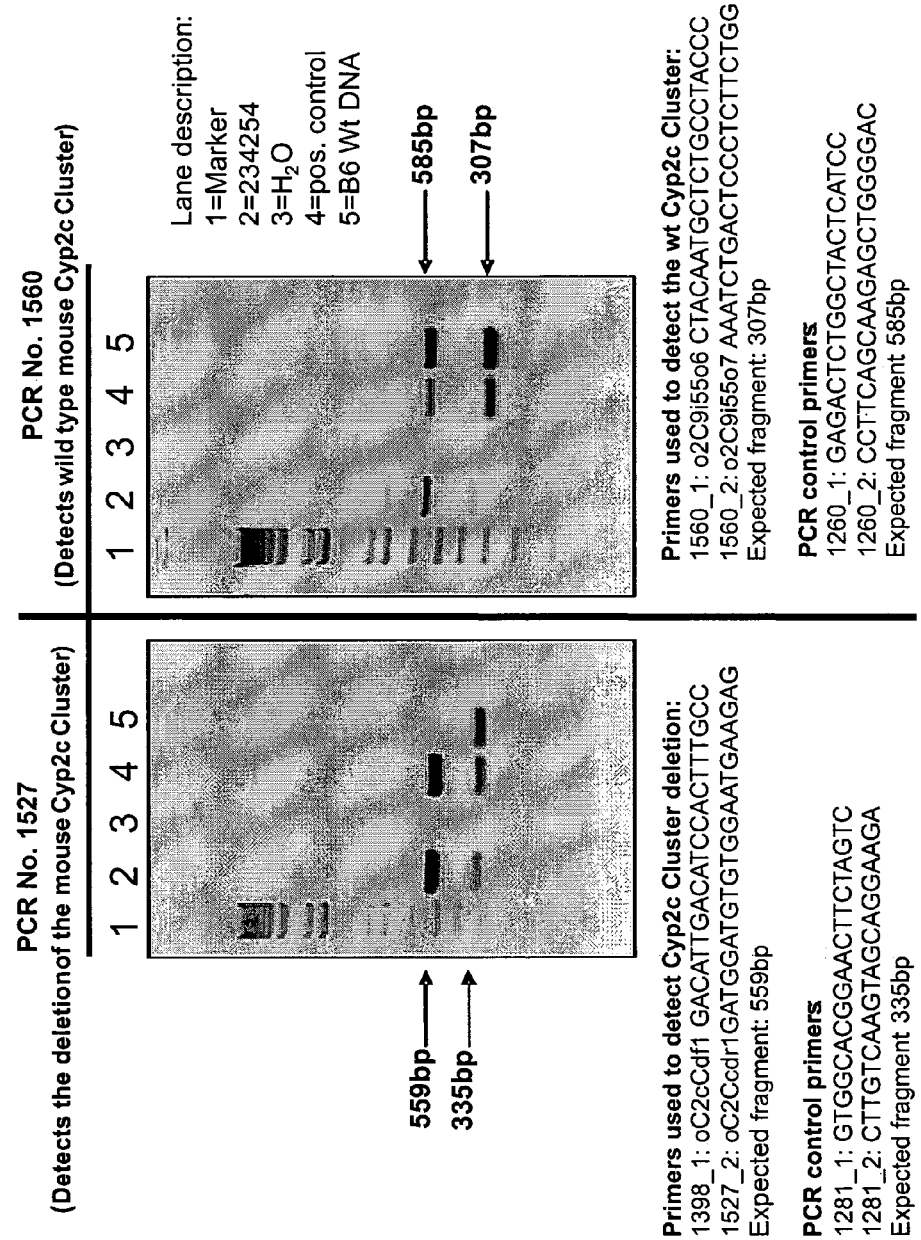

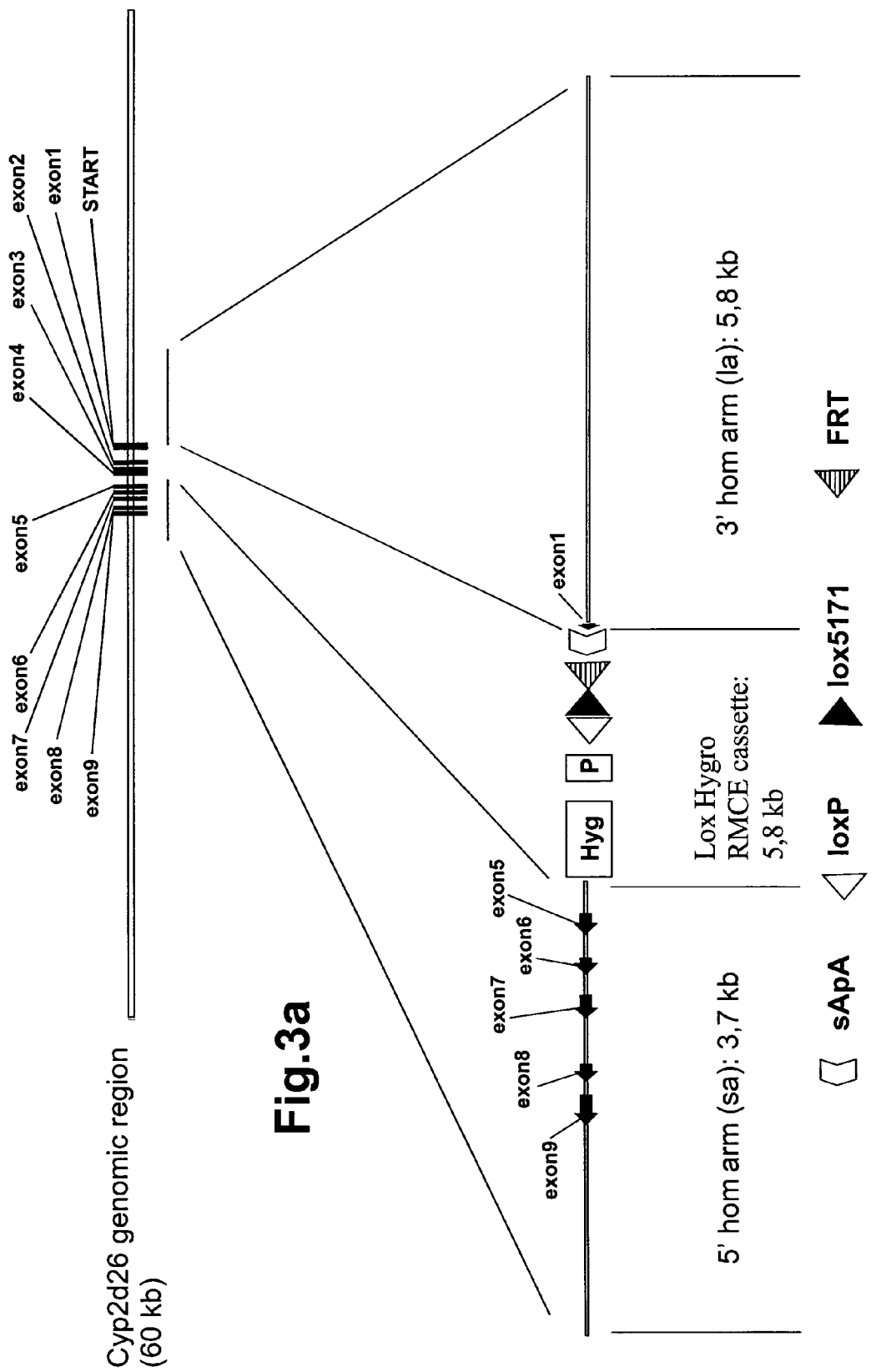

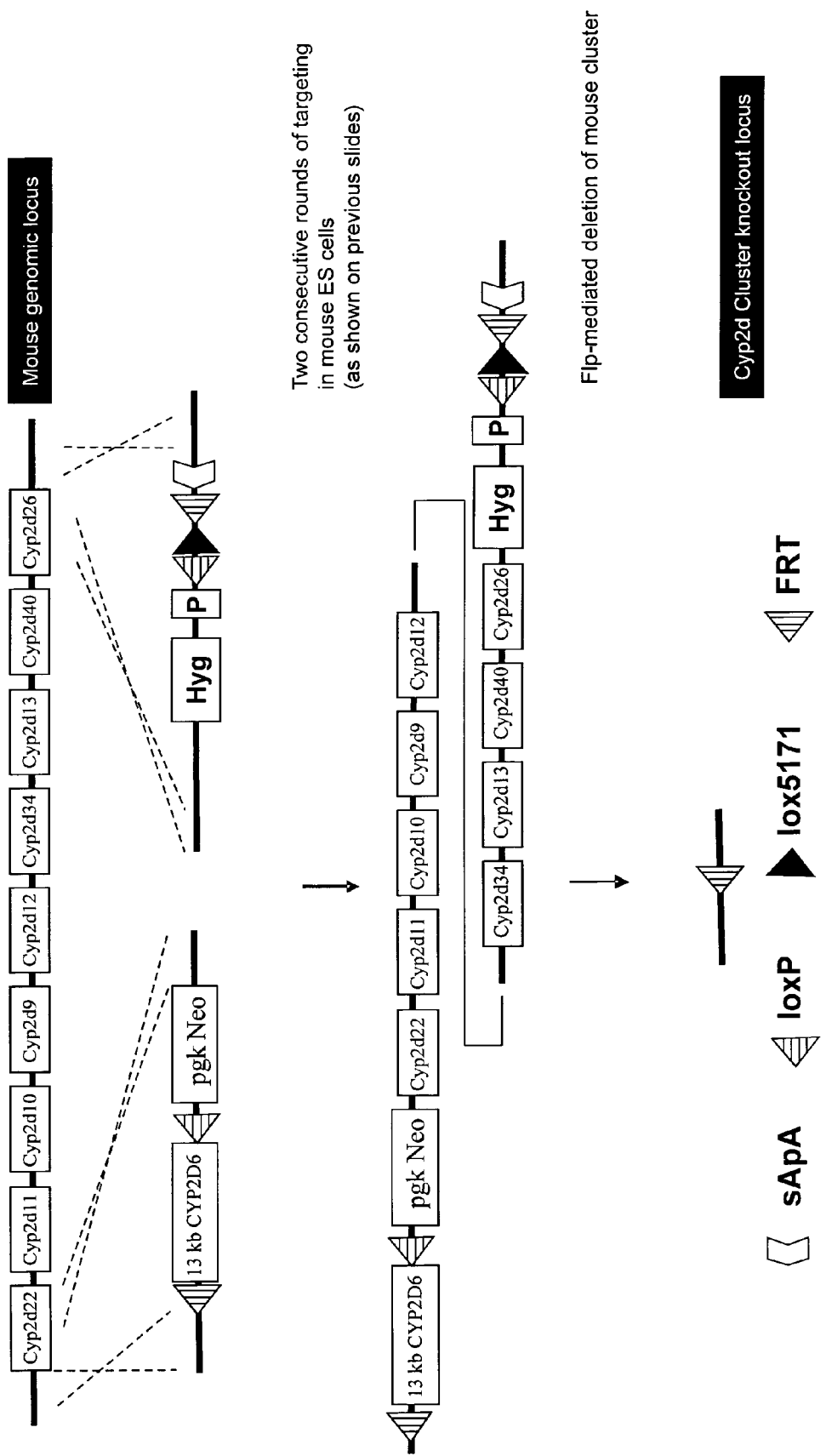

PCR No. 1532
(Detects the deletion of the mouse Cyp2d Cluster)

Primers used to detect Cyp2d Cluster deletion:
1532_1: oC2Ddt_6 GGCATCAGTCAGTCAAATCTCGGG
1463_1: oC2Ddt_3 GGCCAGAATGACCTAGAAC
Expected fragment: 678bp IDs: 1=Marker, 2=232879, 3=232880, 4=232885, 5=234549, 6=234550, 7=H2O, 8=pos. Control, 9=B6 Wt DNA PCR No. 1540
(Detects the wild type mouse Cyp2d Cluster)

1  2  3  4  5  6  7  8  9

← 340bp

Primers used to detect the wt Cyp2d Cluster:
1540_1: oC2Dc5_17 ACTCACCGTCCCCACCCTC
1540_2: oC2Dc5_18 CAAGGGCCTCCGAGTAAACTG
Expected fragment: 340bp IDs: 1=Marker, 2=232879, 3=232880, 4=232885, 5=234549, 6=234550, 7=H2O, 8=pos. Control, 9=B6 Wt DNA

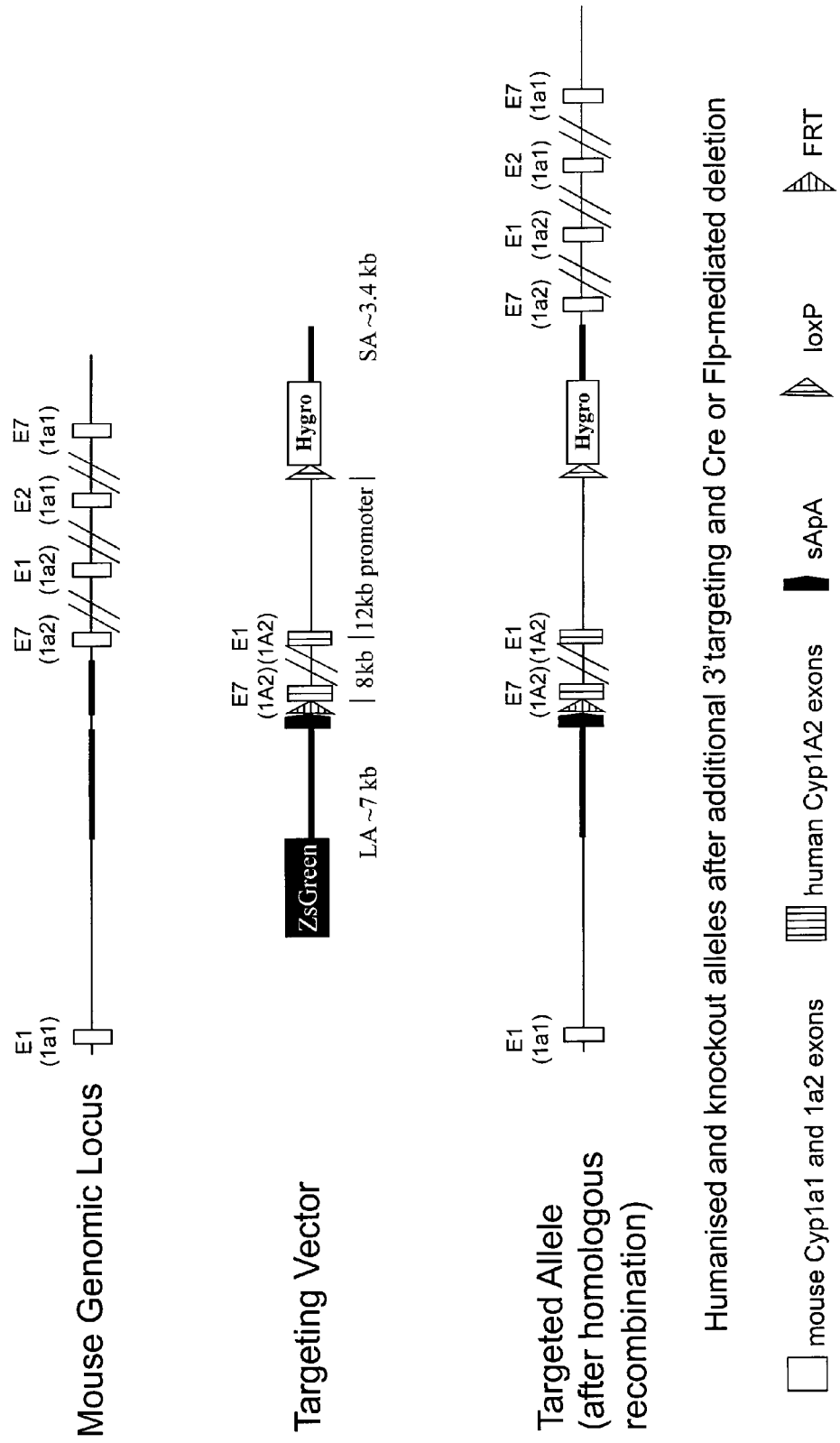

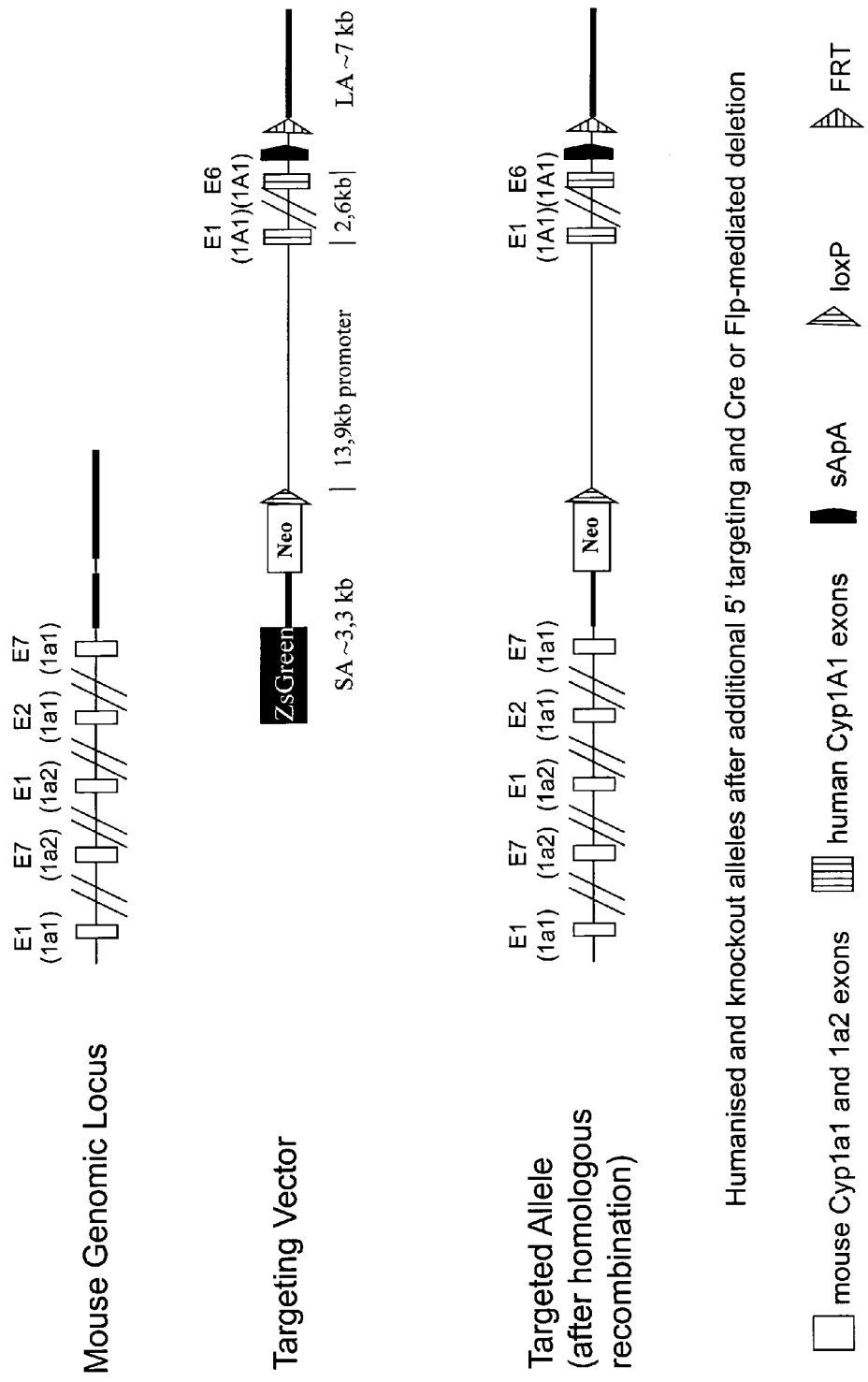

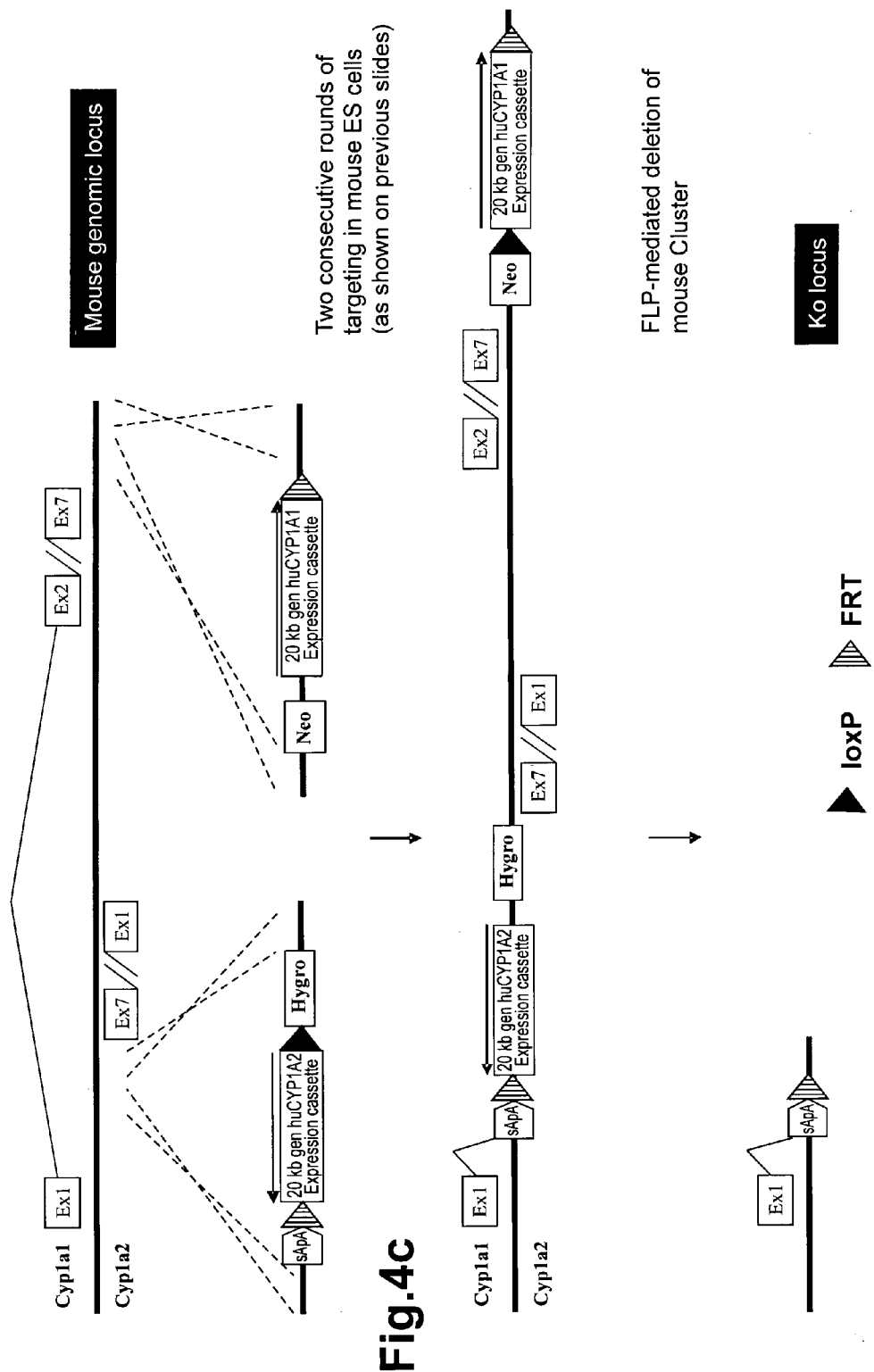

KNOCKOUT MICE FOR A P450 GENE CLUSTER

The invention relates to the generation of mouse models of drug metabolism in which clusters of genes that are involved in drug metabolism have been knocked out.

The development of new drugs and chemicals for therapeutic use or for other purposes is extremely complex. Of particular importance is the understanding of how these chemical agents are handled in the body, whether they have appropriate pharmacokinetics and whether, as a consequence of metabolism, any safety issues arise. Many of the proteins that are involved in the metabolism, disposition and elimination of drugs are members of multigene families that exhibit very marked species differences in gene number, function and regulation. For these reasons, experiments carried out in laboratory animals to establish routes of metabolism or toxicity can be severely compromised and, as a consequence, do not faithfully represent the human situation.

One example of this complexity is reflected in the mammalian cytochrome P450 system, where the sizes of multigene families of proteins which carry out particular metabolic functions vary enormously between species. Suggestions have been made in the literature to generate humanised mouse models whereby the human P450 gene is introduced into the mouse genome. However, unless the mouse gene is annulled at the same time, there will be significant interference from the activity of this gene which will ultimately render any readout from the system meaningless. More sophisticated approaches suggest annulling equivalent murine genes at the time of humanisation (see WO2006/064197) and this allows for the human sequences to replace the mouse functionality.

However, according to Nelson et al., 2004 (Pharmacogenomics 14(1): 1), there are approximately 72 functional genes in the mouse, but only about 27 in the human. Accordingly, whilst there are a few genes that are directly orthologous, such as CYP2E1, CYP1A1 and CYP1A2, for many genes there are only a few genes in the human, but numerous equivalent genes in the mouse. Examples include the CYP2A/2B gene family and CYP2D. WO2006/064197 suggests swapping individual human genes for multiple equivalent murine genes in clusters, and it is hoped that this will allow detailed analysis of the characteristics of human drug metabolism in mouse models.

However, attempts have not, as yet, been made to delete clusters of mouse P450 genes without replacing their function with human equivalents. Enzymatic reactions carried out by these P450 enzymes are involved in critically important life processes. Indeed, mutations in a number of CYP genes are responsible for inborn errors or metabolism and contribute to several important clinically relevant diseases.

However, it would be very advantageous to be able to delete the entire cytochrome P450 gene clusters individually and in combination so that mice can be created where these important metabolic functions can be studied. A mouse where multiple gene clusters have been deleted would allow the generalised role of the cytochrome P450 system in defining chemical/drug pharmacokinetics, biodistribution and toxicity to be established. These models would have great utility and application on their own and when combined with models humanised for particular gene families or clusters.

SUMMARY OF THE INVENTION

According to the present invention, there is provided a mouse in which all members of a multigene cluster encoding drug metabolising enzymes have been rendered inoperable, and which contains no human replacement genes possessing equivalent functions to those of the genes in the deleted cluster.

We demonstrate herein that the deletion of all the cytochrome P450 genes from a particular P450 cluster in all tissues of a mouse results in an apparently normal and viable mouse line. This finding intimates that the housekeeping roles attributed to these cytochrome P450 enzymes may not be essential for survival or fertility after all, in marked disagreement to the predicted phenotypic outcome, and paves the way for the development of individual and multiple P450 gene cluster knockouts in mice.

This is a considerable surprise. To date there have been no reports in the literature of mice in which any gene clusters encoding P450 drug metabolising enzymes have been deleted. One reason for this is thought to be that the cytochrome P450 system, in addition to playing a major role in the metabolism and disposition of foreign chemicals, is known to be implicated in the metabolism and disposition of a number of hormones essential for embryonic development and normal homeostasis. Examples include retinoic acid and steroid hormones. It would be anticipated that the deletion of an entire cytochrome P450 gene cluster would result in embryonic or neonatal lethality. That this does not occur after all comes as a considerable surprise.

Models created in this manner result in total deletion of these drug metabolising functions. Accordingly, such models have a wide range of potential applications. In the first instance, for example, such models can be used in establishing the role of P450 metabolism in the efficacy, toxicity, pharmacokinetics and distribution of drugs and chemicals. Another possibility is the total deletion of a cluster of phase 2 drug metabolising enzymes, such as, for example, the UGT1A and/or GST genes.

The inventors consider it to be of utmost importance when conducting such studies that as many as possible of the genes encoding proteins with relevant functions are deleted in the test animal. One reason for this is that there is a high degree of redundancy between drug metabolism genes, particularly the P450 genes. An example can be provided by the CYP2D6 P450 cluster, in which there are nine functional genes that have overlapping substrate specificity, corresponding to only one functional gene in humans. For this reason, there is little value in merely deleting one of the genes in the mouse cluster and retaining the remainder as functional modules.

By "multigene cluster" is meant a cluster of more than 2 genes encoding drug metabolising enzymes. The term "cluster" as used herein is thus any region of the genome which has the ability to generate more than two gene products, and includes multiple splicing of the same gene.

For example, there are considered to be seven P450 gene clusters in the mouse; the Cyp2abfgst cluster, the Cyp2c cluster, the Cyp2d cluster, the Cyp2j cluster, the Cyp3a cluster, the Cyp4abx cluster and the Cyp4f cluster.

According to current knowledge, the Cyp2abfgst cluster comprises the following functional genes: 2s1, 2b10, 2b13, 2b9, 2a4, 2b23, 2b19, 2g1, 2a5, 2a22, 2a12, 2f2, 2t4. Accordingly, in one aspect the invention provides a mouse in which these genes have been rendered inoperable in all tissues, and which contains no replacement genes possessing equivalent functions to the functions of the genes in the cluster. Preferably, all 13 of these genes are deleted, although there may be circumstances in which it might be of interest to delete only a proportion of these genes, for example, 3, 4, 5, 6, 7, 8, 9, 10, 11, or only 12.

According to current knowledge, the Cyp2c cluster comprises the following functional genes: 2c55, 2c65, 2c66, 2c29, 2c38, 2c39, 2c67, 2c68, 2c40, 2c69, 2c37, 2c54, 2c50, 2c70, 2c44. Accordingly, in one aspect the invention provides a mouse in which these genes have been rendered inoperable in all tissues, and which contains no replacement genes possessing equivalent functions to the functions of the genes in the cluster.

Preferably, all 15 of these genes are deleted, although there may be circumstances in which it might be of interest to delete only a proportion of these genes, for example, 3, 4, 5, 6, 7, 8, 9, 10, 11, 12, 13, or only 14. For example, the 2c44 gene was specifically excluded from the knockout described in Example 2, on the basis that this gene is located 4.1 Mb downstream of the main mouse Cyp2c cluster and is separated from the main cluster by several genes not related in any way to Cyp genes. Consequently, the excision of these unrelated genes would not be desirable and might confuse the resulting phenotype.

According to current knowledge, the Cyp2d cluster comprises the following functional genes: 2d22, 2d11, 2d10, 2d9, 2d12, 2d34, 2d13, 2d40 and 2d26. Accordingly, in one aspect the invention provides a mouse in which these genes have been rendered inoperable in all tissues, and which contains no replacement genes possessing equivalent functions to the functions of the genes in the cluster. Preferably, all 9 of these genes are deleted, although there may be circumstances in which it might be of interest to delete only a proportion of these genes, for example, 3, 4, 5, 6, 7 or only 8. Deletion of the genes in this mouse cluster actually reflects a real human polymorphism, since the expression of CYP2D6 from the equivalent human gene cluster expression is absent in around 6% of Caucasian individuals. This protein plays a major role in the metabolism of neuroleptic drugs (e.g. anti-depressants and drugs used for treatment of schizophrenia), and is thus of significant importance. Pharmaceutical companies are reluctant to back a drug that is metabolised by CYP2D6 and therefore need to know as soon as possible during development of any drug, whether or not it has a CYP2D6 liability. It is thus of immense benefit to be able to study the metabolism of drugs, particularly of anti-depressants, in both the presence and absence of CYP2D6 levels.

According to current knowledge, the Cyp2j cluster comprises the following functional genes: 2j13, 2j12, 2j7, 2j11, 2j8, 2j6, 2j9 and 2j5. Accordingly, in one aspect the invention provides a mouse in which these genes have been rendered inoperable in all tissues, and which contains no replacement genes possessing equivalent functions to the functions of the genes in the cluster. Preferably, all 8 of these genes are deleted, although there may be circumstances in which it might be of interest to delete only a proportion of these genes, for example, 3, 4, 5, 6 or only 7.

According to current knowledge, the Cyp3a cluster comprises the following functional genes: 3a13, 3a57, 3a16, 3a41, 3a11, 3a25 and 3a59. Accordingly, in one aspect the invention provides a mouse in these genes have been rendered inoperable in all tissues, and which contains no replacement genes possessing equivalent functions to the functions of the genes in the cluster. All 7 of these genes may be deleted, although there may be circumstances in which it might be of interest to delete only a proportion of these genes, for example, 3, 4, 5 or only 6. For example, a preferred embodiment of the invention is a mouse in which the 3a57, 3a16, 3a41, 3a11 and 3a25 genes are deleted, yet either or both the 3a13 and 3a59 genes are left intact. Both these genes are physically located outside of the cluster and separated from the rest of the Cyp3a genes by genes that don't belong to the Cyp family. Since the deletion of Cyp-unrelated genes would obscure the value of the models of the invention, this is not ideal and therefore is less preferred. Additionally, the knockout of the cluster that includes also these genes is technically challenging and could only be achieved by an additional knockout of those particular genes at the ES cell level in cells which also contain a deletion of the rest of the cluster.

According to current knowledge, the Cyp4abx cluster comprises the following functional genes: 4x1, 4a29, 4a12a, 4a12b, 4a30b, 4a14, 4a10, 4a31, 4a32, 4b1. Accordingly, in one aspect the invention provides a mouse in which these genes have been rendered inoperable in all tissues, and which contains no replacement genes possessing equivalent functions to the functions of the genes in the cluster. Preferably, all 10 of these genes are deleted, although there may be circumstances in which it might be of interest to delete only a proportion of these genes, for example, 3, 4, 5, 6, 7, 8 or only 9.

According to current knowledge, the Cyp4f cluster comprises the following functional genes: 4f39, 4f17, 4f16, 4f37, 4f40, 4f15, 4f14 and 4f13. Accordingly, in one aspect the invention provides a mouse in which these genes have been rendered inoperable in all tissues, and which contains no replacement genes possessing equivalent functions to the functions of the genes in the cluster. Preferably, all 8 of these genes are deleted, although there may be circumstances in which it might be of interest to delete only a proportion of these genes, for example, 3, 4, 5, 6 or only 7.

The UGT1A cluster comprises the following functional genes: 1a1, 1a2, 1a5, 1a6, 1a6a, 1a7c, 1a8, 1a9 and 1a10. Accordingly, in one aspect the invention provides a mouse in which these genes have been rendered inoperable in all tissues, and which contains no replacement genes possessing equivalent functions to the functions of the genes in the cluster. All 9 of these genes are deleted, although there may be circumstances in which it might be of interest to delete only a proportion of these genes, for example, 3, 4, 5, 6, 7 or only 8. Since deletion of the UGT1a 1 gene causes disease, it is preferred that this gene is not deleted.

Combinations of cluster deletions are also envisaged according to the method of the invention. Accordingly, multiple P450 clusters may in some embodiments of the invention be rendered inoperable. For example any 2 of the Cyp2abfgst cluster, the Cyp2c cluster, the Cyp2d cluster, the Cyp2j cluster, the Cyp3a cluster, the Cyp4abx cluster, the Cyp4f cluster may be may be deleted in the same animal. In other embodiments, 3, 4, 5, 6 or even all 7 of the gene clusters might be deleted in order to generate a mouse with a completely null P450 background. Preferred combinations of clusters to knockout are those comprising 2 or all 3 of Cyp3a, 2c and 2d; e.g. Cyp3a and Cyp2c; Cyp2c and Cyp2d and Cyp3a and Cyp2d. A combination of Cyp3a and Cyp2c cluster deletions is preferred, which knocks out the vast majority of P450 metabolism.

These models provide a significant advantage over the deletion of individual cytochrome P450 isozymes because of the functional redundancy between members of the same gene families and, indeed, between gene families.

Preferably, the P450 functionality is deleted in all tissues of the animals of the present invention. It is a widely-accepted misconception that the liver is the only truly important tissue for drug metabolism. The reality is far from this; in fact P450 function is expressed across a wide range of tissues other than the liver; particular examples include the gastro-intestinal tract and the blood brain barrier. The complete abrogation of function across all tissues is thus necessary in order to assess properly the effects of P450 cluster knockout. Using currently available technology, this is only practically achievable using technology which knocks out expression of all genes in the P450 cluster at the embryonic stem cell stage. Because of the developmental role assigned to P450 enzymes, it has always been assumed that their wholesale knockout would not be possible.

The models of the invention thus provide advantages over other models where a particular P450 system has been inactivated. One example is the conditional inactivation of cytochrome P450 reductase, which only occurs in the liver. In contrast, in the models of the present invention, deletion of the enzymes preferably occurs in all tissues.

It is possible that in some circumstances the knockout of an entire cluster or combination of clusters might cause lethality, and in this scenario, according to the invention, it may be preferable to knockout a gene, combination of genes or cluster in just one tissue. The most appropriate tissue to which the knockout should be confined in such circumstances would be the liver, due to the role of this tissue in drug metabolism.

The experimental approach of the invention also has great advantages over the use of cytochrome P450 inhibitors, for a number of reasons. Firstly, inhibitors lacking specificity can have pharmacological or toxicological effects in their own right. Second, such molecules cannot be used in a chronic dosing situation. Furthermore, inhibitors often modulate the therapeutic or toxicological properties of the compounds that are being tested. They also do not have the capacity to inhibit all cytochrome P450s within a particular gene family, simultaneously, with equivalent levels of potency. Finally, experiments involving the use of inhibitors are much more onerous, complex and difficult to interpret.

The generation of mouse lines according to the invention would markedly increase our understanding of the factors which determine drug and chemical responses in man. These models can be applied in a number of different screening scenarios, including, for example, efficacy screening, PK/PD modelling and drug safety testing. The knockout models of the invention can be of particular interest in those cases where a rodent-specific metabolite(s) not found in humans is formed, which could obscure the efficacy, PK/PD or safety results obtained from conventional animal tests.

One very good reason for the utility of the mouse models of the present invention is that mice metabolise most drugs far more quickly than humans, almost by a factor of 10, generally because of slower rates of P450 metabolism. Accordingly, mice will perhaps exhibit a 30 minutes half-life where the equivalent drug will have a half-life of some hours in the human. Of course, this has the effect that the normal pathways of disposition are masked in the mouse, because there is no opportunity for these to take effect. Accordingly, deleting one or more mouse P450 clusters, particularly the predominant Cyp3a and 2c clusters, has the effect of removing these pathways of drug disposition from contention. Humanisation of such knockout mice for the human P450 clusters would then allow human drug metabolism pathways to be evaluated without interference from the endogenous mouse enzymes.

The animal models of the invention are interesting as drug models in their own right. For example, they allow drug metabolism to be assessed in the absence of the enzymes that would, had they not been deleted, function to metabolise that drug. Accordingly, the animal models of the invention allow an assessment of the degree of redundancy within the P450 system, whereby other P450 enzymes can take over when the first choice enzyme is not present. This also allows evaluation of whether those second choice enzymes, perhaps through exploitation of different reaction pathways, act to generate toxic secondary metabolites which would not normally be produced.

It is a feature of the mice of the present invention that they should contain no replacement genes possessing equivalent functions to the function of the genes in the P450 cluster. By this is meant that the P450 function encoded by the cluster is truly rendered inoperable and not replaced by a homologous or orthologous cluster from another organism. Although such animals are useful in their own right, and may even be created downstream (for example, animals in which the human P450 gene cluster is introduced into the mouse). However, such animals are intentionally excluded from the scope of the present invention.

By "equivalent function" is meant any gene or gene cluster that is functionally capable of replacing the P450 function which is rendered inoperable. Accordingly, examples include acknowledged orthologous counterparts in other organisms. Examples of human and murine orthologues are known to those of skill in the art and many are listed by Nelson et al., 2004 (Pharmacogenomics 14(1): 1).

A preferred drug model according to the invention is a mouse in which the Cyp3a cluster has been rendered inoperable in all tissues, and which contains no replacement genes possessing equivalent functions to the function of the genes in the Cyp3a cluster. The human equivalent genes to the Cyp3a murine cluster are CYP3A4, 3A5, 3A7 and 3A43. The generation and partial characterisation of a mouse according to this aspect of the invention is described in the examples, in which all the genes 3a57, 3a16, 3a41, 3a11, 3a25 and 3a59 are deleted; this mouse forms one aspect of the present invention. As stated above, it is a great surprise and a very significant result that a viable mouse with this genotype has been generated, since existing dogma would dictate that such a homozygous deletion would cause embryonic lethality.

Initial characterisation of Cyp3a cluster KO according to this aspect of the invention has revealed the following phenotypic features:

A. In one embodiment, a mouse according to this aspect of the invention displays plasma clinical chemistry parameters which fall within the known normal range for untreated wild type mice, e.g. C57BL/6J, for triglycerides, alanine transferase, alkaline phosphatise, aspartate aminotransferase, albumin, total bilirubin, creatine kinase, high density lipoprotein and low density lipoprotein.

B. In a second embodiment, a mouse according to this aspect of the invention displays a pharmacokinetic profile of midazolam following IP administration which has similar total area under the concentration/time curve as that seen in wild type mice, e.g. C57BL/6J, i.e. between 80% and 120% of that seen in wild type mice.

C. In another embodiment, a mouse according to this aspect of the invention in which the calculated total area under the concentration/time curve following IP administration of midazolam is reduced, preferably by 170%-370%, more preferably by 220%-320%, more preferably by 240%-300%, more preferably by 250%-290%, more preferably by 260%-280%, more preferably by 265%-275% upon pre-treatment with rifampicin (e.g. 60 mg/kg, 3 daily doses) when compared to untreated Cyp3a cluster KO mice.

D. In another embodiment, a mouse according to this aspect of the invention displays a significant decrease in the oxidation of 7-benzyloxyquinoline by liver microsomes in comparison with wild type mice, e.g. C57BL/6J, wherein the decrease is to a level <50% of wild type, more preferably a level <40% of wild type, more preferably a level <30% of wild type, more preferably a level <20% of that recorded in wild type mice.

E. In another embodiment, a mouse according to this aspect of the invention displays a significant decrease in the 1'-hydroxylation of midazolam by liver microsomes in comparison with wild type mice, e.g. C57BL/6J, wherein the decrease is to a level <50% of wild type, more preferably a level <40% of wild type, more preferably a level <30% of wild type, more preferably a level <20% of that recorded in wild type mice.

F. In another embodiment, a mouse according to this aspect of the invention displays a significant decrease in the 1'-hydroxylation of midazolam by liver microsomes in comparison with wild type mice, e.g. C57BL/6J, following pre-treatment with rifampicin (e.g. 60 mg/kg, 3 daily doses), wherein the decrease is to a level <50% of wild type, preferably a level <40% of wild type, more preferably a level <30% of wild type, more preferably a level <20% of wild type, more preferably a level <10% of that recorded in wild type mice.

G. In another embodiment, a mouse according to this aspect of the invention displays a significant decrease in the 4'-hydroxylation of midazolam by liver microsomes in comparison with wild type mice, e.g. C57BL/6J, wherein the decrease is to a level <80% of wild type, preferably a level <70% of wild type, more preferably a level <65% of that recorded in wild type mice.

H. In another embodiment, a mouse according to this aspect of the invention displays a significant decrease in the 4'-hydroxylation of midazolam by liver microsomes in comparison with wild type mice, e.g. C57BL/6J, following pre-treatment with rifampicin (e.g. 60 mg/kg, 3 daily doses), wherein the decrease to is a level <50% of wild type, preferably a level <40% of wild type, more a preferably a level <35% of wild type, preferably a level <30% of wild type, more preferably a level <25% of that recorded in wild type mice.

I. In another embodiment, a mouse according to this aspect of the invention displays a slight increase in hydroxylation of midazolam following treatment with rifampicin (e.g. 60 mg/kg, 3 daily doses) in comparison to untreated Cyp3a cluster KO mice, wherein the increase is preferably 101%-150%, more preferably 110%-140%, and more preferably 120-130%. Additionally the increase in hydroxylation is significantly less than the increase seen in hydroxylation upon rifampicin treatment in wild type mice, e.g. C57BL/6J, wherein the increase in hydroxylation is preferably <60% of the increase seen in wild type mice, preferably <50% of the increase seen in wild type mice, more preferably <40% of the increase seen in wild type mice, and more preferably <35% of the increase seen in wild type mice.

J. In another embodiment, a mouse according to this aspect of the invention displays a pharmacokinetic profile of 1'-hydroxymidazolam after IV administration of midazolam following pre-treatment with rifampicin (e.g. 60 mg/kg, 3 daily doses), in which the AUC is smaller than that recorded in wild type mice, e.g. C57BL/6J, wherein the AUC is preferably <60%, more preferably <50%, more preferably <40%, and more preferably <35% of that recorded in wild type mice.

K. In another embodiment, a mouse according to this aspect of the invention displays a pharmacokinetic profile of 1'-hydroxymidazolam after oral administration of midazolam following pre-treatment with rifampicin (e.g. 60 mg/kg, 3 daily doses), in which the AUC is smaller than recorded in wild type mice, e.g. C57BL/6J, wherein the AUC is preferably <90%, more preferably <85% and more preferably <80% of that recorded in wild type mice.

L. In another embodiment, a mouse according to this aspect of the invention displays a significant decrease in the oxidation of 7-benzyloxyquinoline by liver microsomes in comparison with wild type mice, e.g. C57BL/6J, following pre-treatment with rifampicin (e.g. 60 mg/kg, 3 daily doses), wherein the decrease is to a level <50%, more preferably a level <40%, more preferably a level <30%, more preferably a level <20%, and more preferably a level <10% of that recorded in wild type mice.

M. In another embodiment, a mouse according to this aspect of the invention displays a significant decrease in the oxidation of triazolam by liver microsomes in comparison with wild type mice, e.g. C57BL/6J, following pre-treatment with rifampicin (e.g. 60 mg/kg, 3 daily doses), wherein the decrease is to a level <50%, more preferably a level <25%, more preferably a level <10%, more preferably a level <5%, and more preferably a level <2.5% of that recorded in wild type mice.

N. In another embodiment, a mouse according to this aspect of the invention displays a significant decrease in the oxidation of triazolam by intestinal microsomes in comparison with wild type mice, e.g. C57BL/6J, following pre-treatment with rifampicin (e.g. 60 mg/kg, 3 daily doses), wherein the decrease is to a level <50%, more preferably a level <25%, more preferably a level <10%, more preferably a level <5%, more preferably a level <2.5% of that recorded in wild type mice.

O. In another embodiment, a mouse according to this aspect of the invention displays a significant decrease in the oxidation of nifedipine by liver microsomes in comparison with wild type mice, e.g. C57BL/6J, following pre-treatment with rifampicin (e.g. 60 mg/kg, 3 daily doses), wherein the decrease is to a level <50%, more preferably a level <40%, more preferably a level <35%, more preferably a level <30% of C57BL/6J, and more preferably a level <25% of that recorded in wild type mice.

P. In another embodiment, a mouse according to this aspect of the invention displays a significant decrease in the 6β-hydroxylation of testosterone by liver microsomes in comparison with wild type mice, e.g. C57BL/6J, following pre-treatment with rifampicin (e.g. 60 mg/kg, 3 daily doses), wherein the decrease is to a level <50%, more preferably a level <40%, more preferably a level <35%, more preferably a level <30% of that recorded in wild type.

Q. In another embodiment, a mouse according to this aspect of the invention displays a significant increase in the 16β-hydroxylation of testosterone by liver microsomes in comparison with wild type mice, e.g. C57BL/6J, following pre-treatment with rifampicin (e.g. 60 mg/kg, 3 daily doses), wherein the increase is to a level >150%, more preferably a level >200%, more preferably a level >250%, and more preferably a level >300% of that recorded in wild type mice.

R. In another embodiment, a mouse according to this aspect of the invention displays a significant decrease in the oxidation of dibenzylfluorescin by liver microsomes in comparison with wild type mice, e.g. C57BL/6J, following pre-treatment with rifampicin (e.g. 60 mg/kg, 3 daily doses), wherein the decrease is to a level <25%, more preferably a level <20%, more preferably a level <15%, and more preferably a level <12.5% of that recorded in wild type mice.

S. In another embodiment, a mouse according to this aspect of the invention displays a significant increase in the 4-trifluoromethylcoumarin by intestinal microsomes in comparison with wild type mice, e.g. C57BL/6J, following pre-treatment with rifampicin (e.g. 60 mg/kg, 3 daily doses), wherein the increase is to a level >150%, more preferably a level >175%, and more preferably a level >200% of that recorded in wild type mice.

T. In another embodiment, a mouse according to this aspect of the invention displays decreased Benzoxyresorufin O-debenzylation activity compared to wild type mice, e.g. C57BL/6J, wherein the decrease in O-debenzylation activity is preferably to a level <90%, more preferably to a level <80%, more preferably to a level <70%, more preferably to a level <60%, and more preferably to a level <50% of that recorded in wild type mice.

U. In another embodiment, a mouse according to this aspect of the invention displays decreased Benzoxyresorufin O-debenzylation activity compared to wild type mice, e.g. C57BL/6J, when both have been pre-treated with rifampicin (e.g. 60 mg/kg, 3 daily doses), wherein the decrease in O-debenzylation activity is preferably to a level <50%, more preferably to a level <40%, more preferably to a level <35%, and more preferably to a level <30% of that recorded in wild type mice.

V. In another embodiment, a mouse according to this aspect of the invention displays 1, 2, 3, 4, 5, 6, 7, 8, 9, 10, 11, 12, 13, 14, 15, 16, 17, 18, 19, 20, or all 21 metabolic phenotypes of embodiments A-U.

W. In another embodiment, a mouse according to this aspect of the invention does not express detectable levels of Cyp3a in liver microsomes, as determined by western blotting.

X. In another embodiment, a mouse according to this aspect of the invention has elevated levels of expression of Cyp1a in liver microsomes than C57BL/6J mice as determined by western blotting.

Y. In another embodiment, a mouse according to this aspect of the invention displays increased expression of Cyp2c proteins in liver microsomes compared to wild type mice, e.g. C57BL/6J, as determined by western blotting.

Z. In another embodiment, a mouse according to this aspect of the invention displays normal levels of Cyp2d proteins in liver microsomes compared to wild type mice, e.g. C57BL/6J, and increased levels of Cyp2d proteins in liver microsomes compared to wild type mice, e.g. C57BL/6J, as determined by western blotting.

AA. In another embodiment, a mouse according to this aspect of the invention displays levels of Cyp2e proteins in both liver and intestinal microsomes which are not significantly different to wild type mice, e.g. C57BL/6J, as determined by western blotting.

AB. In another embodiment, a mouse according to this aspect of the invention has levels of P450 oxidoreducatase (POR) protein expression which are not significantly different to wild type mice, e.g. C57BL/6J, as determined by Cytochrome C reductase activity.

AC. In another embodiment, a mouse according to this aspect of the invention has Total P450 levels which are significantly higher than that recorded in wild type mice, e.g. C57BL/6J, and which do not change significantly upon pre-treatment with rifampicin (e.g. 60 mg/kg, 3 daily doses).

AD. In another embodiment, a mouse according to this aspect of the invention displays 1, 2, 3, 4, 5, 6, or all 7 protein expression phenotypes of embodiments W-AC.

AE. In another embodiment, a mouse according to this aspect of the invention has liver transcript levels for the Cyp3a11, Cyp3a16 and Cyp3a25 which are preferably >50-fold, more preferably >100-fold, and more preferably >100-fold repressed compared to wild type mice, e.g. C57BL/6J.

AF. In another embodiment, a mouse according to this aspect of the invention has liver transcript levels for Cyp4a13 which are more preferably >5-fold, more preferably >10-fold, more preferably >12.5-fold, and more preferably >15-fold repressed compared to wild type mice, e.g. C57BL/6J.

AG. In another embodiment, a mouse according to this aspect of the invention has liver transcript levels for Cyp2c38 which are preferably >2-fold, more preferably >3-fold, more preferably >4-fold, and more preferably >4.5-fold upregulated compared to wild type mice, e.g. C57BL/6J.

AH. In another embodiment, a mouse according to this aspect of the invention has liver transcript levels for Cyp2a4 which are preferably >1.5-fold, more preferably >2-fold, preferably >2.5-fold, and more preferably >2.8-fold upregulated compared to wild type mice, e.g. C57BL/6J.

AI. In another embodiment, a mouse according to this aspect of the invention has liver transcript levels for GSTP1 which are preferably >1.5-fold, more preferably >2-fold, and more preferably >2.4-fold, upregulated compared to wild type mice, e.g. C57BL/6J.

AJ. In another embodiment, a mouse according to this aspect of the invention has liver transcript levels for MGST3 which are preferably >1.5-fold, more preferably >2-fold, and more preferably >2.3-fold, repressed compared to wild type mice, e.g. C57BL/6J.

AK. In another embodiment, a mouse according to this aspect of the invention has liver transcript levels for UGT2B17 which are preferably >1.5-fold, more preferably >2-fold, more preferably >2.5-fold, and more preferably >2.8-fold upregulated compared to wild type mice, e.g. C57BL/6J.

AL. In another embodiment, a mouse according to this aspect of the invention has liver transcript levels for ABCB10 which are preferably >1.5-fold, more preferably >2-fold, and more preferably >2.2-fold upregulated compared to wild type mice, e.g. C57BL/6J.

AM. In another embodiment, a mouse according to this aspect of the invention has liver transcript levels for CAMK2B which are preferably >1.5-fold, more preferably >2-fold, and more preferably >2.6-fold upregulated compared to wild type mice, e.g. C57BL/6J.

AN. In another embodiment, a mouse according to this aspect of the invention has liver transcript levels for CITED2 which are preferably >1.5-fold, more preferably >2-fold, and more preferably >2.2-fold upregulated compared to wild type mice, e.g. C57BL/6J.

AO. In another embodiment, a mouse according to this aspect of the invention has liver transcript levels for DNAJC12 which are preferably >2-fold, more preferably >3-fold, and more preferably >4.1-fold repressed compared to wild type mice, e.g. C57BL/6J.

AP. In another embodiment, a mouse according to this aspect of the invention has liver transcript levels for FMO5 which are preferably >2-fold, more preferably >2.5-fold, and more preferably >3-fold upregulated compared to wild type mice, e.g. C57BL/6J.

AQ. In another embodiment, a mouse according to this aspect of the invention has liver transcript levels for HSD2B3 which are preferably >2-fold, more preferably >2.5-fold, and more preferably >3-fold upregulated compared to wild type mice, e.g. C57BL/6J.

AR. In another embodiment, a mouse according to this aspect of the invention has liver transcript levels for JUNB which are preferably >2-fold, more preferably >3-fold, more preferably >4-fold, and more preferably >4.1-fold repressed compared to wild type mice, e.g. C57BL/6J.

AS. In another embodiment, a mouse according to this aspect of the invention has liver transcript levels for JUNB which are preferably >3-fold, more preferably >4-fold, more preferably >5-fold, and more preferably >5.1-fold repressed compared to wild type mice, e.g. C57BL/6J.

AT. In another embodiment, a mouse according to this aspect of the invention has liver transcript levels for MAP2K6 which are preferably >2-fold, preferably >2.5-fold, preferably >3-fold, preferably >3.3-fold upregulated compared to wild type mice, e.g. C57BL/6J.

AU. In another embodiment, a mouse according to this aspect of the invention has liver transcript levels for MAP3K1 which are preferably >1.5-fold, more preferably >2-fold, more preferably >2.3-fold repressed compared to wild type mice, e.g. C57BL/6J.

AV. In another embodiment, a mouse according to this aspect of the invention has liver transcript levels for MAP3K3 which are preferably >2-fold, more preferably >2.5-fold, more preferably >2.8-fold repressed compared to wild type mice, e.g. C57BL/6J.

AW. In another embodiment, a mouse according to this aspect of the invention has liver transcript levels for STIP1 which are preferably >1.5-fold, more preferably >2-fold, and more preferably >2.3-fold upregulated compared to wild type mice, e.g. C57BL/6J.

AX. In another embodiment, a mouse according to this aspect of the invention has liver transcript levels for Cyp2a4 which are preferably >2-fold, more preferably >2.5-fold, more preferably >3-fold, and more preferably >3.4-fold upregulated compared to wild type mice, e.g. C57BL/6J, after pre-treatment of the strains with rifampicin (e.g. 60 mg/kg, 3 daily doses).

AY. In another embodiment, a mouse according to this aspect of the invention has liver transcript levels for Cyp2b13 which are preferably >2.5-fold, more preferably >4-fold, more preferably >4.5-fold, more preferably >5-fold, more preferably >5.5-fold upregulated compared to wild type mice, e.g. C57BL/6J, after pre-treatment of the strains with rifampicin (e.g. 60 mg/kg, 3 daily doses).

AZ. In another embodiment, a mouse according to this aspect of the invention has liver transcript levels for Cyp2b10 which are preferably >4-fold, preferably >5-fold, preferably >6-fold, preferably >7-fold, preferably >7.2-fold upregulated compared to wild type mice, e.g. C57BL/6J, after pre-treatment of the strains with rifampicin (e.g. 60 mg/kg, 3 daily doses).

BA. In another embodiment, a mouse according to this aspect of the invention has liver transcript levels for Cyp2b9 which are preferably >2-fold, more preferably >2.5-fold, more preferably >3-fold, and more preferably >3.2-fold upregulated compared to wild type mice, e.g. C57BL/6J, after pre-treatment of the strains with rifampicin (e.g. 60 mg/kg, 3 daily doses).

BB. In another embodiment, a mouse according to this aspect of the invention has liver transcript levels for Cyp2c54 which are preferably >2-fold, more preferably >2.5-fold, more preferably >2.7-fold upregulated compared to wild type mice, e.g. C57BL/6J, after pre-treatment of the strains with rifampicin (e.g. 60 mg/kg, 3 daily doses).

BC. In another embodiment, a mouse according to this aspect of the invention has liver transcript levels for Cyp2c54 which are preferably >2-fold, more preferably >2.5-fold, and more preferably >2.7-fold upregulated compared to wild type mice, e.g. C57BL/6J, after pre-treatment of the strains with rifampicin (e.g. 60 mg/kg, 3 daily doses).

BD. In another embodiment, a mouse according to this aspect of the invention has liver transcript levels for Cyp4a2b which are preferably >2-fold, more preferably >2.5-fold, and more preferably >3-fold, more preferably >3.3-fold upregulated compared to wild type mice, e.g. C57BL/6J, after pre-treatment of the strains with rifampicin (e.g. 60 mg/kg, 3 daily doses).

BE. In another embodiment, a mouse according to this aspect of the invention has liver transcript levels for MGST1 which are more preferably >2-fold, more preferably >2.5-fold, and more preferably >2.7-fold upregulated compared to wild type mice, e.g. C57BL/6J, after pre-treatment of the strains with rifampicin (e.g. 60 mg/kg, 3 daily doses).

BF. In another embodiment, a mouse according to this aspect of the invention has liver transcript levels for MGST3 which are preferably >1.5-fold, more preferably >2-fold, and more preferably >2.4-fold repressed compared to wild type mice, e.g. C57BL/6J, after pre-treatment of the strains with rifampicin (e.g. 60 mg/kg, 3 daily doses).

BG. In another embodiment, a mouse according to this aspect of the invention has liver transcript levels for ABCD1 which are preferably >2-fold, more preferably >2.5-fold, and more preferably >2.7-fold upregulated compared to wild type mice, e.g. C57BL/6J, after pre-treatment of the strains with rifampicin (e.g. 60 mg/kg, 3 daily doses).

BH. In another embodiment, a mouse according to this aspect of the invention has liver transcript levels for ABCD3 which are preferably >2-fold, more preferably >2.5-fold, more preferably >3-fold, and more preferably >3.5-fold upregulated compared to wild type mice, e.g. C57BL/6J, after pre-treatment of the strains with rifampicin (e.g. 60 mg/kg, 3 daily doses).

BI. In another embodiment, a mouse according to this aspect of the invention has liver transcript levels for ABCG8 which are preferably >2-fold, more preferably >2.5-fold, and more preferably >2.7-fold upregulated compared to wild type mice, e.g. C57BL/6J, after pre-treatment of the strains with rifampicin (e.g. 60 mg/kg, 3 daily doses).

BJ. In another embodiment, a mouse according to this aspect of the invention has liver transcript levels for ARK1C14 which are preferably >2-fold, more preferably >2.5-fold, and more preferably >2.7-fold upregulated compared to wild type mice, e.g. C57BL/6J, after pre-treatment of the strains with rifampicin (e.g. 60 mg/kg, 3 daily doses).

BK. In another embodiment, a mouse according to this aspect of the invention has liver transcript levels for CAMK2B which are preferably >2-fold, more preferably >3-fold, and more preferably >3.7-fold upregulated compared to wild type mice, e.g. C57BL/6J, after pre-treatment of the strains with rifampicin (e.g. 60 mg/kg, 3 daily doses).

BL. In another embodiment, a mouse according to this aspect of the invention has liver transcript levels for CITED2 which are preferably >2-fold, more preferably >2.5-fold, and more preferably >2.8-fold upregulated compared to wild type mice, e.g. C57BL/6J, after pre-treatment of the strains with rifampicin (e.g. 60 mg/kg, 3 daily doses).

BM. In another embodiment, a mouse according to this aspect of the invention has liver transcript levels for FMO5 which are preferably >2-fold, more preferably >3-fold, more preferably >4-fold, and more preferably >4.7-fold upregulated compared to wild type mice, e.g. C57BL/6J, after pre-treatment of the strains with rifampicin (e.g. 60 mg/kg, 3 daily doses).

BN. In another embodiment, a mouse according to this aspect of the invention has liver transcript levels for HSD3B3 which are preferably >2-fold, more preferably >3-fold, more preferably >4-fold, and more preferably >4.9-fold upregulated compared to C57BL/6J, after pre-treatment of the strains with rifampicin (e.g. 60 mg/kg, 3 daily doses).

BO. In another embodiment, a mouse according to this aspect of the invention has liver transcript levels for JUNB which are preferably >2-fold, more preferably >2.5-fold, and preferably >3-fold repressed compared to wild type mice, e.g. C57BL/6J, after pre-treatment of the strains with rifampicin (e.g. 60 mg/kg, 3 daily doses).

BP. In another embodiment, a mouse according to this aspect of the invention has liver transcript levels for MAP2K6 which are preferably >2-fold, more preferably >2.5-fold, more preferably >3-fold, more preferably >3.6-fold upregulated compared to wild type mice, e.g. C57BL/6J, after pre-treatment of the strains with rifampicin (e.g. 60 mg/kg, 3 daily doses).

BQ. In another embodiment, a mouse according to this aspect of the invention has liver transcript levels for MAP3K1 which are preferably >2-fold, preferably >2.5-fold, preferably >2.7-fold repressed compared to wild type mice, e.g. C57BL/6J, after pre-treatment of the strains with rifampicin (e.g. 60 mg/kg, 3 daily doses).

BR. In another embodiment, a mouse according to this aspect of the invention has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38 or all 39 transcriptomic phenotypes of embodiments AE-BQ.

BS. In another embodiment a mouse to this aspect of the invention has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or all 71 of the phenotypic features of embodiments A-BR.

Another preferred model according to the invention is a mouse in which the Cyp2c cluster has been rendered inoperable in all tissues, and which contains no replacement genes possessing equivalent functions to the function of the genes in the Cyp2c cluster. The human equivalent genes to the Cyp2c murine cluster are 2C8, 2C9, 2C18 and 2C19. A strategy for the generation of a mouse according to this aspect of the invention, in which all of the genes 2c55, 2c65, 2c66, 2c29, 2c38, 2c39, 2c67, 2c68, 2c40, 2c69, 2c37, 2c54, 2c50, 2c70 and 2c44 have been rendered inoperable in all tissues, is described in the examples. Homozygous Cyp2c knock-out mice have been generated.

Another preferred model according to the invention is a mouse in which the Cyp2d cluster has been rendered inoperable in all tissues, and which contains no replacement genes possessing equivalent functions to the function of the genes in the Cyp2d cluster. The human equivalent genes to the Cyp2d murine cluster are 2D6, 2D7 and 2D8. A strategy for the generation of a mouse according to this aspect of the invention, in which all of the genes 2d22, 2d11, 2d10, 2d9, 2d12, 2d34, 2d13, 2d40 and 2d26 have been rendered inoperable in all tissues, is described in the examples. Homozygous Cyp2d knock-out mice have been generated.

In one embodiment, a mouse according to this aspect of the invention in which the calculated total area under the concentration/time curve following IP administration of bufuralol is increased preferably by >5-fold, more preferably >10-fold, more preferably >15-fold, and more preferably >20-fold when compared to wild type mice, e.g. C57BL/6J.

A still further preferred model according to the invention is a mouse in which both the Cyp3a and Cyp2c clusters have been rendered inoperable in all tissues. The generation and partial characterisation of a mouse according to this aspect of the invention is described in the examples, in which all the genes 3a57, 3a16, 3a41, 3a11, 3a25, 3a59, 2c55, 2c65, 2c66, 2c29, 2c38, 2c39, 2c67, 2c68, 2c40, 2c69, 2c37, 2c54, 2c50, 2c70, and 2c44 are deleted; this mouse forms one aspect of the present invention.

According to the invention any P450 cluster may be rendered inoperable. By the term "rendered inoperable" is meant that the genes or gene functions are deleted. This may be by complete deletion of the coding sequences of the genes from the mouse genome. Alternatively, deletion may be accomplished by mutation of the coding sequence, either by way of insertion, deletion or substitution of other sequences. For example, one or more mutations (such as frameshift mutations) may be generated such that any resulting RNA transcript codes for a non-functional or truncated protein. In an alternative, an insertion may be made into the chromosomal sequence to disrupt the amino acid code.

Similarly, a sequence may be exchanged with the P450 gene sequence that is being deleted, such as a selection or marker sequence that can be used as the basis for screening for successful deletants. One such strategy has been devised by Wallace et al (Cell 128, 197-209 2007), albeit in the context of gene exchange, although this is applicable to the method of the present invention. This method envisages an exchange of sequence between mouse chromosome and a BAC or YAC vector, such that two intermolecular homologous recombination events are required for the vector-based replacement sequence to replace the endogenous genomic murine sequence.

In one preferred system, a mechanism of homologous recombination is used to exchange a gene cluster for an alternative sequence in which the cluster is not present. Such a method preferably comprises the steps of: a) incorporating a pair of site-specific recombination sites into the mouse chromosome by homologous recombination such that the mouse target gene cluster that is to be replaced is flanked on each side by a recombination site; and b) effecting recombination between the site-specific recombination sites such that the mouse target gene cluster is excised from the chromosome, replaced by a residual site-specific recombination site.

Methods for performing homologous recombination are known in the art and exploit regions of homology between exogenously supplied DNA molecules and the target chromosome to introduce the RT sites. Under this methodology, 5' and 3' homology arms in the replacement sequence drive recombination between the replacement sequence and target such that the gene cluster is deleted. A methodology utilising this strategy is reported in the applicant's co-pending patent application no. GB0718029.2 filed on 14 Sep. 2007 entitled "Two step cluster deletion and humanisation". This strategy is much more efficient than the Wallace technology expounded above, being an intramolecular recombination event that occurs at a frequency of around 1 in $10^6$.

However, many clusters span significant stretches of the genome of many hundreds of kilobases. One example is the mouse CYP3a gene cluster which spans around 800 kbs even if the Cyp3a13 is not included. In such a scenario, it is much more efficient to utilise a strategy whereby two separate replacement nucleic acids are introduced into the mouse genome in such a way that between them they span the entire cluster; recombination between these two replacement nucleic acids then excises the gene cluster that lies in between.

In this arrangement, each of the replacement sequences is designed such that between the 5' and 3' homology arms lies a selection marker and at least one recombinase target (RT) site such as loxP, lox5171, FRT or F3. In this manner, it is possible to select for successful incorporation of both replacement nucleic acids, that would thus flank the cluster to be deleted. It is then technically simple to excise the cluster by exposure of the mouse cells to an appropriate site-specific recombinase (SSR) that recognises the RT sites. The term "SSR" refers to any protein component of any recombinant system that mediates DNA rearrangements in a specific DNA locus, including SSRs of the integrase or resolvase/invertase classes (Abremski, K. E. and Hoess, R. H. (1992) Protein Engineering 5, 87-91; Khan, et al., (1991) Nucleic acids Res. 19, 851-860; Nunes-Duby et al., (1998) Nucleic Acids Res 26 391-406; Thorpe and Smith, (1998) P.N.A.S USA 95 5505-10) and site-specific recombination mediated by intron-encoded endonucleases (Perrin et al., (1993) EMBO J. 12, 2939-2947). Exposure to SSR enzyme activity results in a DNA rearrangement determined by the disposition of the RT sites, which in a linear DNA molecule results in the intervening sequence being excised, or cut out.

These described recombination steps are preferably performed in a mouse embryonic stem cell, according to methods well known in the art and discussed further below. Embryonic stem cells are cultured cell lines of totipotent cells, wherein the cells, when introduced into an early embryo, will develop to populate all tissues of the developing organism.

The first step in the method is the incorporation of a pair of RT sites into the mouse chromosome. The mouse target gene cluster sequence to be replaced should be flanked on each side by an RT site. Recombination between the two RT sites will thus cut out the intervening gene cluster. Methods for incorporation of RT sites into the chromosome will be known to those of skill in the art, and are preferably performed by exploiting the process of homologous recombination.

The RT pair is preferably selected from the group consisting of LoxP, FRT, attP/attB and rox (Sauer and McDermott. Nucleic Acids Res. 32(20): 6086-95, 2004). This list is provided by way of example only, and is not intended to be limiting. Within this aspect recombination between said site-specific recombination site pairs is to be effected by the corresponding site-specific recombinase, i.e. Cre, FLP, PhiC31 and Dre respectively. It is to be understood that said site-specific recombination can be effected in vivo or in vitro.

As a practical matter, each RT site should be constructed so as to be linked to, and preferably contiguous to a selectable marker. The inclusion of a selectable marker allows the detection of the RT site within the mouse chromosome, and as such allows monitoring for the successful insertion of RT site pair. Each selectable marker is preferably positioned so that it lies in the space between the mouse target sequence and the RT site. This means that upon successful recombination, the selectable markers are removed from the chromosome and thus take no further part in the methodology. In this way, it can be sure that the selectable marker has no perturbing effect on the regulation of the human sequence that remains in the chromosome after humanisation. Each of the selectable markers are preferably different to each other. This allows the insertion of each recombination site to be monitored separately and independently from each other. The selectable markers are preferably genes-encoding some kind of resistance to a chemical compound to which the growing ES cells can be exposed, such as an antibiotic. Examples include use of selectable markers conferring resistance to antibiotics added to the growth medium of cells, for instance the neomycin resistance marker conferring resistance to G418, hygromycin or puromycin. Further examples involve detection using nucleic acid sequences that are of complementary sequence and which will hybridise with, or a component of, the nucleic acid sequence in accordance with the previous aspects of the invention. Examples would include Southern blot analysis, northern blot analysis and PCR.

A preferred strategy involves the creation of altered murine embryonic stem cells, preferably in separate steps, whereby each RT site is incorporated separately, with its selectable marker. The altered embryonic stem cell may be subsequently inserted into a blastocyst. Conventionally, blastocysts are isolated from a female mouse about 3 days after it has mated. It is to be understood that up to 20 altered embryonic stem cells may be simultaneously inserted into such a blastocyst, preferably about 16. Through insertion of altered embryonic stem cells into the blastocyst, the embryonic stem cell will become incorporated into the developing early embryo, preferably by its transplantation into a pseudo-pregnant mouse which has been induced so as to mirror the characteristics of a pregnant mouse. According to this methodology, the blastocyst, containing the altered embryonic stem cell, will implant into the uterine wall of the pseudo-pregnant mouse and will continue to develop within the mouse until gestation is complete. The altered embryonic stem cell will proliferate and divide so as to populate all tissues of the developing transgenic mouse, including its germ-line.

In one aspect of the methodology, the created transgenic mouse may be a chimera, containing altered and non-altered cells within each somatic tissue and within the germ-line.

The methodology for mediating Cre/lox-mediated deletions, suitable for deleting of large fragments of DNA (200 kb to several megabases), has been described in the following papers (Li Z W, Stark G, Gotz J, Rulicke T, Gschwind M, Huber G, Muller U, Weissmann C. Generation of mice with a 200-kb amyloid precursor protein gene deletion by Cre recombinase-mediated site-specific recombination in embryonic stem cells Proc Natl Acad Sci USA. 1996 Jun. 11; 93(12):6158-62. Erratum in: Proc Natl Acad Sci USA 1996 Oct. 15; 93(21):12052; in Su H, Wang X, Bradley A. Nested chromosomal deletions induced with retroviral vectors in mice. Nat. Genet. 2000 January; 24(1):92-5); Call L M, Moore C S, Stetten G, Gearhart J D; A cre-lox recombination system for the targeted integration of circular yeast artificial chromosomes into embryonic stem cells. Hum Mol. Genet. 2000 Jul. 22; 9(12):1745-51).

In order to effect recombination between the RT sites, the genome must be exposed to SSR activity, in the form of an SSR enzyme. As mentioned above, the site-specific recombination event may be effected in vitro or in vivo. Site-specific recombination may be effected by inducing activity of the SSR within the transgenic mouse. Indeed, successful exploitation of site-specific recombination to alter genotype in living systems requires strategies to regulate the recombination event. This can be done by controlling expression of the recombinase mRNA, or protein (Baubonis and Sauer (1993) Nucl Acids Res. 21, 2025-2029; Sauer B, (1994) Curr Opin Biotechnol 5:521-7; Rajewsky et al., (1996) J Clin Invest 98, 600-3; Metzger and Feil, (1999) Curr. Opinions Biotechnology 10, 470-476), such that the expression pattern achieved is confined to the times and places at which these tissue specific elements are active.

Researchers have used direct transfection, infection with recombinant viruses or injection of the DNA or mRNA encoding SSR protein or the protein itself (Konsolaki et al., (1992) New Biol. 4: 551-557) in order to express SSR enzymes. A more precise degree of control may be attained by regulating the activity rather than the expression of these SSR enzymes. One strategy uses fusion proteins in which a SSR enzyme is fused to the ligand binding domain (LBD) of a steroid receptor to give an SSR-LBD protein (see EP-B-0 707 599; also Logie and Stewart (1995) P.N.A.S. USA 92: 5940-5944; Brocard et al., (1997) P.N.A.S. USA 94: 14559-14563; Akagi et al., (1997) Nucleic Acids Res 25, 1766-73). This strategy relies on the application of a ligand for the steroid receptor that activates the SSR activity only when ligand is bound to the receptor moiety. The LBD of the receptor represses the activity of the SSR in the absence of a cognate ligand. Delivery of the cognate ligand relieves repression of the SSR, thus permitting recombination between RT sites.

Induction may thus be effected by inducing transcription of said SSR, inducing translation of the SSR, or removal an inhibitor from the SSR. Alternatively, an SSR may be artificially introduced into said transgenic mouse. One element of the methodology is that site-specific recombination can be effected within the transgenic mouse, so resulting in the excision of the mouse target gene and the concomitant production of a humanised mouse.

Preferably, site-specific recombination can be effected by crossing the transgenic mouse with a deleter strain mouse. The term "deleter strain" as used herein relates to a mouse expressing the site-specific recombinase in its germline, which can be crossed with a transgenic mouse to effect excision of the mouse target gene sequence. In this manner, in vivo recombination produces offspring heterozygous for the gene of interest. Crossing the transgenic mouse with a deleter strain will thus result in the production of progeny, with cells containing the mouse chromosome altered to contain the human replacement gene sequence and the site-specific recombinase, resulting in the excision of the mouse target gene and the functional humanisation of the cells. Such a transgenic mouse will therefore be heterozygous for humanisation of the specific gene or cluster of genes.

In certain embodiments, it may be desired for the site-specific recombinase only to be expressed in a certain tissue of the recombinase strain mouse. It is known in the art that deletion of certain genes or clusters of genes may be lethal or may have sublethal phenotypic effects. Furthermore, replacing such genes with their human equivalents may not prevent lethality. In these circumstances, it may be possible to overcome any such problems of lethality by expressing the site-specific recombinase only in certain tissues, for example, the liver. This will be particularly advantageous if a specific gene is known to be essential in a certain tissue, as expression of the site-specific recombinase in this manner allows the mouse gene to persist in those tissues.

Within this aspect of the invention, the SSR may be albumin-Cre. Albumin-Cre is a specific variant of the SSR Cre which acts on the RT site LoxP. Albumin-Cre is expressed only in the liver, and will therefore allow the mouse target sequence to persist in all tissues except the liver, overcoming possible problems of lethality, whilst providing a functionally humanised liver.

Ultimately, two heterozygous mice produced according to the methodology above may be crossed to produce a transgenic mouse that is homozygous for the human allele of the gene or genes of interest. Crossing two heterozygous transgenic mice will produce a proportion of progeny that are homozygous for the deletion.

In a further embodiment of the invention the transgenic non-human animal is produced de novo so as to include all of the aforementioned features, by the methods as hereinafter disclosed.

It is also possible that the site-specific recombination event be effected in a somatic cell which could then be used as a nuclear transfer donor cell in order to make a colony of cloned mice according to the methodology of WO00/51424 or a variation thereof.

In another embodiment of the invention the mouse of the present invention is produced by crossing. For example, a partial deletant in which a proportion of the genes of a particular cluster have been deleted could be crossed with another partial deletant to generate animals which are deleted for all gene functions within a particular cluster.

In a further embodiment of the invention the transgenic mouse is produced de novo so as to include all of the aforementioned features, by the methods as hereinafter disclosed.

Transgenic Combinations

Ultimately, the animal models of the invention may be exploited as a null background for introducing human genes that may substitute the functions of rodent enzymes, either by integrating these genes directly into the same chromosomal region or through integration at alternative sites. Preferably, human genes will be integrated into the same chromosomal region, since the integrity of the chromosome will be retained and thus physiological patterns of expression and tissue distribution are likely to be similarly retained. Accordingly, in embodiments of the invention relating to the preparation of cells and mice as previously described, such cells and animals may be subjected to further transgenesis, in which the transgenesis is the introduction of an additional gene or genes or protein-encoding nucleic acid sequence or sequences. The transgenesis may be transient or stable transfection of a cell or a cell line, an episomal expression system in a cell or a cell line, or preparation of a transgenic non-human animal by pronuclear microinjection, through recombination events in non-embryonic stem (ES) cells, random transgenesis in non-human embryonic stems (ES) cells or by transfection of a cell whose nucleus is to be used as a donor nucleus in a nuclear transfer cloning procedure.

In particular, it is envisaged that a mouse according to the invention in which one or more P450 gene clusters have been rendered inoperable may be humanised for one or more human genes. Preferably, the deleted cluster is either the Cyp3a cluster, the Cyp2c cluster, and/or the Cyp2d cluster. Any single or multiple combination of these clusters with the humanised drug transporter, humanised transcription factor or humanised phase II drug metabolism enzymes is preferred, as set out below.

For example, such a mouse may be humanised for a transcription factor. Examples of suitable transcription factors include the pregnane X receptor (PXR); the constitutive androstane receptor (CAR); the PPARs ($\alpha$, $\delta$ and $\gamma$), NRF2, the Ah receptor, HNF1 and HNF4. Mice may be humanised for one, two, or even more of these transcription factors. It is also preferred that the endogenous equivalent murine genes have been annulled, as set out in WO2006/064197. A combination of a P450 cluster deletion with a double humanised hCAR and/or hPXR mice on a null background is a preferred model according to the invention.

A mouse according to the invention may also be humanised for a phase-2 drug-metabolising enzyme. Examples of such enzymes include the glucuronyl transferases, for instance, the UGT1A gene or gene cluster, the glutathione transferases, for instance GST (glutathione S-transferases) (including GST-m1 and/or t1 clusters), the sulphonyl transferases and the acetyl transferases. It is also preferred that the endogenous equivalent murine genes have been annulled, as set out in WO2006/064197.

A mouse according to the invention may also be humanised for a drug transporter protein, examples of which include the multi-drug resistance proteins, for instance mdr 1 and mdr3 and multi-drug resistance-associated proteins (MRPs), for example, MRP1 and/or MRP2 and/or MRP6 or from the organic anion transporting polypeptides (OATPs). It is also preferred that the endogenous equivalent murine genes have been annulled, as set out in WO2006/064197.

Cells

Another aspect of the invention relates to cells, modified so as to possess properties according to any one of the above-described aspects of the invention. Hepatocytes and neuronal cells are preferred cell types according to the present invention. The cells may be mouse cells.

Cells according to this aspect of the invention may be created from transgenic mice according to the invention using standard techniques, as will be clear to the skilled reader, imbued with knowledge of the present invention. Suitable methods are described in many standard laboratory manuals, such as Davis et al., Basic Methods in Molecular Biology (1986); Sambrook Molecular Cloning; A Laboratory Manual, Third Edition (2000); Ausubel et al., 1991 [supra]; Spector, Goldman & Leinwald, 1998).

One preferred method of generating such cells is to cross a humanised mouse, as described above, with SV40 immortalised mouse (for example, the immorta-mouse (Taconic). Cells may subsequently be isolated from such animals according to well known techniques in the art. In contrast to prior art transgenic systems, which used the albumin promoter that is only active in the liver and thus only able to generate hepatocytes, cells from transgenic animals generated according to the present invention may be of a diverse selection of different cell types, including cells of significant importance to pharmacokinetics analyses, such as hepatocytes and neuronal cells.

Stem cells isolated from transgenic animals according to the invention, with properties as described above are also useful aspects of the present invention. Such cells may be pluripotent, or partially differentiated. Stem cells may be adult stem cells or embryonic stem cells. More generally, stem cells employed may be from a post-embryonic developmental stage e.g. foetal, neonatal, juvenile, or adult. Stem cells isolated in this manner may be used to generate specific types of cells such as hepatocytes and neuronal cells. Such cells also form an aspect of the present invention.

Cells or animals produced by the method of the invention can be used as model systems for determining the metabolism of drugs or other xenobiotic compounds in other organisms, particularly the human.

Assays

The animals, tissues and cells of the present invention may be used to determine how a drug compound is metabolised. The generation of mouse lines with single or multiple cytochrome P450 gene cluster deletions or the combination of cytochrome P450 gene cluster exchanges for other genes associated with metabolism and disposition of drugs would markedly increase our understanding of the factors which determine drug and chemical responses in man and the relevance of these genes for chemical toxicity. These models could be applied to efficacy screening, PK/PD modelling and drug safety testing.

The cluster knock-outs of the present invention allow humanisation and additional knockout experiments to be performed. Depending on the nature of the animals created, a number of different assay processes may be of interest. In particular, it is possible to ascertain the involvement of a particular drug metabolism gene cluster to the metabolism of any drug compound. It is possible to ascertain the degree of redundancy in any drug metabolism system by assessing the compensatory effects, if any, on metabolism by second choice pathways when a particular cluster is deleted. It is possible to assign the generation of any toxic secondary metabolites to discrete metabolic enzymes. It is possible to examine whether a drug compound influences the disposition or distribution of a transcription factor, a drug metabolising enzyme or a drug transporter protein within the tissues of the body. It is possible to examine whether a drug compound influences the duration of expression of a transcription factor, a drug metabolising enzyme or a drug transporter protein. Other examples of useful assay processes will be clear to those of skill in the art.

It is possible to measure a phenotypic change in the animal, such as a physiological effect. Such a physiological effect may be, for example, a disease condition (such as biliary necrosis) or a toxic side-effect.

It is possible to examine the rate of metabolism of a drug compound. The rate of metabolism may be determined by measuring the toxicity or activity mediated by the administration of the compound, measuring the half-life of the compound, or measuring the level of a drug metabolising enzyme. For example, the rate of metabolism of the compound may be measured as the rate of formation of the oxidized product or the formation of a subsequent product generated from the oxidized intermediate. Alternatively, the rate of metabolism may be represented as the half-life or rate of disappearance of the initial compound or as the change in toxicity or activity of the initial compound or a metabolite generated from the initial compound. The half-life may be measured by determining the amount of the drug compound present in samples taken at various time points. The amount of the drug compound may be quantified using standard methods such as high-performance liquid chromatography, mass spectrometry, western blot analysis using compound specific antibodies, or any other appropriate method.

It is also possible to examine whether under particular circumstances a drug compound is metabolised to a toxic or carcinogenic metabolite, for example, by measuring its covalent binding to tissues, proteins or DNA or by measuring glutathione depletion.

Preferably, measurements of the type described above are performed at more than 1, 3, 5, 10 or more time points after administration of the drug compound.

Accordingly, further aspects of the invention relate to screening methods that are provided to determine the effect of a drug compound on the activity or expression level of a transcription factor, a drug metabolising enzyme or a drug transporter protein. Such methods involve administering a drug compound to a transgenic animal according to any one of the aspects of the invention described above, or a tissue or cell derived therefrom.

The screening step may involve measuring the induction of a gene coding for a transcription factor, a drug metabolising enzyme or a drug transporter protein. The screening step may involve measuring the level of expression of a transcription factor, a drug metabolising enzyme or a drug transporter protein or the duration of such expression. The screening step may involve measuring the distribution of expression of a transcription factor, a drug metabolising enzyme or a drug transporter protein.

The assay can be performed in the presence and absence of the drug compound to ascertain differences in distribution, metabolism and toxicity. The effects of the drug compound in the presence and absence of a particular gene or genes can be ascertained by evaluating the effects of the drug compound on different transgenic animals, cells or tissues. For example, the effects of the drug compound could be evaluated between an animal with a null background and an animal humanised for the gene or genes of interest (e.g. PXR, CAR, MDR1, a phase I metabolising enzyme or a phase 2 metabolising enzyme).

Thus, in a further aspect the invention provides methods for investigating xenobiotic metabolism or toxicity as described herein, comprising administering a drug compound 20 to 2 or more, 3 or more, 4 or more, 5 or more, 6 or more, 7 or more, 8 or more, 9 or more, or 10 or more of the non-human animals, tissues or cells described herein. Preferably, such methods further include a step of comparing the experimental results obtained for different non-human animals, tissues or cells.

More than one drug compound may be administered. For example, a drug compound is determined to activate the CAR transcription factor if the compound mediates induction of the CAR gene. A CAR receptor inverse agonist such as clotrimazole can also administered to an animal expressing the human CAR receptor as a control.

Assays according to further aspects of the invention may provide a screening method for determining whether the metabolism of a first drug compound is modulated by a second drug compound. This method involves administering the first compound in the presence and absence of the second compound to a transgenic animal according to any one of the above-described aspects of the invention, or a tissue or cell derived therefrom, and monitoring for a phenotypic effect. Alternatively, as above, the screening step may involve measuring the induction of a gene, the level, duration or distribution of expression, of a transcription factor, a drug metabolising enzyme or a drug transporter protein. The second compound is determined to modulate the metabolism of the first compound if the second compound effects a change in any one of these tested factors. For example, a physiological effect may be assayed by measuring the toxicity or activity mediated by the administration of the first compound or measuring the half-life of the first drug compound.

In this manner, assays may be used to facilitate the identification of analogs of a drug compound that have reduced or undetectable ability to activate or induce expression of a particular protein, and thus are expected to have fewer side-effects or a longer half-life in vivo.

Various aspects and embodiments of the present invention will now be described in more detail by way of example. It will be appreciated that modification of detail may be made without departing from the scope of the invention.

For the sake of clarity sequences are not drawn to scale. TK=Thymidine Kinase expression cassette, Hygro=Hygromycine expression cassette, ZsGreen=ZsGreen expression cassette, P=Promoter that drives the expression of Neomycin, 5'Δ Neo=ATG-deficient Neomycin.

Figure 1A:
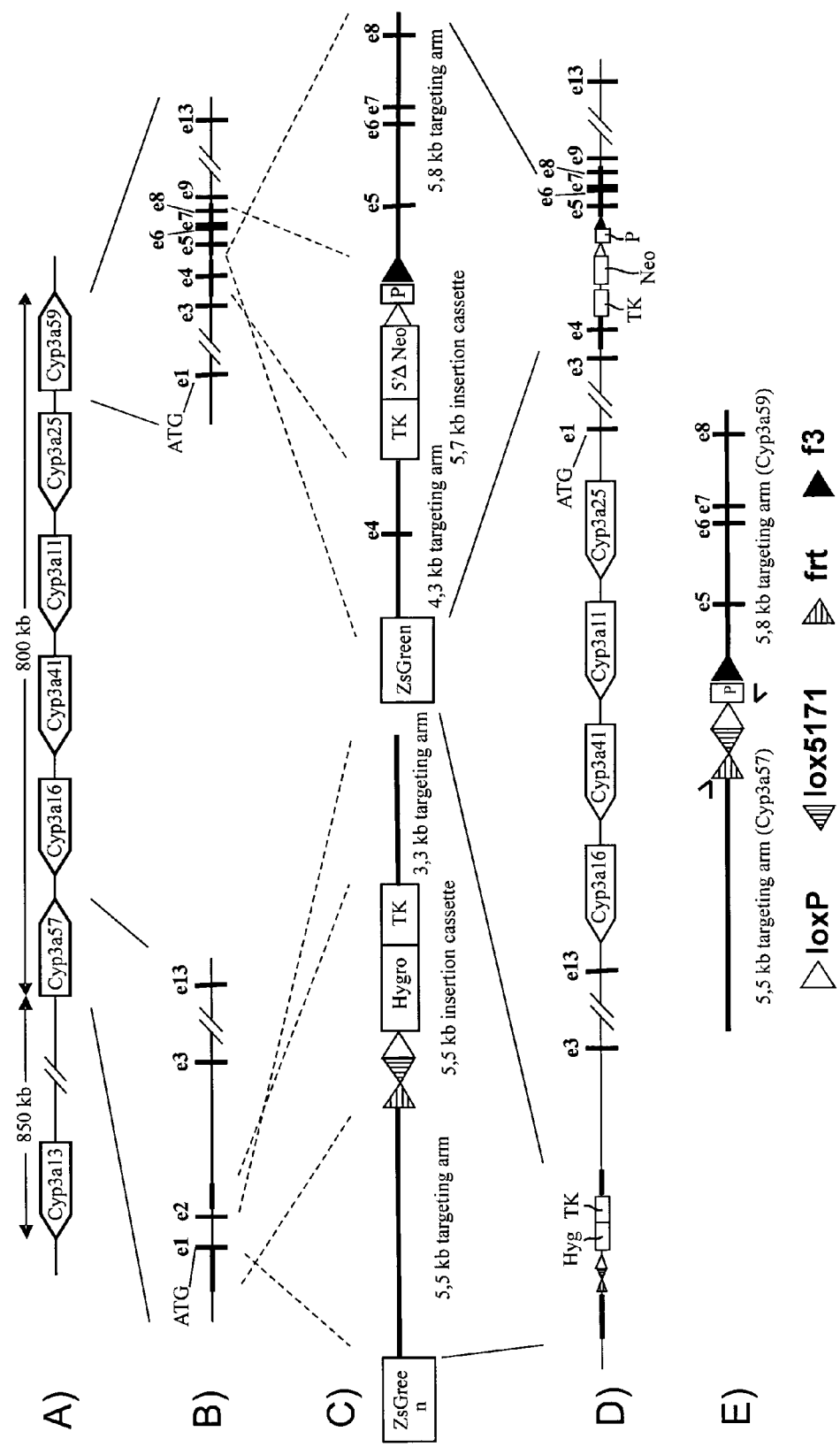
FIG. 1a: Strategy for the deletion of the mouse Cyp3a Cluster. (A) Schematic representation of the chromosomal organisation and orientation of functional genes within the mouse Cyp3a Cluster (adapted from Nelson et al., 2004). Pseudogenes are not listed. (B) Exon/Intron structure of Cyp3a57 and Cyp3a59. Exons are represented as black bars and the ATGs mark the translational start sites of both genes. The positions of the targeting arms for homologous recombination are highlighted as light grey (Cyp3a57) and in dark grey (Cyp3a59) lines, respectively. (C) Vectors used for targeting of Cyp3a57 (left) and Cyp3a59 (right) by homologous recombination. LoxP, lox5171, frt and f3 sites are represented as white, striped, dotted or black triangles, respectively. (D) Genomic organisation of the Cyp3a Cluster in double targeted ES cells after homologous recombination on the same allele at the Cyp3a57 and Cyp3a59 locus. (E) Deletion of the mouse Cyp3a Cluster after Cre-mediated recombination at the loxP sites. All exons and introns from Cyp3a57, Cyp3a16, Cyp3a41, Cyp3a11 and Cyp3a25 are completely deleted and Exons 1 to 4 and the promoter of Cyp3a59. Therefore, the only functional Cyp3a gene that remains after Cre-mediated deletion is Cyp3a13, which is separated from the rest of the Cluster by >800 kb genomic DNA and a number of functional Cyp-unrelated genes. Primers used to demonstrate successful deletion of the mouse Cyp3a Cluster are depicted as arrows.
Figure 1B:
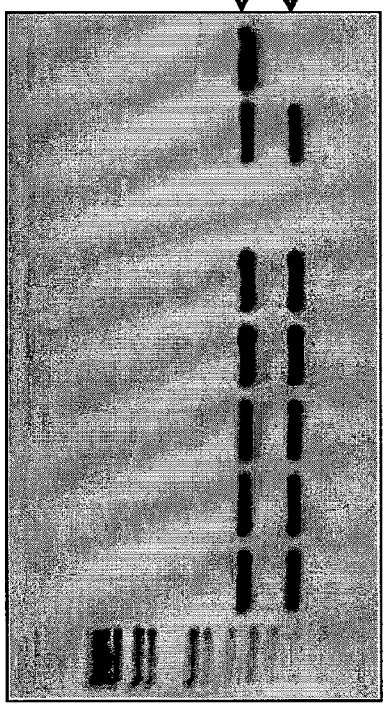

FIG. 1b: PCR confirmation of mouse homozygous for Cyp3a cluster deletion.

Figure 1C:
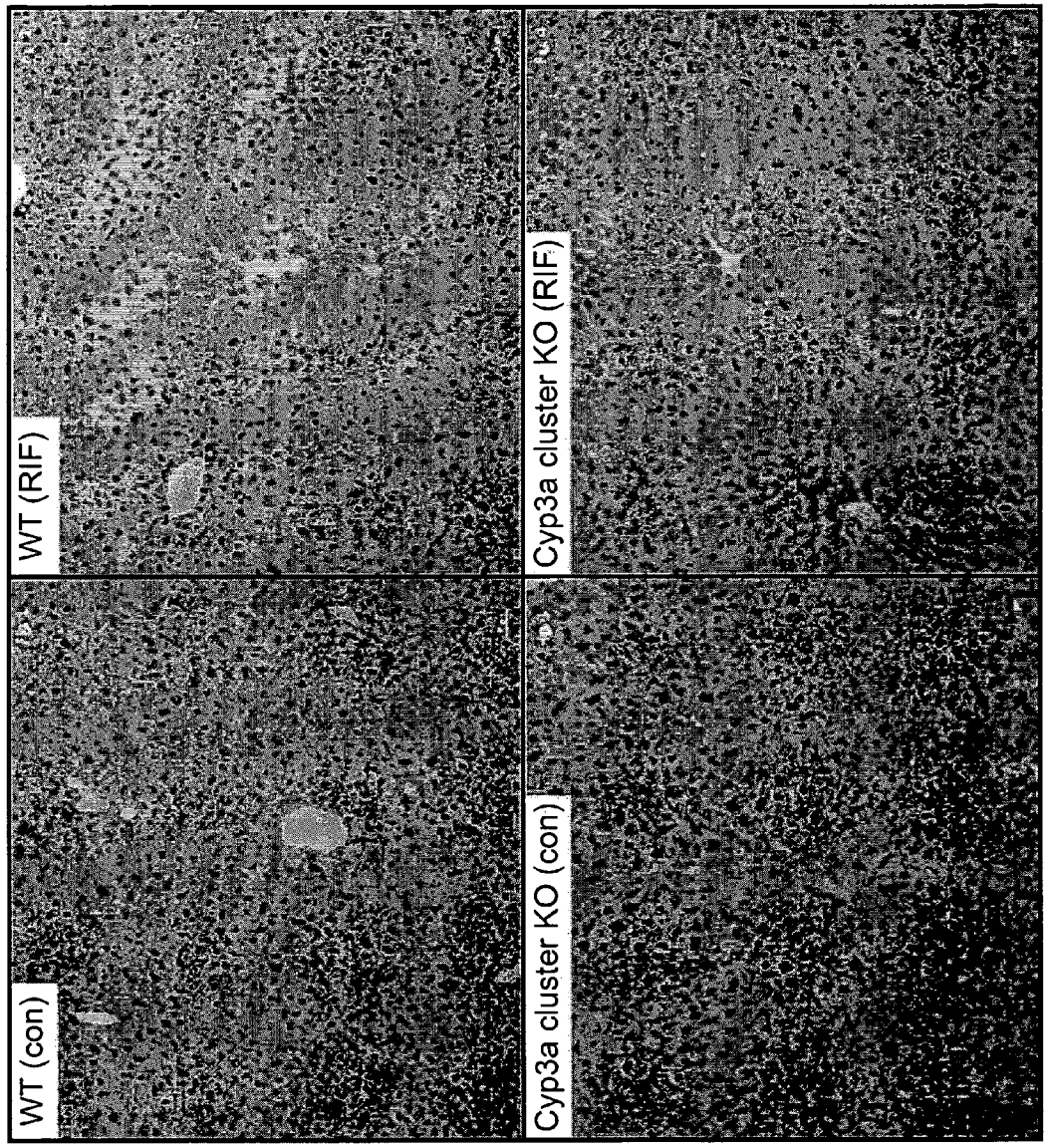

FIG. 1c: Haematoxylin and eosin staining of representative liver sections taken from control (Con) and rifampicin (RIF, 60 mg/kg, 3 days) treated C57BL/6J (WT) and Cyp3a cluster KO mice. 20× objective lens was used to capture image from Cyp3a cluster KO (Con). For all other images 10× objective lens was used.

Figure 1D:
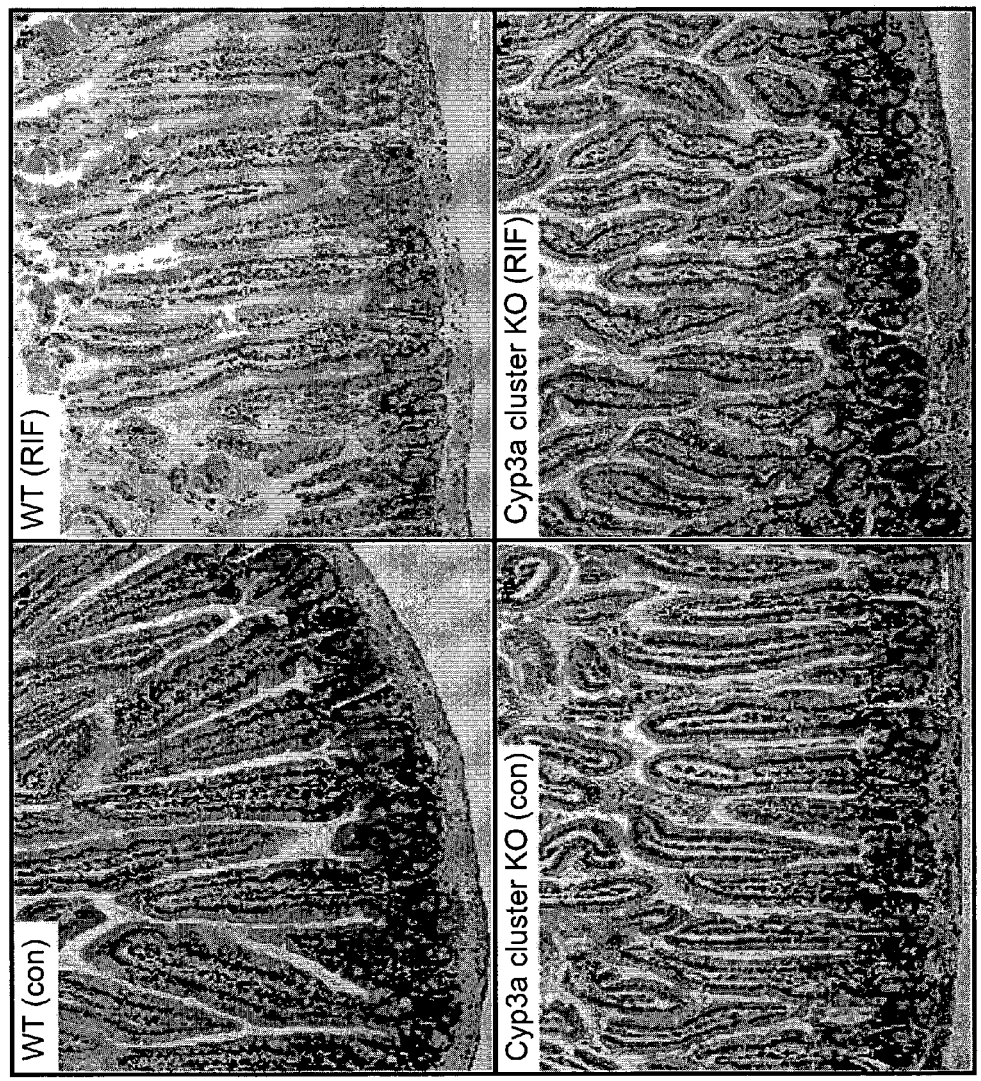

FIG. 1d: Haematoxylin and eosin staining of representative sections of small intestine taken from control (Con) and rifampicin (RIF, 60 mg/kg, 3 days) treated C57BL/6J (WT) and Cyp3a cluster KO mice. 10× objective lens was used to capture images.

Figure 1E:
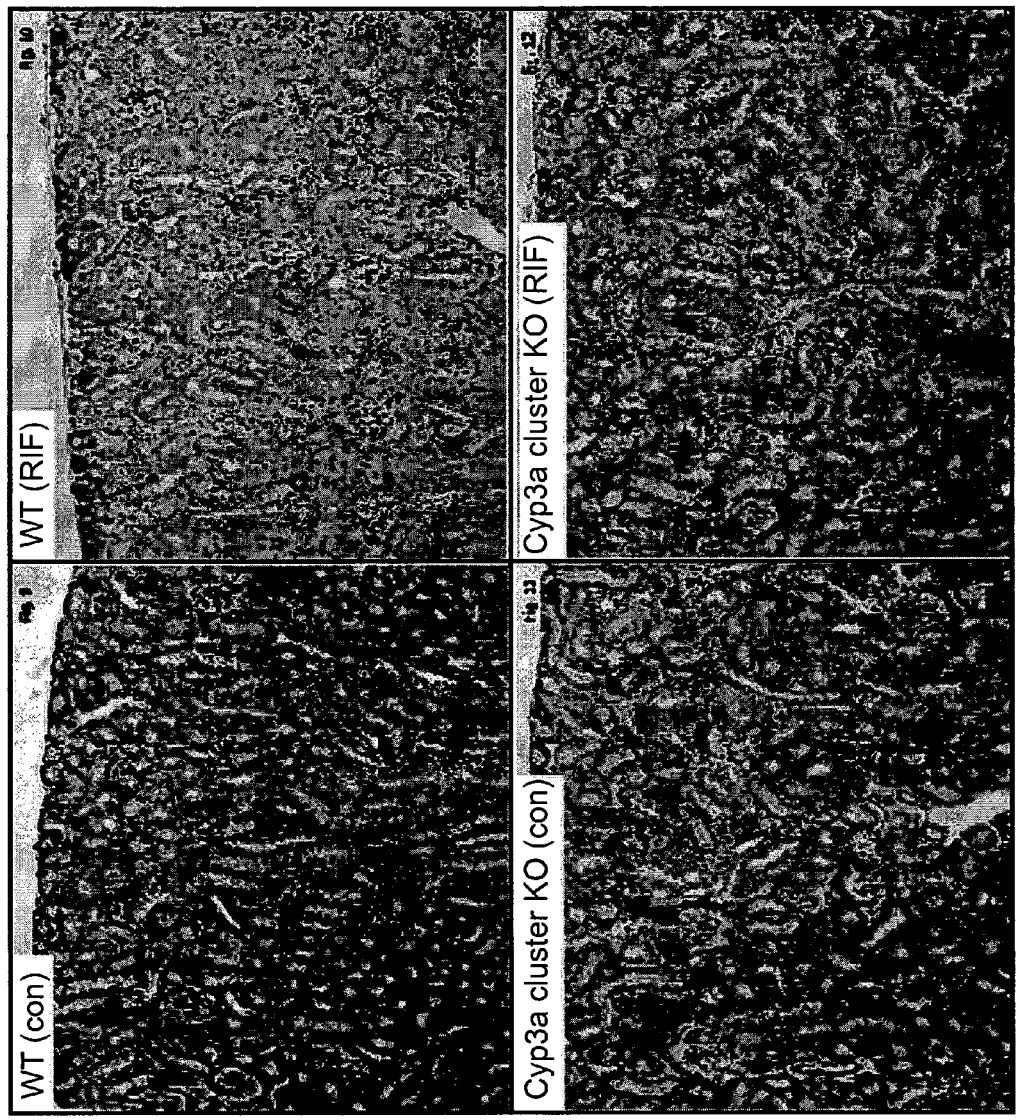

FIG. 1e: Haematoxylin and eosin staining of representative kidney sections taken from control (Con) and rifampicin (RIF, 60 mg/kg, 3 days) treated C57BL/6J (WT) and Cyp3a cluster KO mice. 10× objective lens was used to capture images.

Figure 1F:
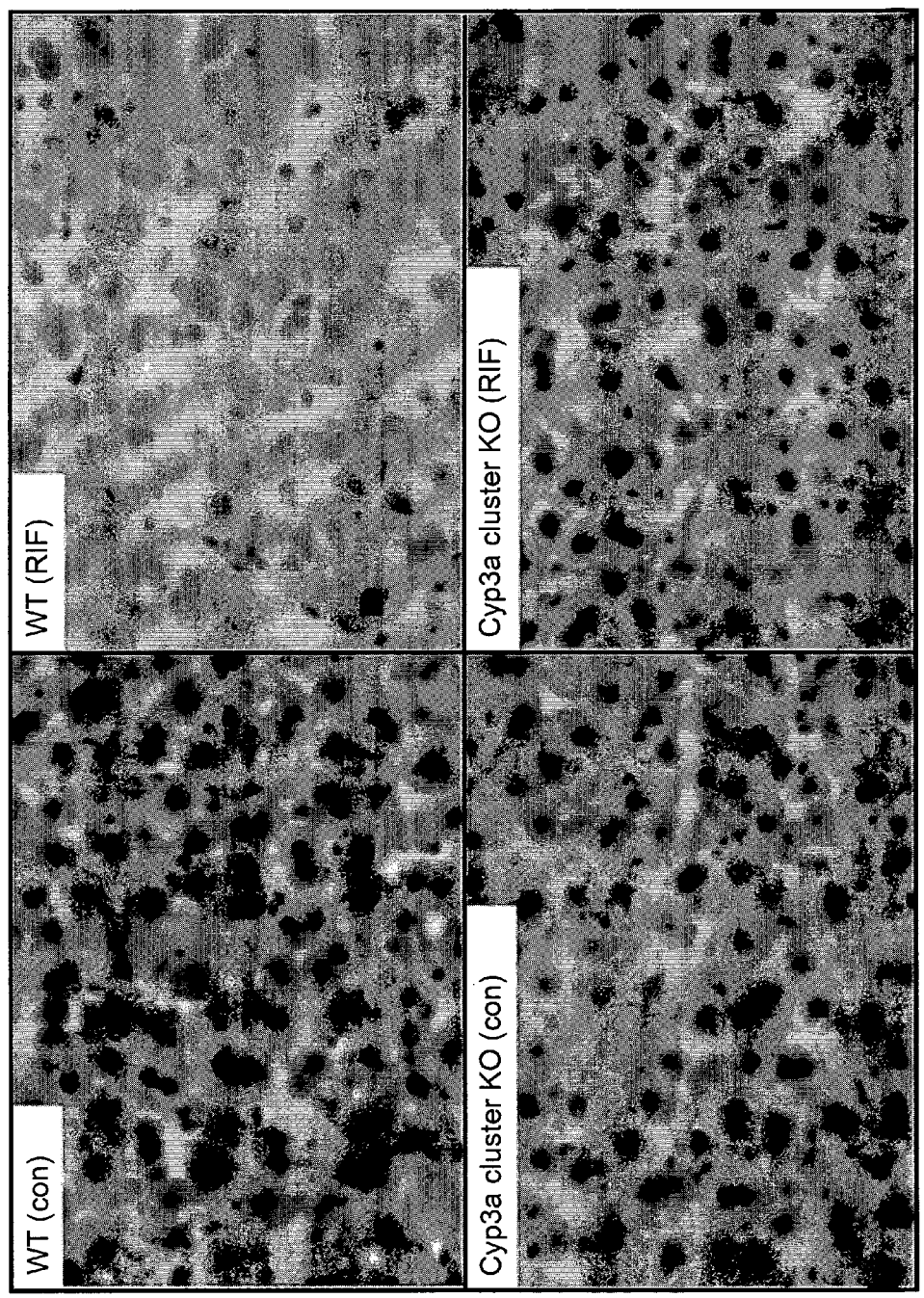

FIG. 1f: Oil Red O staining of representative liver sections taken from control (Con) and rifampicin (RIF, 60 mg/kg, 3 days) treated C57BL/6J (WT) and Cyp3a cluster KO mice. 40× objective lens was used to capture images.

Figure 1G:
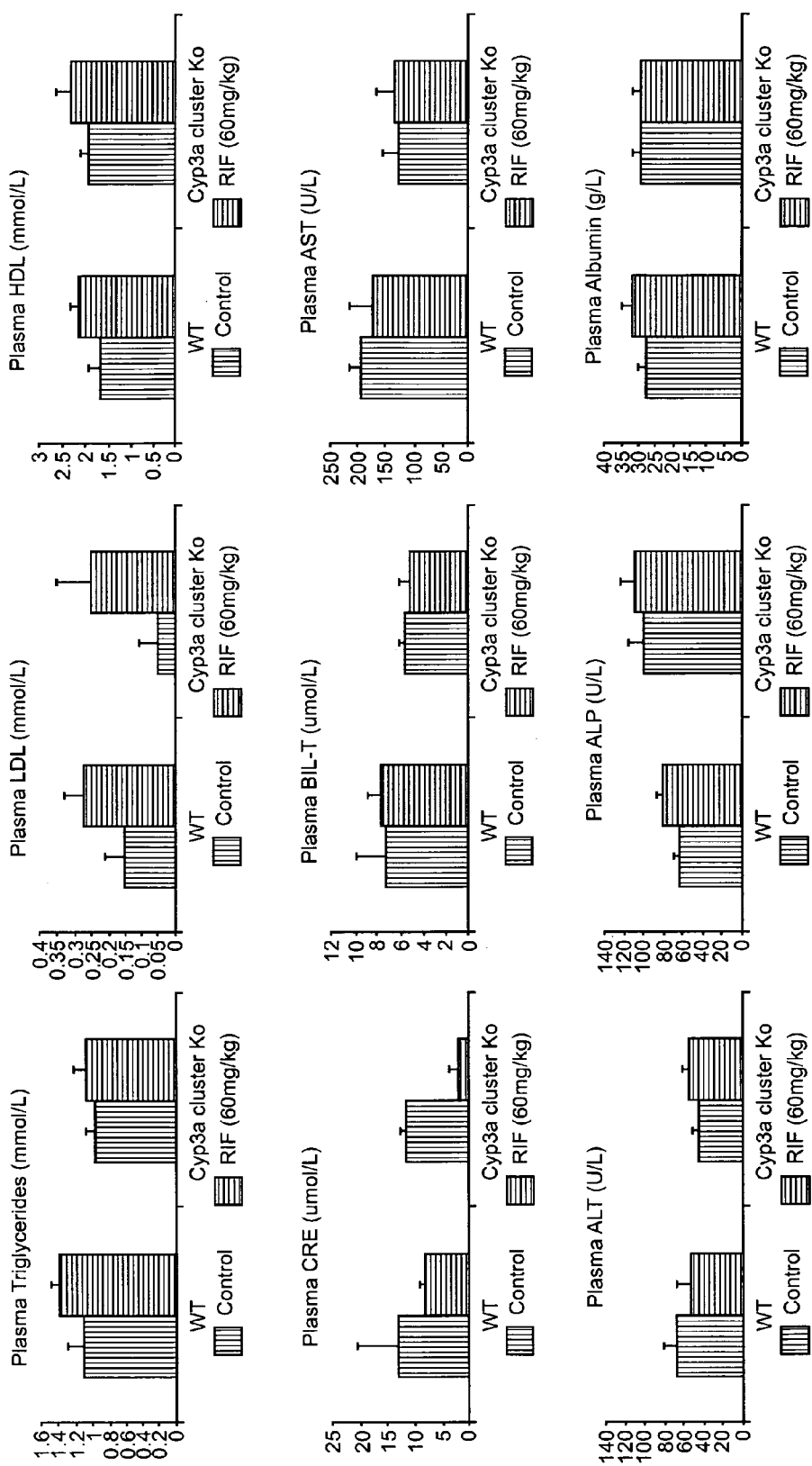

FIG. 1g: Clinical chemistry analysis of plasma from C57BL/6J and Cyp3a cluster KO control and rifampicin (60 mg/kg, 3 days) treated mice: triglycerides; low density lipoprotein (LDL), high density lipoprotein (HDL), creatine kinase (CRE), total bilirubin (BIL-T), aspartate aminotransferase (AST), alanine transferase (ALT), alkaline phosphatase (ALP), albumin. Data shown are mean±S.D. (n=4).

Figure 1H:
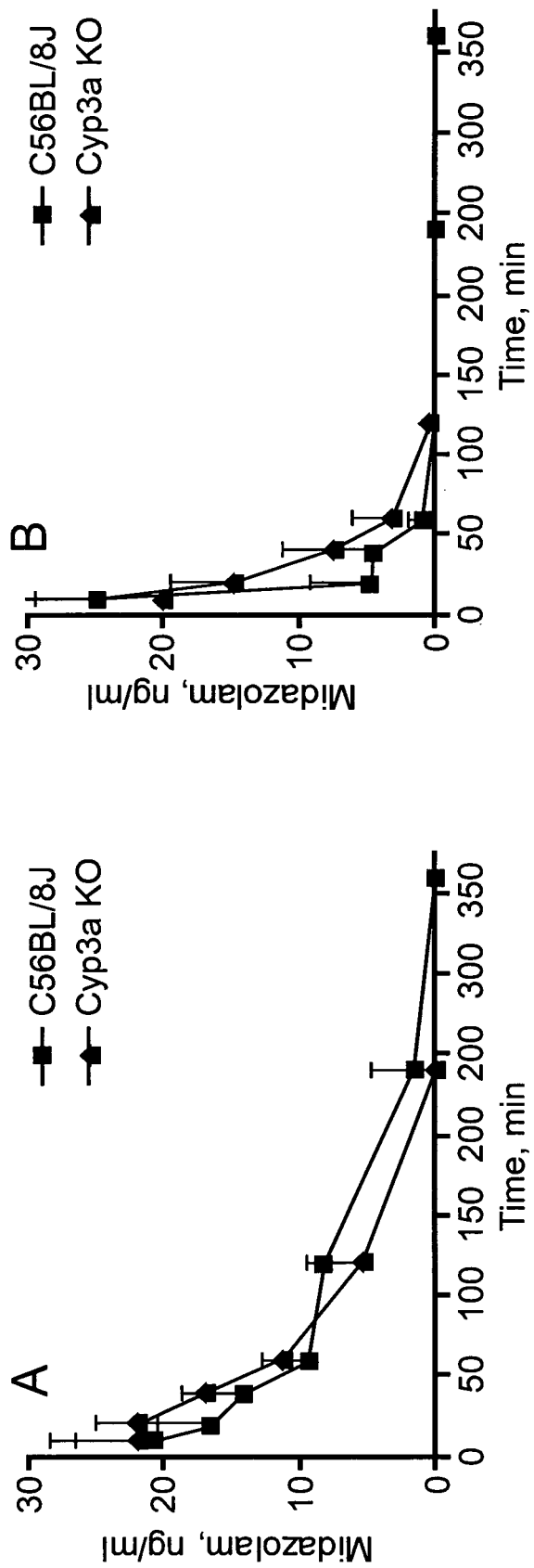

FIG. 1h: Midazolam (1 mg/kg) pharmacokinetics in wild type and Cyp3a cluster KO mice on Day 4 following treatment with corn oil (3 daily doses) (A) or rifampicin (60 mg/kg, 3 daily doses) (B); error bars represent SD. N.B.: SD for 10 min point of rifampicin treated C57BL/6J mice was 45 ng/mL. The corresponding error bar was only partially shown in order to retain graphs A and B on the same scale.

Figure 1J:
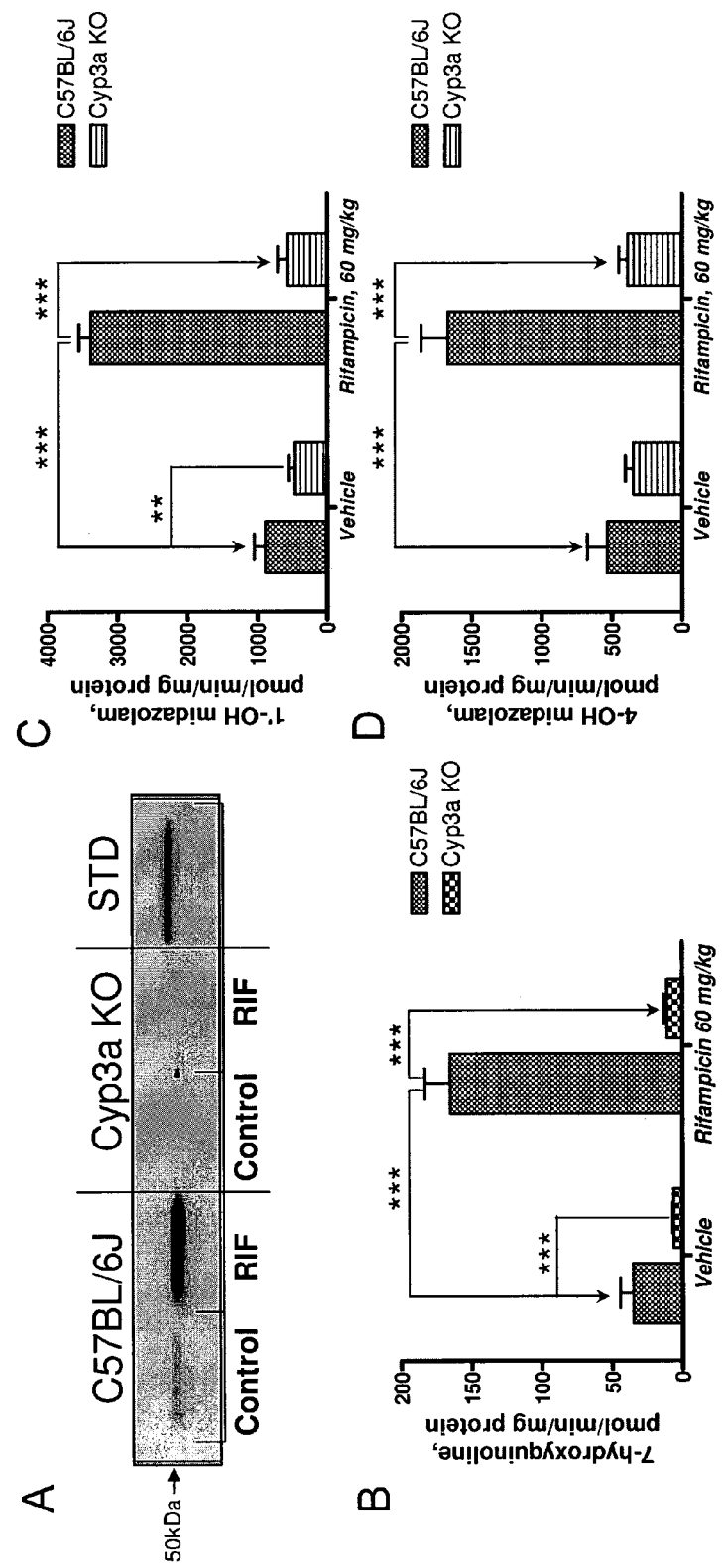
Figure 1K:
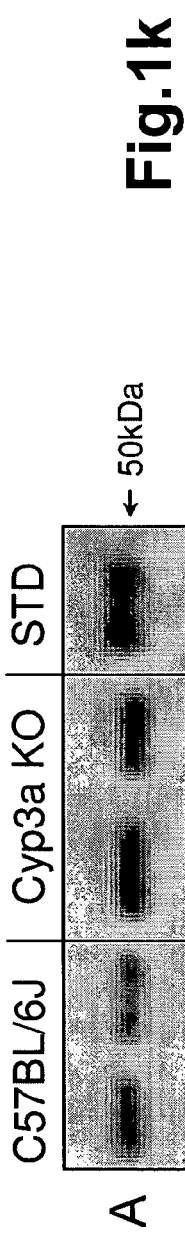
Figure 1K:
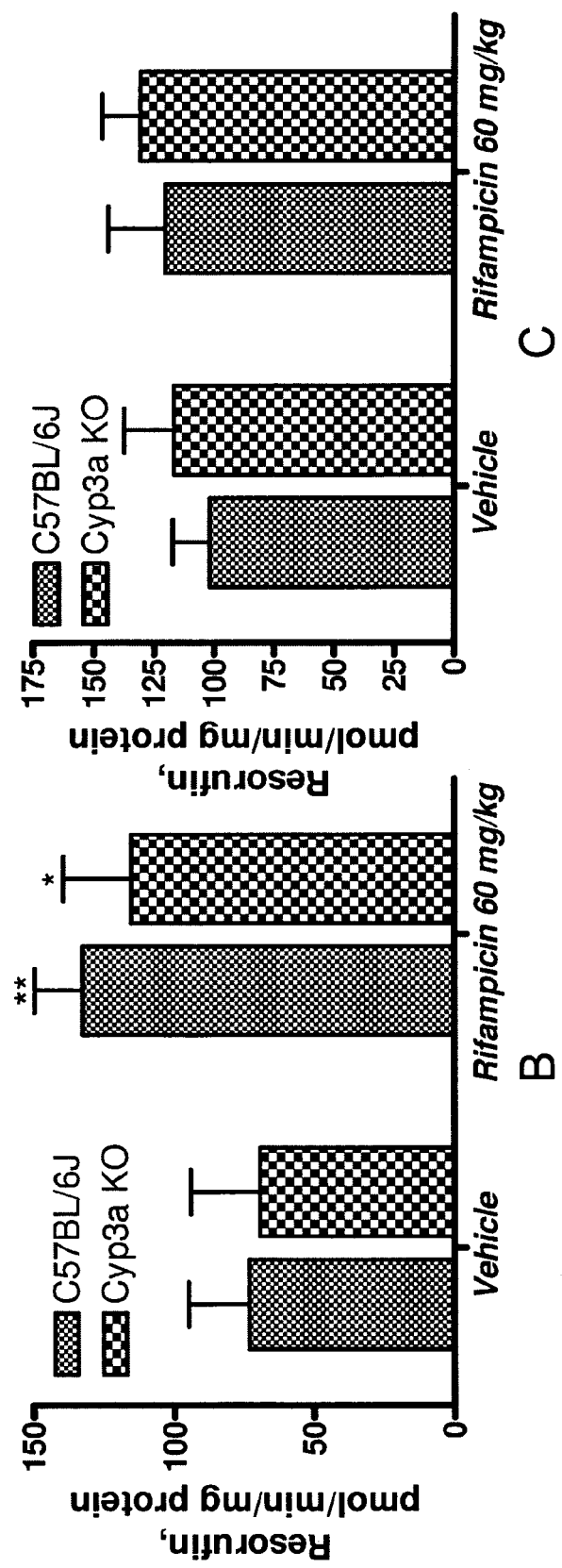
Figure 1I:
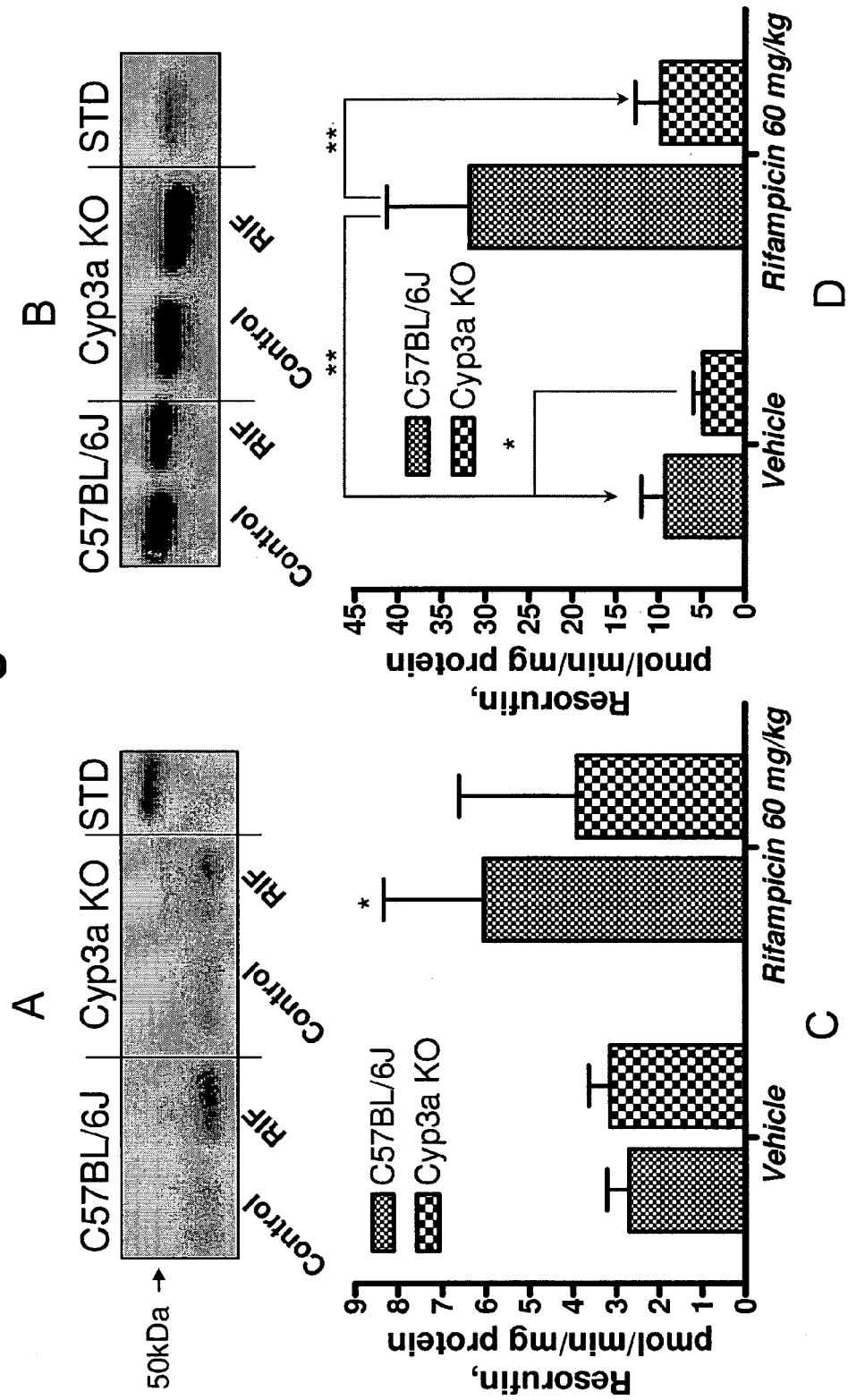

FIG. 1i: Total areas under the concentration/time curve (AUC) calculated from the midazolam PK using non-compartmental analysis of WinNonlin software.

FIG. 1j: Expression and activities Cyp3a isoforms in C57BL/6J and Cyp3a cluster KO mice. A) Western blotting; 1 μg of protein from liver microsomes was added to a 7.5% SDS page gel. The positive control was 0.1 pmol of Cyp3a11 recombinant protein (his-tagged) from CXR Biosciences. The primary antibody was rabbit anti-CYP3A2 (Colin Henderson, Ninewells Hospital, Dundee) used at a concentration of 1:2000. B) Oxidation of 7-BQ; C) 1'-hydroxylation and D) 4-hydroxylation of midazolam. Data are mean±SD (n=4). Activities were compared with an unpaired t test (two tailed P values); *-Significantly different (-P<0.01; *-P<0.001).

FIG. 1k: Cyp1a protein expression and activity in liver microsomes from vehicle (Control) and rifampicin (RIF; 60 mg/kg, 3 daily doses) treated C57BL/6J and Cyp3a cluster KO mice. (A)—Western blotting; 2 μg of protein from liver microsomes was added to a 7.5% SDS page gel. The positive control was 0.1 pmol of Cyp1a1 recombinant protein from CXR Biosciences. The primary antibody was goat anti-Cyp1a1/1a2 (BD Gentest, cat#458131) used at a concentration of 1:2000;

(B)—Ethoxyresorufin de-ethylation; (C)—methoxyresorufin de-methylation. Data are mean±SD (n=4). Activities were compared with an unpaired t test (two tailed P values); *-Significantly different from control (*-P<0.05; **-P<0.01)

FIG. 1l: Cyp2b protein expression in liver (A) and gut (B) microsomes from vehicle (Control) and rifampicin (RIF; 60 mg/kg, 3 daily doses) treated C57BL/6J and Cyp3a cluster KO mice. 2 μg of protein from liver and gut microsomes was added to a 7.5% SDS page gel. The positive control was 0.01 pmol of Cyp2b20 recombinant protein (his-tagged) from CXR Biosciences. The primary antibody was rabbit anti-Cyp2b (Colin Henderson, Ninewells Hospital, Dundee) used at a concentration of 1:2000. (C)—Pentoxyresorufin depentylation. (D)—Benzoxyresorufin debenzylation. Data are mean±SD (n=4). Activities were compared with an unpaired t test (two tailed P values); *-Significantly different from control (*-P<0.05)

Figure 1M:
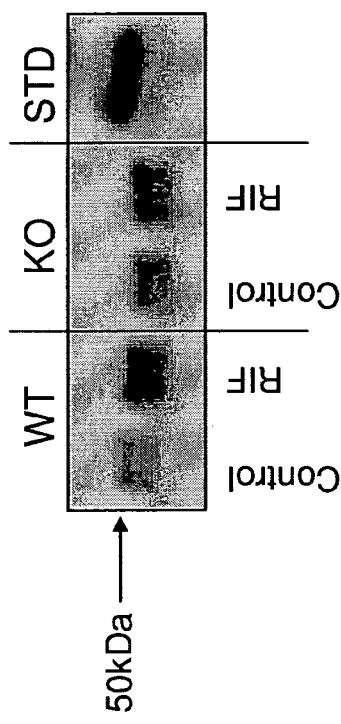

FIG. 1m: Cyp2c protein expression in liver microsomes from vehicle (Control) and rifampicin (RIF; 60 mg/kg, 3 daily doses) treated C57BL/6J (WT) and Cyp3a cluster KO (KO) mice. 2 µg of protein from liver microsomes was added to a 7.5% SDS page gel. The positive control was Cyp2c29 (0.5 pmol) recombinant protein from CXR Biosciences. The primary antibody was rabbit anti-Cyp2c (Colin Henderson, Ninewells Hospital, Dundee) used at a concentration of 1:50,000.

Figure 1N:
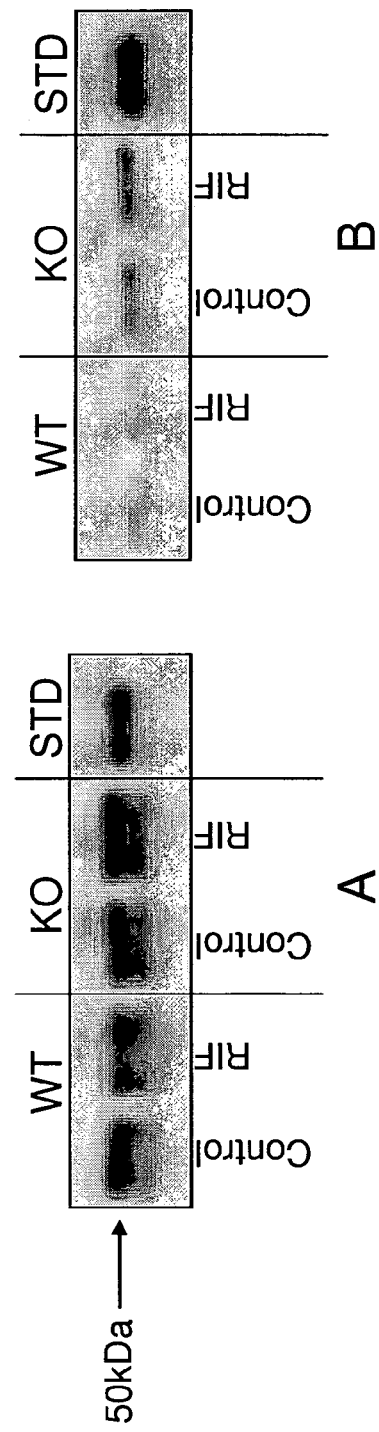

FIG. 1n: Liver (A) and gut (B) microsomes from vehicle (Control) and rifampicin (RIF; 60 mg/kg, 3 daily doses) treated C57BL/6J (WT) and Cyp3a cluster KO (KO) mice. 2 µg of protein from liver and gut microsomes was added to a 7.5% SDS page gel. The positive control was recombinant Cyp2d22 (0.2 pmol) from CXR Biosciences. The primary antibody was sheep anti-Cyp2d (Colin Henderson, Ninewells Hospital, Dundee) used at a concentration of 1:20,000.

FIG. 1o: Cyp2e expression in liver (A) and intestinal (B) microsomes from vehicle (Control) and rifampicin (RIF; 60 mg/kg 3 daily doses) treated C57BL/6J (WT) and Cyp3a cluster KO (KO) mice. 2 µg of protein from liver and gut microsomes was added to a 7.5% SDS page gel. The positive control was 0.2 pmol of Cyp2e1 recombinant protein from CXR Biosciences. The primary antibody was sheep anti-Cyp2e (SAPU BRC) used at a concentration of 1:4000.

FIG. 1p: Cyp4a protein expression in liver microsomes from vehicle (Control) and rifampicin (RIF; 60 mg/kg, 3 daily doses) treated C57BL/6J and Cyp3a cluster KO mice. 2 µg of protein from liver microsomes was added to a 7.5% SDS page gel. The positive control was 1 µg of APFO induced rat microsomes from CXR Biosciences. The primary antibody as rabbit anti-Cyp4a (Colin Henderson, Ninewells Hospital, Dundee) used at a concentration of 1:20,000.

FIG. 1q: (A) P450 oxidoreductase protein expression in liver microsomes from vehicle (Control) and rifampicin (RIF; 60 mg/kg, 3 daily doses) treated C57BL/6J (WT) and Cyp3a cluster KO mice (KO). 2 µg of protein from liver microsomes was added to a 7.5% SDS page gel. The positive control 3 µg of male human liver microsomes (pooled) from BD Gentest (cat #452172). The primary antibody was rabbit anti-P450 reductase (CXR Biosciences) used at a concentration of 1:5000. (B)—Cytochrome C reductase activity in mouse liver microsomes from C57BL/6J and Cyp3a cluster KO mice. Data shown are mean±SD (n=3 for C57BL/6J and n=4 for Cyp3a cluster KO).

FIG. 1r: Total P450 content in liver microsomes from vehicle and rifampicin (60 mg/kg, 3 daily doses) treated C57BL/6J and Cyp3a cluster KO mice. Data are mean±SD (n=4). Activities were compared with an unpaired t test (two tailed P values); *-Significantly different from control (*-P<0.05; -P<0.01; *-P<0.001)

Figure 1S:
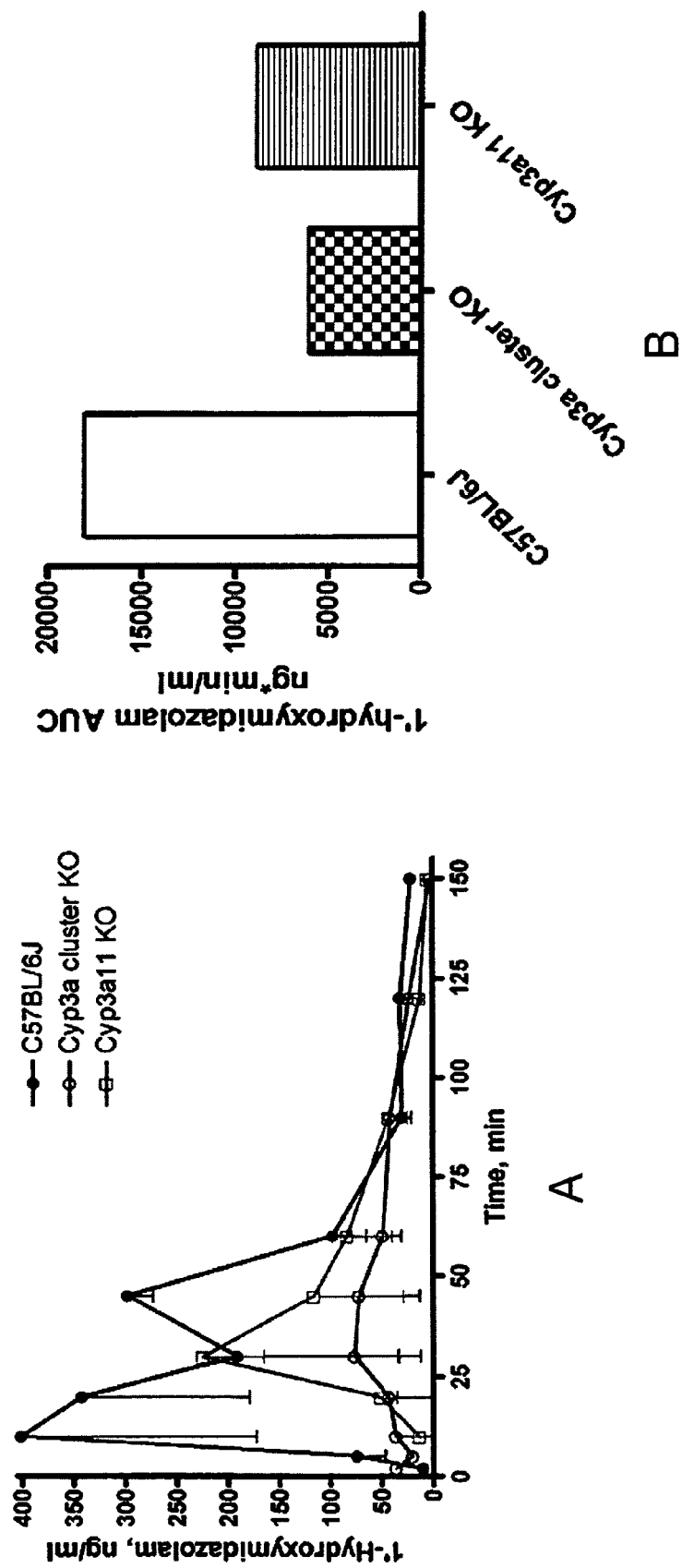
Figure 1T:
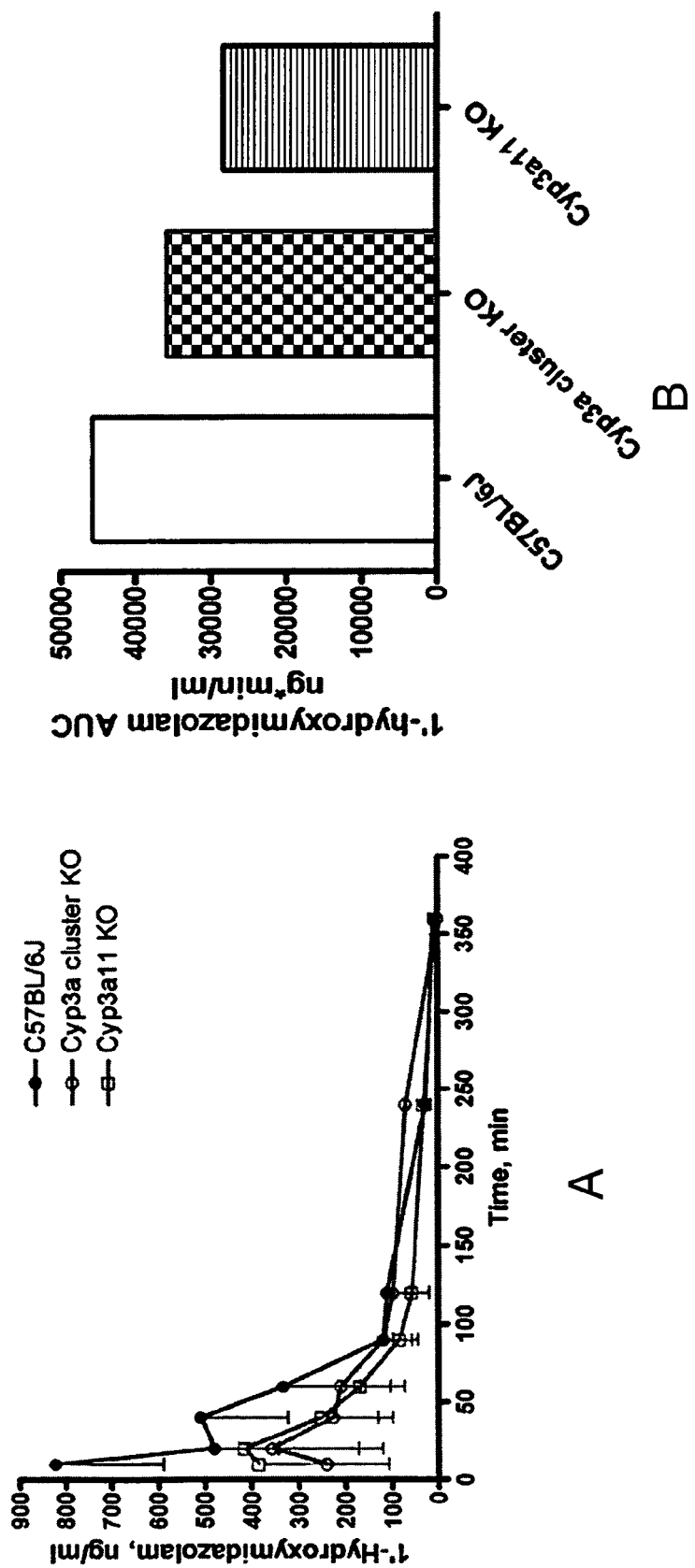
Figure 1U:
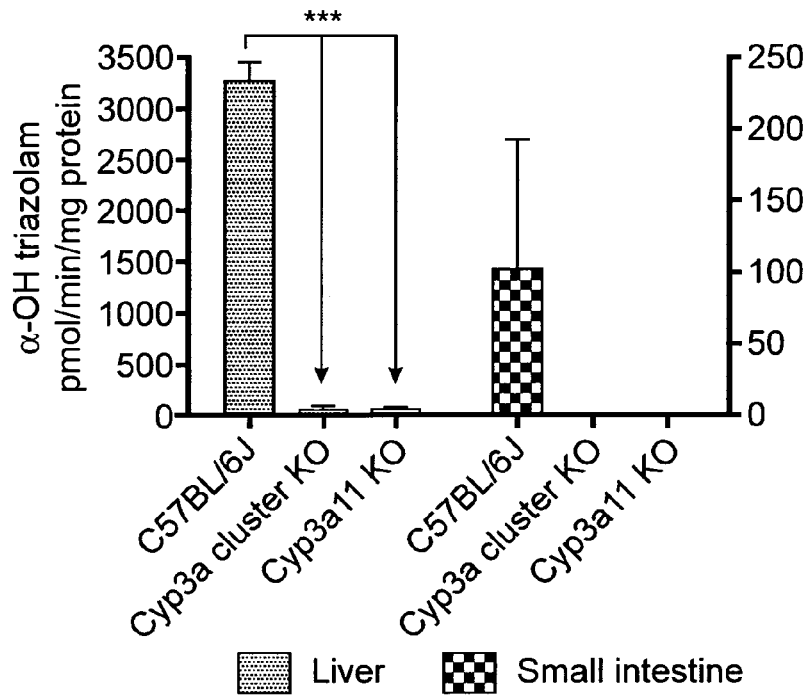

FIG. 1s: (A)-1'-Hydroxymidazolam pharmacokinetics in wild type, Cyp3a cluster KO and Cyp3a11 KO mice after IV administration of midazolam (1 mg/kg) on Day 4 following treatment with rifampicin (60 mg/kg, 3 daily doses); error bars represent SD. (B) Area Under the Curve (AUC) calculated from 1'-hydroxymidazolam PK FIG. 1t: 1'-Hydroxymidazolam pharmacokinetics in wild type, Cyp3a cluster KO and Cyp3a11 KO mice after oral administration of midazolam (2 mg/kg) on Day 4 following treatment with rifampicin (60 mg/kg, 3 daily doses); error bars represent SD. (B) Areas Under the Curve (AUC) calculated from 1'-hydroxymidazolam PK FIG. 1u: α-Hydroxylation of triazolam by liver and intestinal microsomes from C57BL/6J, Cyp3a cluster KO and Cyp3a11 KO mice. Data are mean+SD (n=4 for C57BL16J and Cyp3a11 KO liver microsomes; n:3 for Cyp3a cluster KO liver microsomes and C57BL/6J intestinal microsomes). Activities were compared with an unpaired t test (two tailed P values); *-Significantly different (***<P<0.001) Activities of Cyp3a cluster KO and Cyp3a11 KO intestinal microsomes were below the Lower limit of quantification.

Figure 1V:
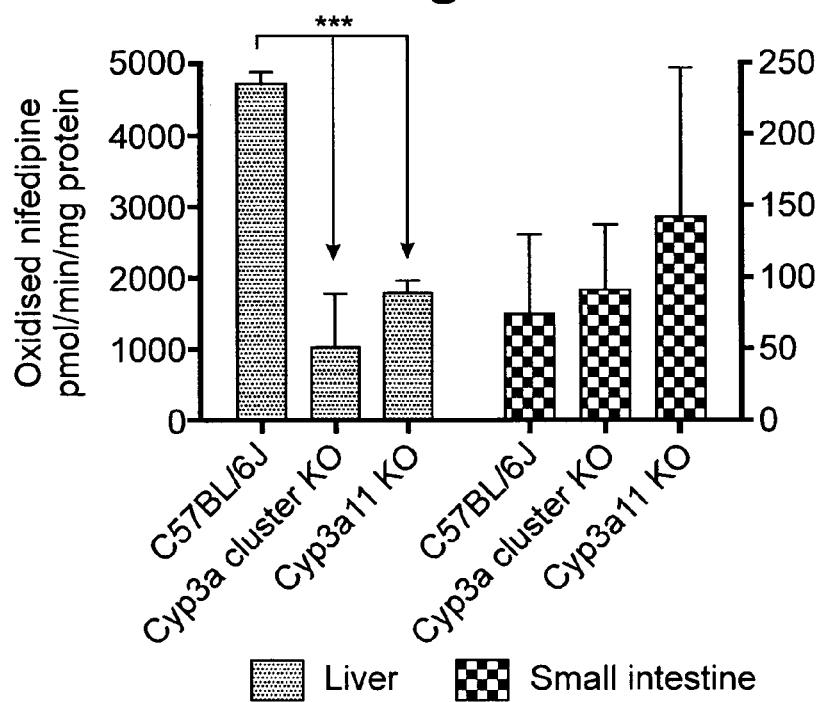

FIG. 1v: Nifedipine oxidation by liver and intestinal microsomes from C57Bl16J, Cyp3a cluster KO and Cyp3a11 KO mice. Data are mean±SD (n:4 for C57BL16J and Cyp3a11 KO microsomes; n:3 for Cyp3a cluster KO). Activities were compared with an unpaired t test (two tailed P values); *-Significantly different (***-P<0.001)

Figure 1W:
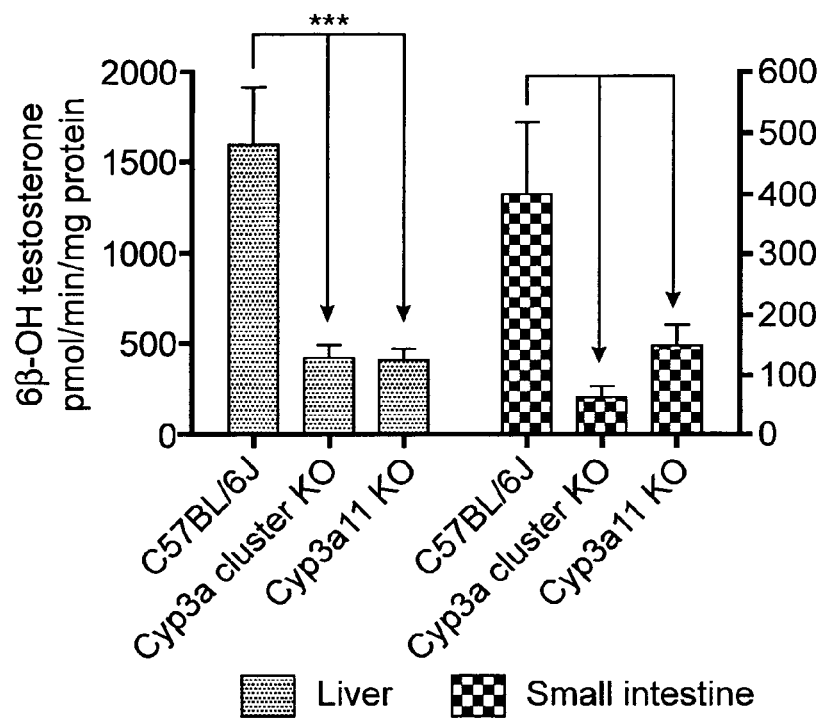

FIG. 1w: 6β-Hydroxylation of testosterone by liver and intestinal microsomes from C57BL|6J, Cyp3a cluster KO and Cyp3a11 KO mice. Data are mean±SD (n:4 for liver microsomes and n:3 for the intestinal microsomes). Activities were compared with an unpaired t test (two tailed P values); *-Significantly different (***-P<0.001. x*, -p<0.01)

Figure 1X:
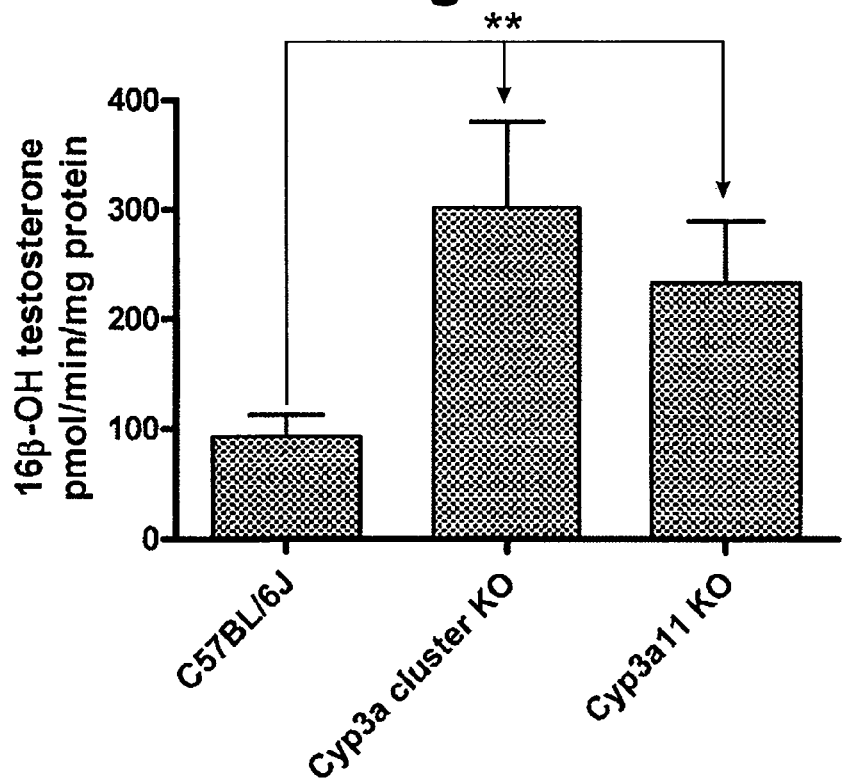

FIG. 1x: 16β(3-Hydroxylation of testosterone by Liver microsomes from C57BL16J, Cyp3a cluster KO and Cyp3a11 KO mice. Data are mean±SD (n=4). Activities were compared with an unpaired t test (two tailed P values); *-Significantly different (x*-p<0.01)

Figure 1Y:
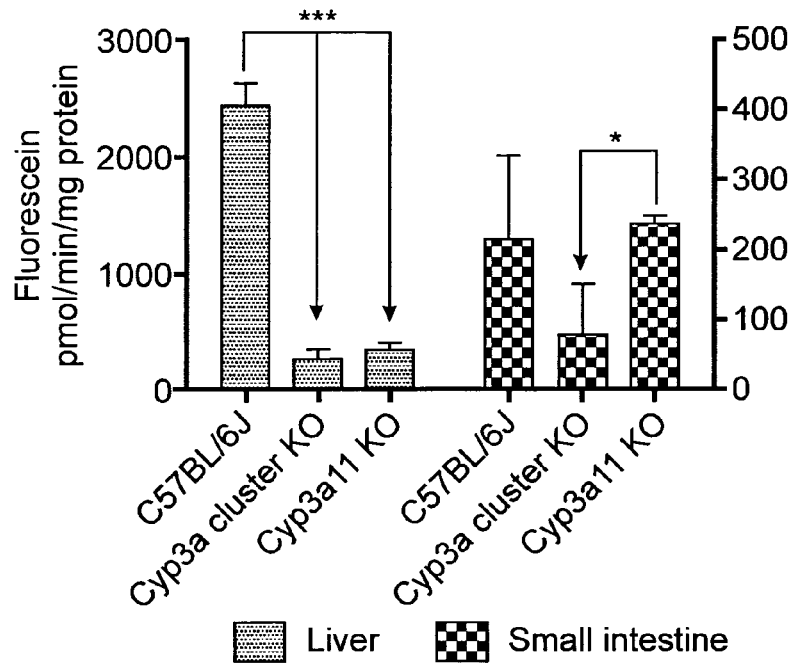

FIG. 1y: Oxidation of DBF by liver and intestinal microsomes from C57BL/6J, Cyp3a cluster. KO and Cyp3a11 KO mice. Data are mean t SD (n=4 liver and n=3 for intestinal microsomes). Activities were compared with an unpaired t test (two tailed P values); *-Significantly different (**x-P<0.001; *-P<0.05)

Figure 1Z:
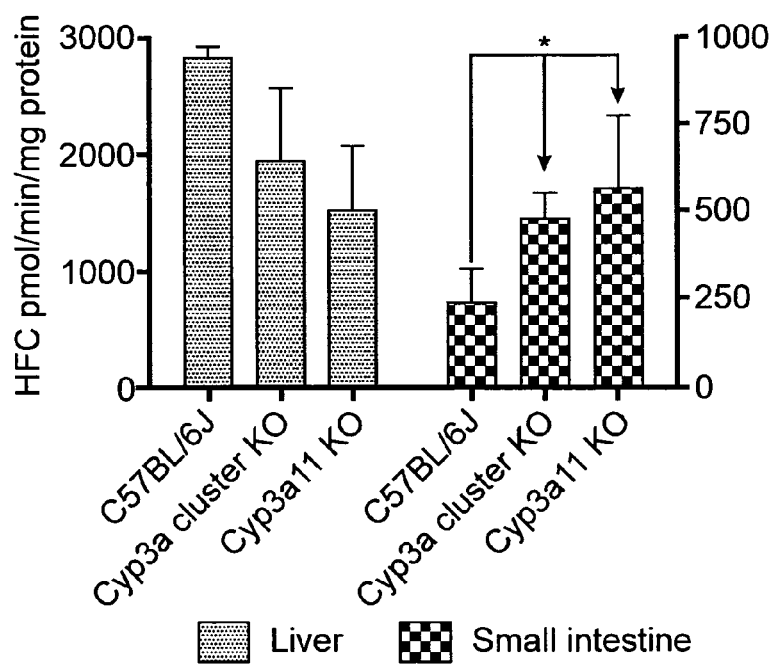

FIG. 1z: Oxidation of BFC by liver and intestinal microsomes from C57BL/6J, Cyp3a cluster KO and Cyp3a11 KO mice. Data are mean+/−SD (n:4 for liver microsomes; for intestinal microsomes n:4 for C57BL/6J; n=3 for Cyp3a1 1 KO and n:2 for Cyp3a cluster KO). Activities were compared with an unpaired t test (two tailed P values); *-Significantly different (*-P<0.05)

Figure 2A:
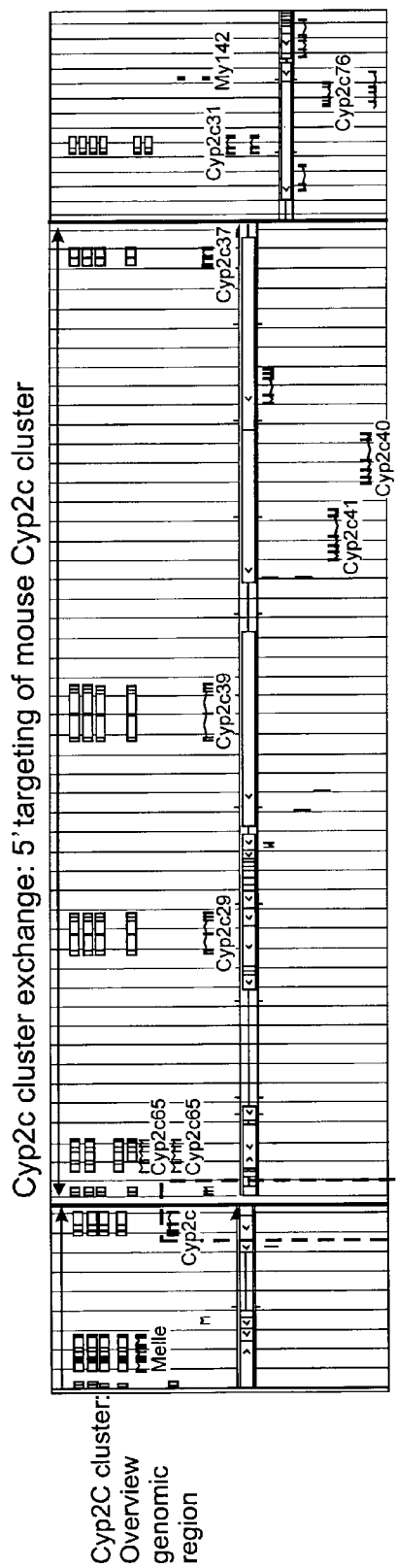
Figure 2A:
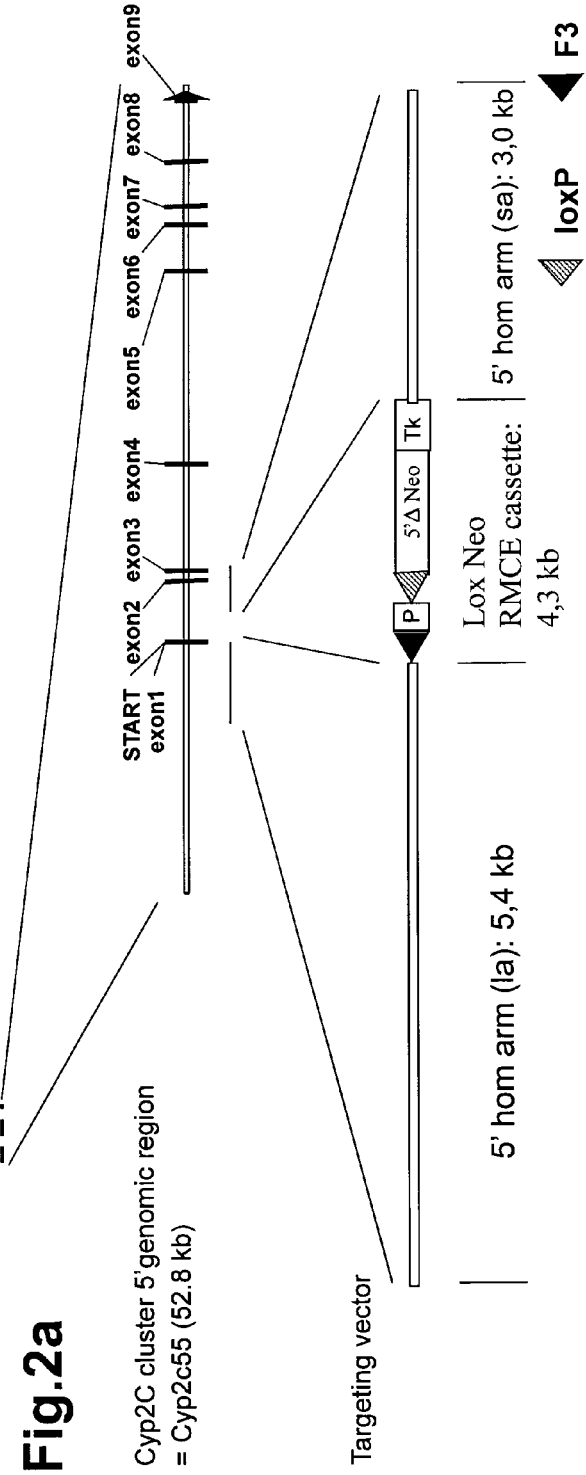
Figure 2B:
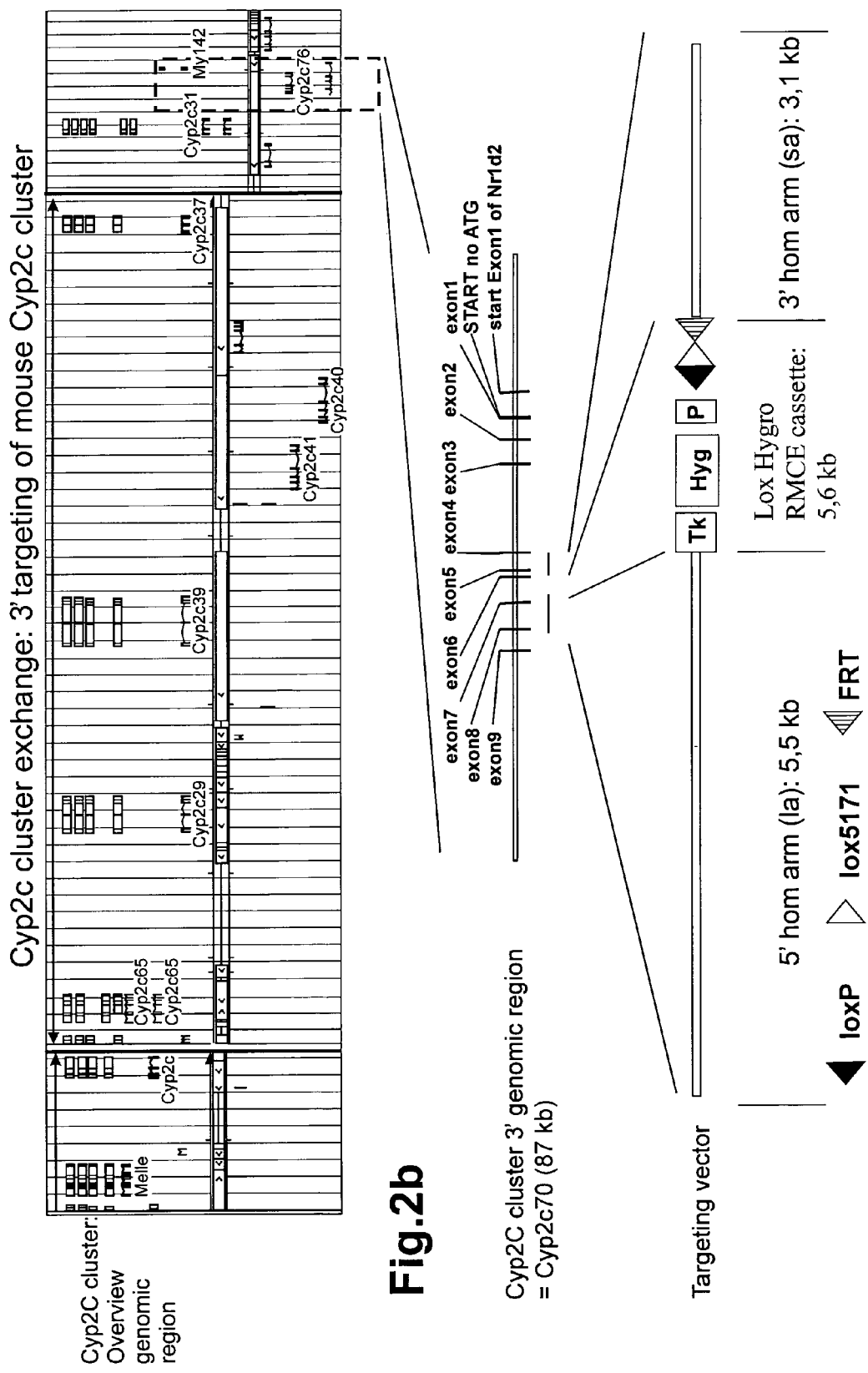

FIGS. 2a-2c depict the methodology for the Cyp2c cluster exchange. A) 5' targeting of mouse Cyp2c cluster; B) 3' targeting of mouse Cyp2c cluster; C) Overview: Cyp2c cluster knockout; D) PCR confirmation of absence of mouse Cyp3a cluster from genome in mouse ID 234254; (E) PCR confirmation of the absence of the mouse 3a cluster from the genome in mouse ID 234254.

Figure 2D:
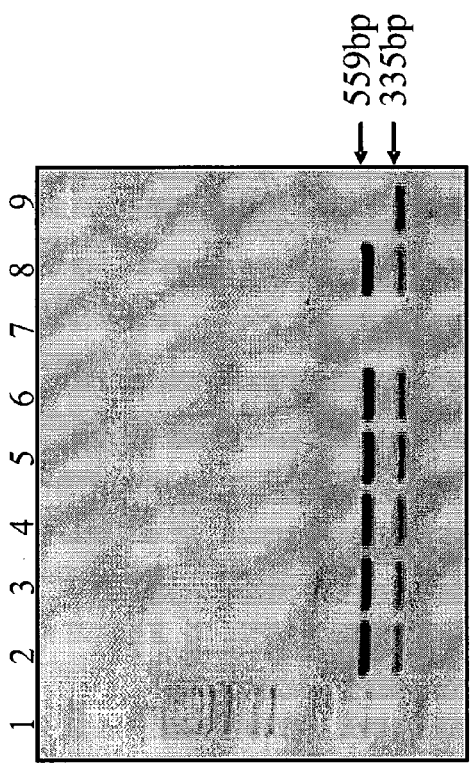
Figure 2D:
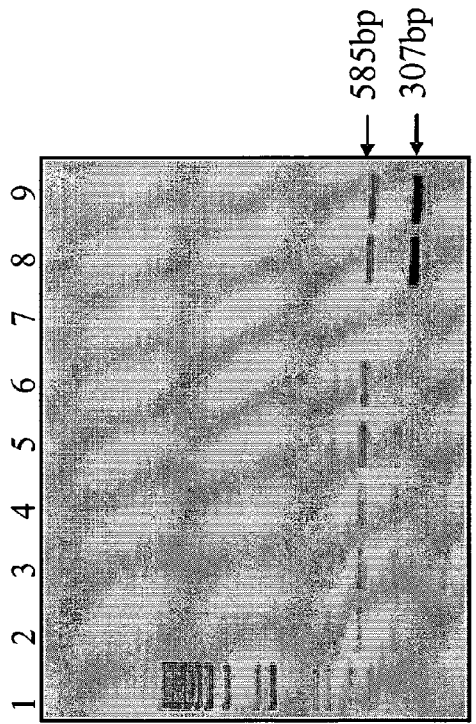

FIG. 2d: PCR confirmation of a mouse homozygous for Cyp2c cluster deletion

Figure 2E:
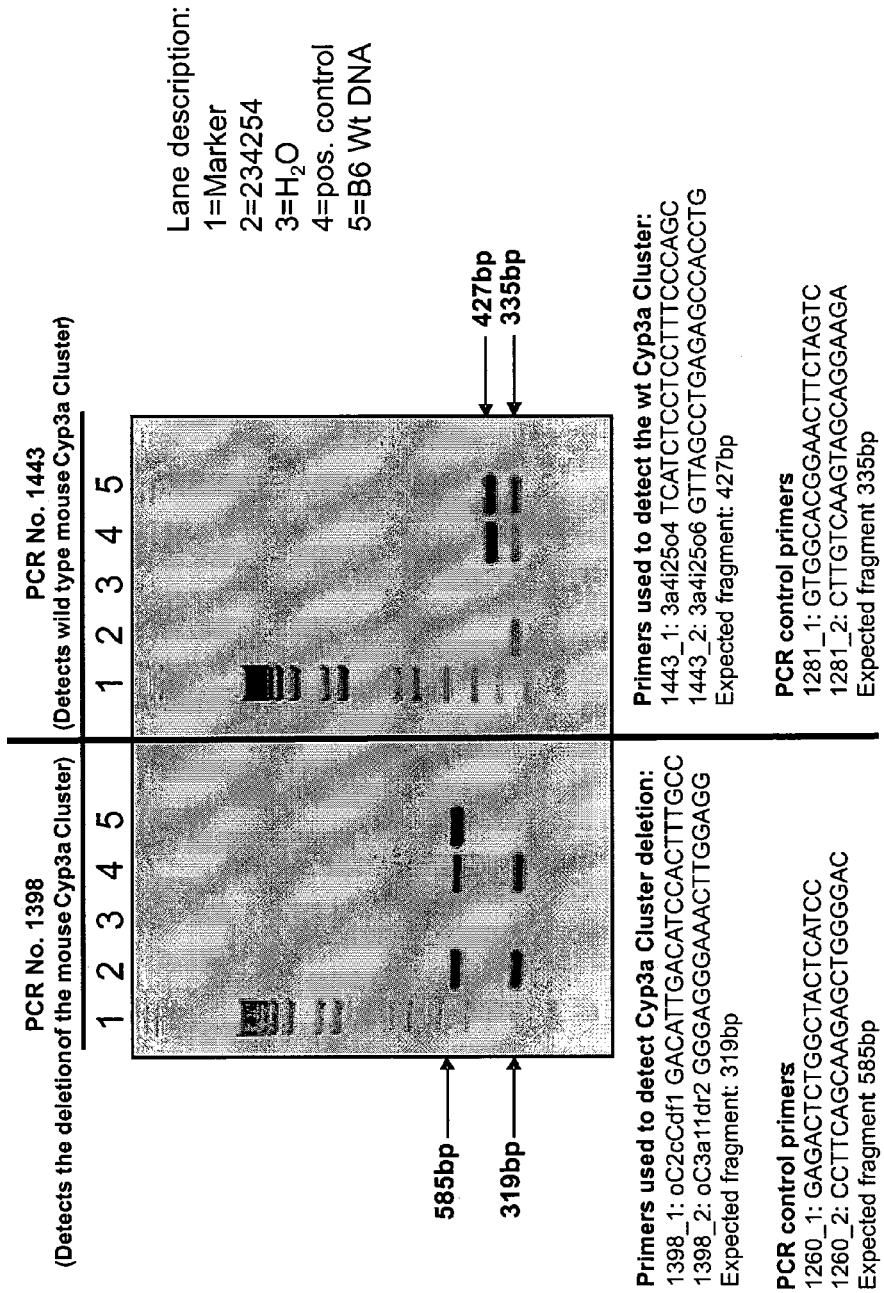

FIGS. 2e-2f: PCR confirmation of construction of Cyp3a/Cyp2s multiple cluster KO strain.

Figure 3B:
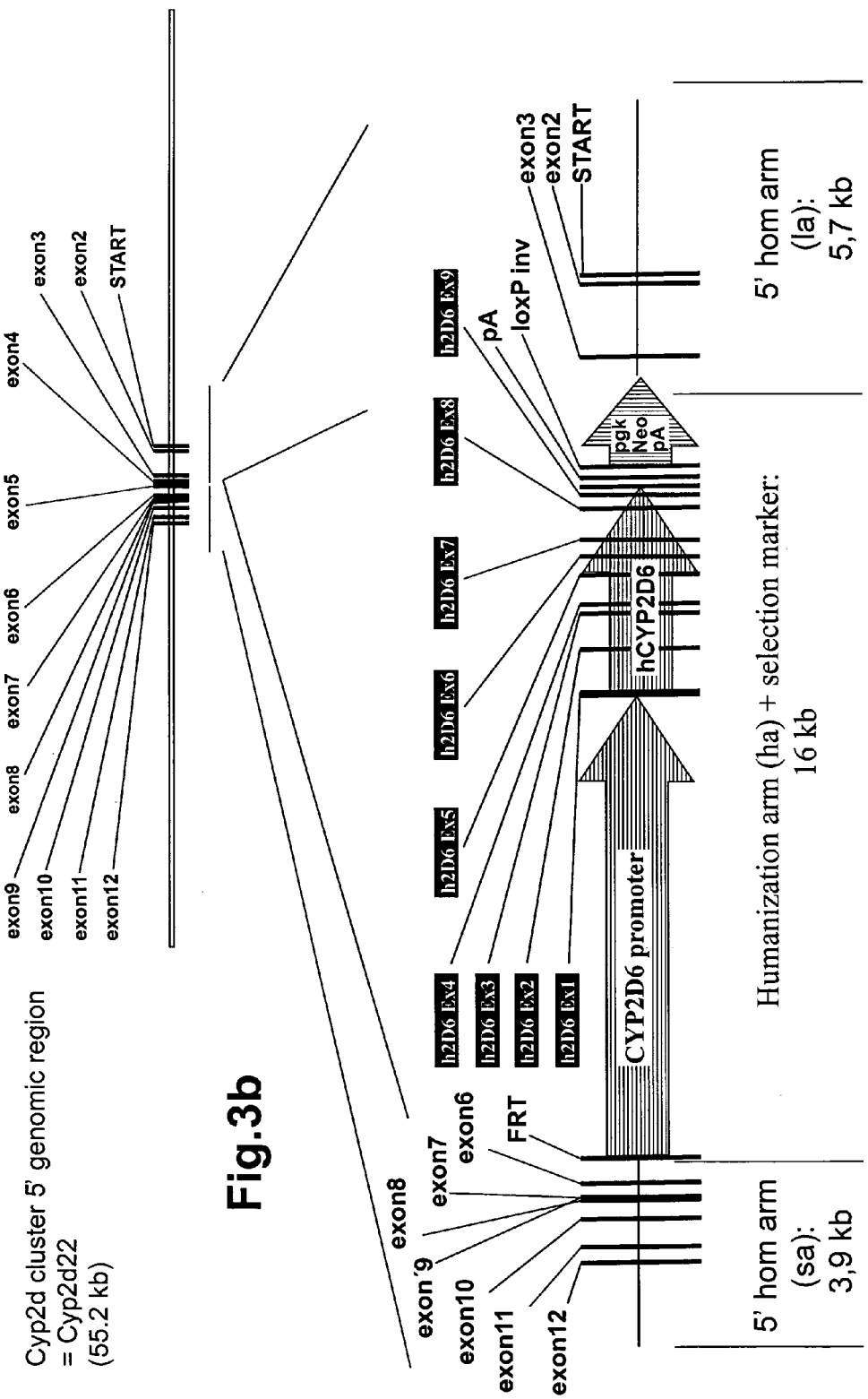

FIGS. 3a-3c depict the methodology for the Cyp2d cluster exchange. A) 3' targeting of mouse Cyp2d26; B) 5' targeting of mouse Cyp2d cluster; C) Overview: Cyp2d knockout.

Figure 3D:
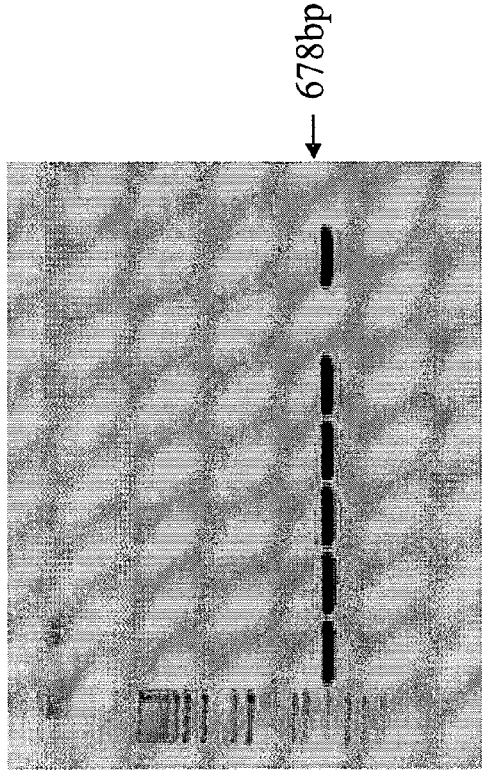
Figure 3D:
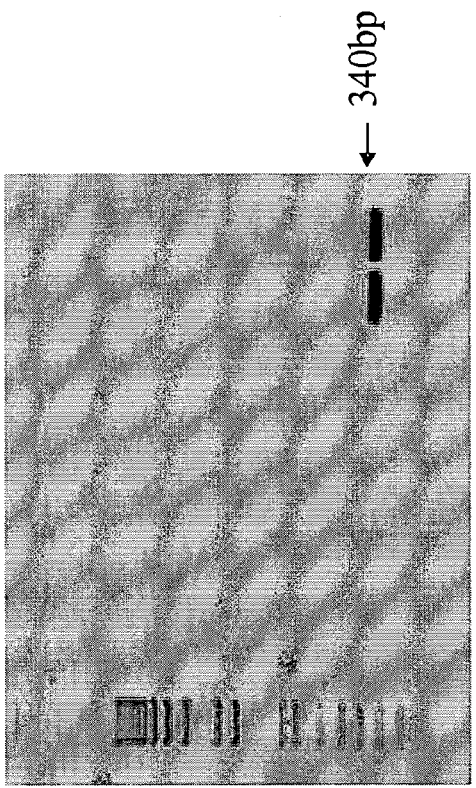

FIG. 3d: PCR confirmation of a mouse homozygous for Cyp2d cluster deletion

Figure 3E:
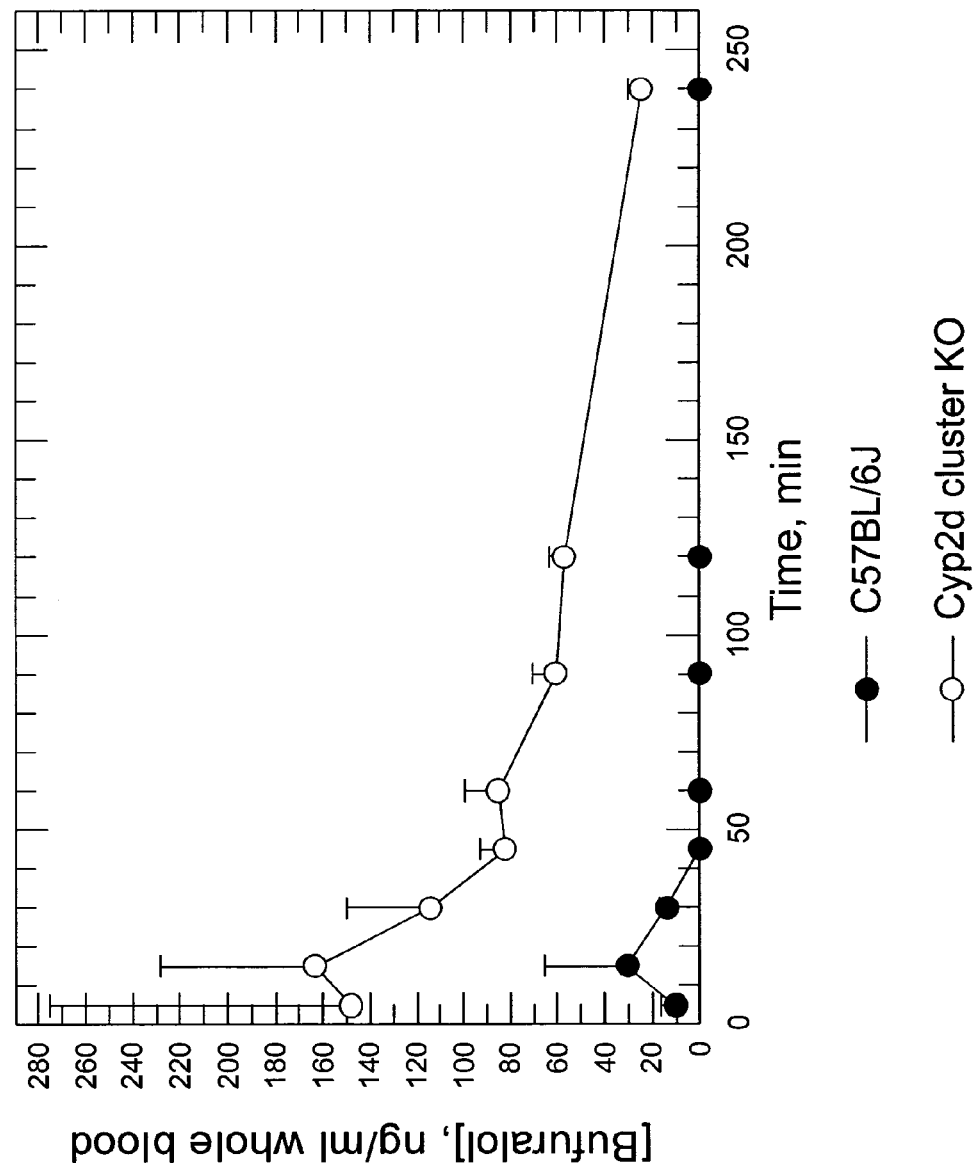

FIG. 3e: Pharmacokinetics of bufuralol (10 mg/kg, single oral dosing) in wild type, e.g. C75BL/6J, and Cyp2d cluster KO mice Data represents mean±SD (n=4) of concentration of bufuralol detected in whole blood up to 240 mins post administration.

FIG. 4 depicts the methodology for the CYP1A knockout. A) 5' targeting of mouse Cyp1a; B) 3' targeting of mouse Cyp1a; C) Overview: Cyp1a knockout.

EXAMPLES

Example 1

Cyp3a Cluster Exchange

The 5' end of the mouse Cyp3a cluster was targeted by homologous recombination, so that a frt, lox5171 and wildtype loxP site are inserted downstream of Exon1 of the Cyp3a57 gene as depicted in FIG. 1a. Furthermore, a hygromycin resistance and a thymidine kinase (TK) expression cassette were co-introduced as depicted.

Correctly-targeted ES cells were further modified by a subsequent step of homologous recombination at the 3' end of the mouse Cyp3a cluster, so that a wildtype loxP and a f3 site are inserted downstream of Exon4 of the Cyp3a59 gene. A 5' deficient neomycin resistance and a TK expression cassette were co-introduced as depicted in FIG. 1b. The translational start ATG is separated in frame from the 5' deficient neomycin resistance cassette by the loxP site, so that additional amino acids encoded by the loxP site are attached to the N-terminus of the neomycin protein.

To allow the deletion of the mouse Cyp3a cluster by Cre-mediated recombination, the targeting at both ends of the cluster has to be on the same allele. This was tested in vitro by transfection of double targeted ES cells with Cre and subsequent selection with Gancyclovir. Only in cells with targeting on the same allele will the TK genes be deleted at both ends of the cluster as depicted in FIG. 1e, so that the TK-mediated conversion of the nucleoside analog ganciclovir to a toxic triphospate analog is prevented. Therefore, only ES cells with targeting on the same allele survive the ganciclovir selection.

Surviving ES cell clones were further analysed by PCR to confirm that the mouse Cyp3a cluster was deleted and PCR-positive clones were injected into blastocysts to generate chimeric mice. By subsequent crosses mice with a homozygous deletion of the Cyp3a cluster were finally generated.

The remaining wildtype loxP and the lox5171 sites in the ES cells can in due course be used subsequently to insert replacement genes, e.g. the human CYP3A cluster, at the former position of the mouse cluster by Cre-mediated insertion. The remaining promoter, the ATG and in frame wildtype loxP site can be utilized to insert again a 5' deficient selection cassette, e.g. 5' deficient neomycin, to select for clones with correct insertion with high efficiency. The frt and f3 sites at both ends can be used to delete the selection cassettes introduced with the replacement genes by Flp-mediated deletion, provided that additional frt and f3 sites are co-introduced in the right orientation with the replacement cassette.

The Cyp3a13 gene which is located 800 bp upstream of Cyp3a57 and which is separated from the murine Cyp3a cluster by a number of Cyp-unrelated genes is not affected by the deletion of the mouse Cyp3a cluster described above.

FIG. 1b shows PCR confirmation of the absence of the mouse Cyp3a cluster from the genome in mice with the IDs 219678, 219679, 219680, 219681 and 219682

Analysis of Cyp3a Cluster KO Mice in Comparison to C57BL/6J

The study consisted of 4 groups with 4 animals per group. The mice received 3 daily intraperitoneal (IP) doses of rifampicin (60 mg/kg). On day 4 of the study midazolam (1 mg/kg) was administered by IP injection and 10 µL blood samples were collected at 10, 20, 40, 60, 120, 240 and 360 min for PK analysis (Table 1).

TABLE 1

Experimental Design

| Grp | Mouse # | Mouse strain | Inducing Agent | Dose (mg/kg) | Regimen |
|---|---|---|---|---|---|
| 1 | 1-4 | C57BL/6J | Control | NA | 3 × daily |
| 2 | 5-8 | Cyp3a cluster KO | Control | NA | 3 × daily |
| 3 | 9-12 | C57BL/6J | RIF | 60 | 3 × daily |
| 4 | 13-16 | Cyp3a cluster KO | RIF | 60 | 3 × daily |

Pathology
Hepatomegaly

There was small (~6%) but statistically significant increase in liver/body weights ratios in the vehicle treated Cyp3a cluster KO mice compared to the vehicle treated C57BL/6J mice which is unlikely to be biologically relevant. Rifampicin treatment did not result in any hepatomegaly in either mouse strain. (Table 2).

TABLE 2

Body and liver weights.

| Mouse line | Treatment | Body weight (g) | Liver weight (g) | Liver/Body weight Ratio × 100 |
|---|---|---|---|---|
| C57BL/6J | Control | 27 +/− 2 (100 +/− 7) | 1.2 +/− 0.13 (100 +/− 11) | 4.4 +/− 0.18 (100 +/− 4) |
| C57BL/6J | RIF | 26 +/− 2.2 (95 +/− 8) | 1.3 +/− 0.03 (105 +/− 3) | 5 +/− 0.5 (112 +/− 11) |
| Cyp3a cluster KO | Control | 27 +/− 3.4 (100 +/− 13) | 1.26 +/− 0.14 (100 +/− 11) | 4.7 +/− 0.1* (100 +/− 2) |
| Cyp3a cluster KO | RIF | 27 +/− 3 (102 +/− 11) | 1.26 +/− 0.13 (100 +/− 10) | 4.6 +/− 0.16 (98 +/− 3) |

Data are mean +/− SD (% mean of corresponding strain control +/− % SD); n = 4. All liver/body weight ratios were compared with an unpaired t test (two tailed P values); *Significantly different from vehicle treated C57BL/6J ($P < 0.05$).

Histopathology
Haematoxylin and Eosin Staining

Histopathological examination was performed on samples of kidney, liver and small intestine from all animals in all groups. A slight, centrilobular hepatocellular hypertrophy was noted in treated C57BL/6J mice. There was also evidence of a minimal centrilobular hypertrophy in the liver of Cyp3a cluster KO mice. This alteration was considered to be related to the treatment with the rifampicin. All other microscopic findings recorded in the liver did not distinguish significantly between treated mice and control mice. Any differences were regarded as random events, spontaneous in nature and within the normal background pathology commonly seen in mice (FIG. 1c). No microscopic findings related to the treatment with the rifampicin were recorded in the kidney or small intestine (FIG. 1d-1e). Under the conditions of this study, the repeated administration of 60 mg rifampicin per kg body weight for 3 days to mice of two different strains produced pathological evidence of a hepatocellular hypertrophy in both strains. The transgenic mice (Cyp3a cluster KO) appeared to be less severely affected.

Oil Red O Staining

Liver samples were investigated for lipid deposition by Oil Red O staining. There was no evidence of fat accumulation in the any of vehicle treated mouse livers (FIG. 1f). In livers from rifampicin treated C57BL/6J mice a moderate (grade 1) staining with droplet patterns of Oil Red O around nuclei was observed. This could not be detected in the liver sections from the rifampicin treated Cyp3a cluster KO mice.

Clinical Chemistry

Plasma samples from all animals were analysed for triglycerides, alanine transferase, alkaline phosphatase, aspartate aminotransferase, albumin, bilirubin (total and direct); creatine kinase, high density lipoprotein, low density lipoprotein and γ-glutamyltransferase. γ-glutamyltransferase activity and levels of direct bilirubin were below the limit of quantification. Values of all other plasma clinical chemistry parameters fell within the known normal range for untreated C57BL/6J mice (FIG. 1g)

Molecular/Biochemical Phenotype

Pharmacokinetics of Midazolam

Midazolam pharmacokinetics in wild type and Cyp3a cluster KO animals are presented on FIG. 1h.

Both mouse strains shown fast absorption of the substrate after IP administration. This was not influenced by prior administration of rifampicin for 3 days. The AUC for midazolam was similar in the wild type and Cyp3a cluster KO control animals (FIG. 1i). Treatment with rifampicin accelerated elimination of the substrate in both mouse strains, showing higher effect in the C57BL/6J mice. It has been demonstrated previously that the expression level of a metabolising cytochrome P450 in the liver is inversely proportional to the AUC of an isoformspecific substrate, if the substrate is administered intraperitoneally. Thus the AUC of midazolam was expected to be higher in the Cyp3a cluster KO mice due to deletion of the cluster of its main metabolising enzyme. However, this was not the case, which suggests involvement of some compensatory changes, perhaps similar to those described in the literature (van Waterschoot et al., 2008).

Cyp3a Protein Expression and Activity

Expression of Cyp3a in liver microsomes from the Cyp3a cluster KO mice decreased to a level below the detection limit by Western blotting in both treated and control animals (FIG. 1j). This correlated with a significant decrease in oxidation of the Cyp3a specific substrate 7-BQ compared to the corresponding experimental group of C57BL/6J mice (to 18% in control and to 6.7% in rifampicin treated). Midazolam 1'-hydroxylation, which is catalysed by both Cyp3a and Cyp2c isoforms, decreased to 53% and 18% in control and treated animals respectively. Decrease in midazolam 4-hydroxylation (to 65%) was small and not statistically significant for the Cyp3a cluster KO control group compared to control C57BL/6J. This was an unexpected result considering that 4-hydroxylation has been shown to be catalysed predominantly by mouse Cyp3a (Perl off et al., 2000). Midazolam 4-hydroxylation was decreased in the Cyp3a cluster KO rifampicin treated group to 23% compared to wild type mice.

Pre-treatment of Cyp3a cluster KO mice with rifampicin resulted in small (168%) but statistically significant (P<0.05) increase in 7-BQ oxidation. The effect of rifampicin on midazolam hydroxylation in Cyp3a cluster KO mice was even smaller (123% increase for 1'-hydroxylation and 112% for 4-hydroxylation) and not statistically significant.

Western blotting of the intestinal microsomes did not produce any Cyp3a band (data not shown).

Measurement of the specific activities of the intestinal microsomes resulted in highly inconsistent data, which are likely to reflect the inconsistencies in the preparation of the intestinal microsomes by scraping of the epithelial cells (Bonkovsky et al., 1985; Mohri and Uesawa, 2001) (data not shown).

The antibodies used in this study demonstrated a clear band on the Western blot after interaction with the major recombinant cytochrome P450 from the subfamilies tested. However the specificity of the antibodies to different isoform within one P450 subfamily was not investigated.

Cyp1a Protein Expression and Activity

Expression of Cyp1a was slightly higher in liver microsomes of Cyp3a cluster KO mice compared to wild type as determined by Western blotting (FIG. 1k). Rifampicin treatment resulted in small downregulation of Cyp1a in both mouse strains. Ethoxyresorufin de-ethylation activity (EROD) was similar in both Cyp3a cluster KO and wild type mouse liver microsomes. EROD is catalysed by both Cyp1a 1 and Cyp1a2 isoforms, with Cyp1a1 making the major contribution. Rifampicin treatment resulted in a small induction of EROD metabolism in both strains. There was no difference in methoxyresoryfin de-methylation (MROD) activity between wild type and Cyp3a cluster KO mice. MROD is catalysed predominantly by Cyp1a2.

Cyp2b Protein Expression and Activity

Expression of Cyp2b in mouse liver microsomes was low both for C57BL/6J and for Cyp3a cluster KO mice (FIG. 1l). Rifampicin treatment resulted in small induction of Cyp2b in both strains. This correlated with a small increase in PROD activity. Intestinal microsomes demonstrated markedly higher Cyp2b expression, which was not sensitive to rifampicin treatment. Liver microsomes from vehicle treated Cyp3a cluster KO mice demonstrated decreased benzoxyresorufin O-dealkylation (BROD) activity compared to the wild type. BROD was previously used as a substrate for murine Cyp2b (Donato et al., 2003). Rifampicin treatment resulted in BROD induction in both strains tested. These data suggest that enzymes from Cyp3a and, perhaps, Cyp2c isoforms may be involved in the BROD.

Cyp2c Protein Expression

Cyp2c protein expression in liver microsomes from C57BL/6J and Cyp3a cluster KO mice was estimated by Western blotting (FIG. 1m). The protein band intensity was slightly increased in the sample from control Cyp3a cluster KO mice compared to the wild type. Both animal strains demonstrated marked Cyp2c induction after treatment with rifampicin.

Cyp2d Protein Expression

Cyp2d protein bands were detected both in liver and in intestinal samples (FIG. 1n). There was no marked difference in the Cyp2d protein band intensity between liver samples from untreated wild type and Cyp3a cluster KO mice. Rifampicin treatment resulted in a small decrease in Cyp2d expression for the C57BL/6J mice and small increase for the Cyp3a cluster KO mice. There was a small increase in intestinal Cyp2d levels in Cyp3a cluster KO compared to wild type. Rifampicin treatment had no notable effect of the on level of Cyp2d in intestinal microsomes of either mouse strain.

Cyp2e Protein Expression

The Cyp2e protein band intensity was slightly higher in the liver microsomes of Cyp3a cluster KO mice compared to wild type (FIG. 1o). Rifampicin treatment did not result in a notable change in Cyp2e levels in liver microsomes of either mouse strain. Similarly, there was a higher level of Cyp2e expression in the intestine of Cyp3a cluster KO mice compared to wild type. Treatment with rifampicin resulted with a small induction of intestinal Cyp2e in Cyp3a cluster KO mice and a small down-regulation of intestinal Cyp2e in wild type mice.

Cyp4a Protein Expression

Cyp4a protein was detected in liver microsomes from both mouse strains (FIG. 1p). Cyp4a expression level in samples from wild type mice was markedly increased after the rifampicin treatment.

Mouse P450 Oxidoreductase (POR) Protein Expression

Cytochrome P450 oxidoreductase level was similar in liver microsomes from C57BL/6J and Cyp3a cluster KO mice (FIG. 1q). Both mouse strains responded to the rifampicin treatment by marked increase in the protein expression level of POR. Liver microsomes from rifampicin treated animals demonstrated slightly higher activity in reduction of cytochrome C compared to wild type animals. The increase was not statistically significant.

Total P450 Content

Cyp3a cluster KO mice demonstrated a small but statistically significant increase in total P-450 content in liver microsomes of vehicle treated animals compared to C57BL/6J mice (FIG. 1r). Rifampicin treatment resulted in marked increase in the total P450 for wild type mice. However the P450 content of Cyp3a cluster KO mouse liver microsomes remained unchanged.

Conclusions

Cyp3a cluster KO mice did not show any genotypically induced pathological changes in plasma, liver, kidney or small intestine. The model showed levels of Cyp3a expression below the limit of detection by Western blotting. There was a marked (to levels below 20% compared to the wild type mice) decrease in the activity towards Cyp3a specific substrate 7-BQ. In vitro data on midazolam clearance suggested that P450 from Cyp3a subfamily are not the only metabolising enzymes involved in the elimination of this substrate.

Midazolam hydroxylation activity of liver microsomes from untreated Cyp3a cluster KO mice was ~60% of that from the wild type strain. This could be explained by involvement of another P450, such as Cyp2c (Perloff et al., 2000; van Waterschoot et al., 2008) in its oxidation. Rifampicin treatment induced Cyp3a in wild type and not in Cyp3a cluster KO. This resulted in more pronounced (to 20% compared to wild type) difference in midazolam hydroxylation activity in the liver microsomes from treated Cyp3a cluster KO mice. Midazolam PK data provide additional proof of the involvement of multiple metabolising enzymes in midazolam elimination. There was no difference in midazolam PK between untreated Cyp3a cluster KO and C57BL/6J mice, which correlates with previously published data and could be attributed to some upregulation of P450 (e.g. from Cyp2c subfamily) in the Cyp3a cluster KO strain (van Waterschoot et al., 2008). Administration of rifampicin accelerated midazolam elimination in both mouse strains. This was indicative of induction of a metabolising enzyme, which was up to 470% and 270% in wild type and Cyp3a cluster KO mice respectively (estimations were made on the basis of changes in the AUC). Whilst liver microsomes from the induced C57BL/6J mice also showed high (up to 380%) increase in midazolam hydroxylation activity, those from the Cyp3a cluster KO strain demonstrated only a small (up to 125%) induction in midazolam hydroxylation. The difference in rifampicin effect on midazolam clearance in vitro and in vivo infers induction of an alternative pathway of midazolam elimination in vivo in Cyp3a cluster KO mice.

Further experiments have been performed comparing the PK profile of 1'-hydroxymidazolam, and enzymatic modification of other Cyp3a substrates The study consisted of 9 groups (Table 3). The mice received 3 daily intraperitoneal (1 p) doses of rifampicin (60 mg/kg). On day 4 of the study midazolam (1 mg/kg) was administered by IV injection to animals from groups 1-6 and orally (2 mg/kg) to mice from groups 7-9. Blood samples were collected at 2, 5, 10, 20, 30, 45, 60, 90, 120 and 150 min (serial bleeds) after IV dosing, at 10, 20, 40, 60, 90, 120, 240 and 360 min after the oral dosing, for PK analysis (Table 3).

TABLE 3

| Group | Mouse # | Mouse strain | Inducer treatment | Midazolam Administration | Terminal Blood |
|---|---|---|---|---|---|
| 1 | 1-3 | C57BL/6J | RIF (60 mg/kg, 3 daily doses) | IV (1 mg/kg, single dose) | 30 min |
| 2 | 4-6 | Cyp3a cluster KO | RIF (60 mg/kg) | IV (1 mg/kg, single dose) | 30 min |
| 3 | 7-9 | Cyp3a11 KO | RIF (60 mg/kg) | IV (1 mg/kg, single dose) | 30 min |
| 4 | 10-12 | C57BL/6J | RIF (60 mg/kg) | IV (1 mg/kg, single dose) | 150 min |
| 5 | 13-15 | Cyp3a cluster KO | RIF (60 mg/kg) | IV (1 mg/kg, single dose) | 150 min |
| 6 | 16-18 | Cyp3a11 KO | RIF (60 mg/kg) | IV (1 mg/kg, single dose) | 150 min |
| 7 | 19-21 | C57BL/6J | RIF (60 mg/kg) | PO (2 mg/kg, single dose) | 360 min |
| 8 | 22-24 | Cyp3a cluster KO | RIF (60 mg/kg) | PO (2 mg/kg, single dose) | 360 min |
| 9 | 25-27 | Cyp3a11 KO | RIF (60 mg/kg) | PO (2 mg/kg, single dose) | 360 min |

Pharmacokinetics of 1'-Hydroxymidazolam

Previously rifampicin treatment induced Cyp3a in wild type but not in Cyp3a cluster KO mice, which resulted in a marked difference in the in vitro midazolam hydroxylation activity between the two mouse strains. However the difference in midazolam elimination in vivo was less pronounced, suggesting induction of an alternative pathway of midazolam elimination in vivo in Cyp3a cluster KO mice. This study monitored the pharmacokinetics of 1'-hydroxymidazolam (the primary metabolite) following IV and oral doses of midazolam to rifampicin induced mice, as a more sensitive and specific method for the estimation of P450 expression levels. Total concentrations of 1'-hydroxymidazolam were measured following pre-treatment of blood with B-glucuronidase. The pharmacokinetics of the 1'-hydroxymidazolam after the IV injection of the parent compound are presented on FIG. 1s.

The terminal phase of the curve is similar for both C57BL|6J and Cyp3a11 KO mice suggesting very minor strain difference in the clearance of this metabolite. The terminal phase of the Cyp3a cluster KO mouse PK indicates slightly slower elimination of the 1'-hydroxymidazolam compared to other strains. The AUC for 1'-hydroxymidazolam was markedly (~3 times) decreased in the Cyp3a cluster KO mice compared to the wild type strain demonstrating that cytochromes P450 from Cyp3a subfamily is the major route for the formation of this metabolite. The decrease in AUC for the Cyp3a11 KO mouse was less pronounced (~2 times) suggesting some involvement of other members of the Cyp3a subfamily in 1'-hydroxymidazolam generation. The pharmacokinetics of 1'-hydroxymidazolam after the oral midazolam administration are presented on FIG. 1t.

The terminal phase of the curve was similar for all the strains. However there were differences in early absorption phase. Bioavailability was lower in Cyp3a cluster KO and Cyp3a11 KO mice compared to wild type animals. This indicates a major contribution of the intestinal cytochromes P450 to the formation of 1'-hydroxymidazolam after the oral administration of midazolam. This was supported by the IV data which showed that much higher difference in AUC of 1'-hydroxymidazolam between wild type and KO animals after the IV injection. The impact from Cyp3a enzymes in the C57BL/6J is likely to be underestimated in this study as there were very few data points defining the absorption phase of the curve.

Cyp3a Enzymatic Activities

The oxidation of Cyp3a specific substrates by liver and intestinal microsomes was tested using triazolam, nifedipine, testosterone, dibenzylfluorescein (DBF) and 7-benzyloxy-4-trifluoromethylcoumarin (BFC). Triazolam, nifedipine and testosterone were assigned to the different substrate groups within CYP3A4 based on a statistical analysis of interaction of 10 CYP3A4 substrates with different CYP3A4 ligands (Kenworthy et al., 1999). DBF and BFC produce fluorescent metabolites and have found wide application in highthroughput screens for CYP3A4 inhibitors. Another fluorescent substrate, 7-benzyloxyquinoline (BQ), has shown good specificity to Cyp3a.

In all relevant graphs activities of samples from small intestine should be read using right Y axis scale, whereas activities of liver microsomes should be read using left Y axis scale.

Triazolam α-Hydroxylation

Results for the oxidation of triazolam by liver and intestinal microsomes are shown on FIG. 1$u$. There was a pronounced decrease in triazolam hydroxylation in both Cyp3a cluster KO and Cyp3a11 KO mice. This correlated well with the published data (Perloff et al., 2000), were triazolam was demonstrated to be a highly specific substrate for the mouse cytochromes P450 from Cyp3a subfamily. The data also indicated a major contribution from Cyp3a11 to the hydroxylation and a negligible impact from other Cyp3a enzymes, as activities of Cyp3a cluster KO and Cyp3a11 KO were extremely low and not statistically different.

Nifedipine Oxidation

There was a significant (P<0.001) decrease nifedipine oxidation by liver microsomes from Cyp3a cluster KO and Cyp3a11 KO mice compared to wild type mice (FIG. 1$v$). The decrease was less pronounced than that for triazolam, indicating possible involvement of enzymes from different subfamilies. Although mean values for the Cyp3a cluster KO and Cyp3a11 KO were different, the difference was not statistically significant. There was no statistically significant difference in the nifedipine oxidation by intestinal microsomes.

Testosterone Hydroxylation

Testosterone is hydroxylated by several different cytochromes P450. 6p-hydroxylation is usually attributed to the enzymes from Cyp3a subfamily, whilst 16β-hydroxylation is catalysed by Cyp2b10 and Cyp2c29 (Honkakoski et al., 1992). An up-regulation of enzymes from the Cyp2c subfamily in Cyp3a cluster knock-out mice has been reported previously (van Waterschoot et al., 2008). Therefore both hydroxylations were investigated using liver and intestinal microsomes (FIG. 1$w$-1$x$).

There was a significant decrease in 6β-hydroxylation of testosterone both in Cyp3a cluster KO and in Cyp3a11 KO mice. There was no difference in the formation of 6β-testostetone by liver microsomes from the transgenic mouse strains. Activity of the intestinal microsomes from Cyp3a cluster KO mice was lower than that from Cyp3a11 KO mice (P<0.05), which could indicate of involvement of other Cyp3a enzymes in testosterone 6β-hydroxylation by mouse small intestine. 16β-Hydroxylation of testosterone increased in liver microsomes of both transgenic strains compared to wild type mice suggesting some compensatory changes, which are likely to be over-expression of enzymes from Cyp2c subfamily (van Waterschoot et al., 2008). Although the mean value for Cyp3a cluster KO was higher than that for Cyp3a11 KO, the difference was not statistically significant.

Oxidation of DBF

Results for the oxidation of DBF are shown on FIG. 1$y$. DBF oxidation by liver microsomes demonstrated a pronounced decrease in samples from both Cyp3a cluster KO and Cyp3a11 KO mice. The difference between the two knock-out strains was not statistically significant, suggesting Cyp3a11 to be the main metabolising enzyme. There was no statistically significant difference between the wild type and knockout strains in DBF oxidation by intestinal microsomes.

Oxidation of BFC

Results for the oxidation of BFC are shown on FIG. 1$z$.

There was no difference in BFC activity between liver microsomal samples. In intestinal microsomes a small but statistically significant increase was observed, suggesting upregulation of cytochromes P450 from other subfamilies in the transgenic mice, which oxidise BFC.

Conclusions

The Cyp3a cluster KO model previously demonstrated substrate-specific behaviour. Clear differences between the model and wild type mice were observed for 7-BQ oxidation. However no difference was detected for midazolam hydroxylation, suggesting the involvement of other P450 such as Cyp2c (Perloff et al., 2000; van Waterschoot et al., 2008) in the reaction, Rifampicin treatment induced Cyp3a in wild type and not in Cyp3a cluster KO. This resulted in a marked decrease in midazolam hydroxylation activity in the liver microsomes from treated Cyp3a cluster KO mice. The difference in vivo was less pronounced, as indicated by midazolam AUC, suggesting induction of an alternative pathway of midazolam elimination in Cyp3a cluster KO mice. This inferred that the pharmacokinetics of midazolam metabolites may provide more specific and sensitive estimation of Cyp3a expression level.

The AUC for 1'-hydroxymidazolarn after the IV dosing of the parent compound markedly (~3 times) decreased in Cyp3a cluster KO mice demonstrating a major contribution from Cyp3a subfamily to the formation of this metabolite. The method was an improvement to that used previously, which was based on the measurement of midazolam AUC (1.6 times). However it did not completely correspond to the differences observed in vitro (6 times). This difference may be explained by the complex dependencies of the metabolite AUC from clearance and volume of distribution of both parent and metabolite itself (Rowland and Tozer, 1995). There are other complicating factors following oral administration of the parent drug, when gut metabolism and absorption are involved in the disposition of the metabolite. Difference in substrate oxidations between mouse strains corresponded well between liver and intestinal microsomes for testosterone and triazolam. However the pattern was different for the oxidation of nifedipine, DBF and BFC. This may indicate involvement of different enzymes in the latter reactions and different relative concentration of those enzymes in the liver and small intestine. This suggested the metabolite AUC after the oral administration to be less informative than that one after the IV injection in the estimation of the expression level of cytochromes P450. The Cyp3a substrates used in this study could be ranked in order of the impact of the Cyp3a subfamily in their oxidation:

triazolam>DBF:testosterone>nifedipine>>BFC.

Data on the oxidation of CYP3A4 substrate BFC indicates low specificity of the compound to mouse cytochromes P450 from Cyp3a subfamily. This is consistent with previously reported differences in oxidation of BFC between human and rat cytochromes P450 (Stresser et al., 2002)

The effect of the Cyp3a cluster knockout has also been assessed at a transcriptional level using whole genome microarrays and RNA prepared from the liver. Agilent Whole Mouse Genome Oligo Microarray slides (G4122-60510) and Agilent 44K gasket slides G2534-60005 were used for the study.

Animals were administered rifampicin/corn oil at 60 mg/kg/3 days or the vehicle alone, by intraperitoneal injection, as indicated in Table 1. Fold changes in gene expression are displayed in Table 4.

TABLE 4

Comparison of gene expression changes in untreated Cyp3a cluster KO mice vs. untreated WT mice (1), Cyp3a cluster KO mice vs. WT mice after treatment with rifampicin (2) and untreated WT mice vs. rifampicin-treated WT mice (3) signature gene lists.

| GenBank | Name | 3a KO vs WT Fold Change | 3aKO rif vs WR rif Fold Change | WT rif vs WT Fold change |
|---|---|---|---|---|
| Cytochrome P450s | | | | |
| NM_009997 | Cyp2a4 | 2.8 | 3.4 | 2.2 |
| | Cyp2b1 | | | |
| | Cyp2b13 | | 5.5 | |
| | Cyp2b10 | | 7.2 | −3.8 |
| | Cyp2b9 | | 3.2 | |
| NM_028089 | Cyp2c39 | 4.7 | | |
| | Cyp2c37 | | 1.9 | |
| | Cyp2c38 | | | |
| | Cyp2c44 | | | |
| | Cyp2c50 | | | |
| | Cyp2c54 | | 2.7 | |
| | Cyp2c68 | | | |
| | Cyp2c70 | | | |
| | Cyp2c66 | | | |
| | Cyp2c29 | | 1.5 | |
| NM_017396 | Cyp3a11 | −100 | −96.2 | 3.2 |
| NM_019792 | Cyp3a25 | −100 | −85.7 | |
| NM_007819 | Cyp3a13 | −1.4 | | |
| NM_007820 | Cyp3a16 | −100 | −92.6 | 2.7 |
| X71478 | Cyp4a10 | 2 | 1.3 | |
| NM_007822 | Cyp4a13 | −14.9 | | |
| | Cyp4a2b | | 3.3 | |
| Glutathione transferases | | | | |
| | GSTA3 | | −1.7 | |
| | GSTA4 | | −1.3 | |
| NM_008181 | GSTA5 | −2.1 | −2.8 | 3.6 |
| | GSTK1 | | | |
| NM_013541 | GSTP1 | 2.4 | 2.6 | −2.2 |
| | GSTT1 | | | |
| | GSTZ1 | | 1.8 | |
| NM_019946 | MGST1 | 1.4 | 2.7 | |
| | MGST2 | | | |
| AK008211 | MGST3 | −2.3 | −2.4 | |
| UDP-Glucorosyl-transferases | | | | |
| | UGT1A3 | | | |
| | UGT1A4 | | | |
| | UGT1A6 | | −1.5 | |
| | UGT2A1 | | | |
| NM_152811 | UGT2B17 | 2.9 | | |
| | UGT2B4 | | | |
| | UGT2B7 | | | |
| Sulphotransferases | | | | |
| | SULT1A1 | | | |
| | SULT1C2 | | −2.1 | |
| | SULT1C3 | | | |
| | SULT1E1 | | | |
| | SULT2A1 | | | |
| | AANAT | | | |
| Drug transporters | | | | |
| | ABCA1 | | | |
| | ABCA12 | | | |
| | ABCA13 | | | |
| | ABCA2 | | | |
| | ABCA3 | | 1.8 | |
| | ABCA4 | | | |
| | ABCA5 | | | |
| AK040652 | ABCA6 | −1.8 | −2.1 | |
| | ABCA7 | | | |
| NM_019552 | ABCA8A | 1.4 | 1.3 | |
| | ABCA9 | | | |
| NM_008830 | ABCB1 | | | |
| | ABCB10 | 2.2 | | |
| | ABCB11 | | −1.5 | 2 |
| | ABCB4 | −1.4 | −1.5 | |
| | ABCB5 | | | |
| | ABCB6 | | | |
| | ABCB7 | | | |
| | ABCB8 | | | |
| | ABCB9 | | −1.6 | |
| | ABCC1 | | | |
| | ABCC10 | | | |
| | ABCC12 | | | |
| | ABCC2 | | 1.4 | |
| | ABCC3 | | | |
| | ABCC4 | | | |
| | ABCC5 | | | |
| | ABCC6 | | | |
| | ABCC8 | | | |
| | ABCC9 | | | |
| | ABCD1 | | 2.7 | |
| | ABCD2 | | | |
| BC009119 | ABCD3 | −1.5 | 3.5 | −3.5 |
| | ABCD4 | | 1.8 | |
| | ABCE1 | | 1.5 | |
| NM_013854 | ABCF1 | 1.7 | 1.5 | |
| NM_013853 | ABCF2 | 1.6 | | |
| NM_013852 | ABCF3 | 1.6 | | |
| | ABCG1 | | | |
| | ABCG2 | | 1.8 | |
| | ABCG4 | | | |
| NM_031884 | ABCG5 | −1.5 | −1.6 | |
| | ABCG8 | | 2.7 | |
| Miscellaneous | | | | |
| NM_134072 | AKR1C14 | 2.1 | 2.7 | |
| NM_007520 | BACH1 | −2.1 | | |
| NM_007595 | CAMK2B | 2.6 | 3.7 | |
| | CFTR | | | |
| NM_010828 | CITED2 | 2.2 | 2.8 | −3.4 |
| | COMT | | | |
| NM_013888 | DNAJC12 | −4.1 | | |
| | EPHX1 | | 1.8 | |
| NM010232 | FMO5 | 3 | 4.7 | |
| | GLYAT | | | |
| M77015 | HSD3B3 | 3 | 4.9 | |
| NM_010591 | JUN | −4.1 | | |
| NM_008416 | JUNB | −5.1 | −3 | |
| NM_011943 | MAP2K6 | 3.3 | 3.6 | |
| NM_011945 | MAP3K1 | −2.3 | −2.7 | |
| NM_011947 | MAP3K3 | 2.8 | | |
| NM_013634 | MED1 | −2 | | |
| | NAT1 | | | |
| | MRI2 | | 1.7 | |
| NM_016737 | STIP1 | 2.3 | | |
| | TAP1 | | | |
| | TAP2 | | | |

Genes were grouped according to phase I and phase II xenobiotic metabolizing enzymes and phase III drug transporters. The column shows Genbank Accession numbers, primary sequence name, and fold change. Positive numbers = Up-regulated genes. Negative numbers = Down-regulated genes. Blank boxes indicate the gene was not altered by the treatment relative to WT mice.

Example 2

Cyp2c Cluster Exchange

The 5' end of the mouse Cyp2c cluster was targeted by homologous recombination, so that a wildtype loxP and a f3 site are inserted downstream of Exon 1 of the Cyp2c55 gene. A 5' deficient neomycin resistance and a TK expression cassette were co-introduced as depicted in FIG. 2a. The translational start ATG is separated in frame from the 5' deficient neomycin resistance cassette by the loxP site, so that additional amino acids encoded by the loxP site are attached to the N-terminus of neomycin protein.

Correctly targeted ES cells were further modified by a subsequent step of homologous recombination at the 3' end of the mouse Cyp2c cluster, so that a frt, lox5171 and wildtype loxP site are inserted downstream of Exon5 of the Cyp2c70 gene as depicted in FIG. 2b. Furthermore, a hygromycin resistance and a thymidine kinase (TK) expression cassette were co-introduced as depicted.

To allow the deletion of the mouse Cyp2c cluster by Cre-mediated recombination, the targeting at both ends of the cluster has to be on the same allele. This was tested in vitro by transfection of double targeted ES cells with Cre and subsequent selection with ganciclovir. Only in cells with targeting on the same allele are the TK genes at both ends of the cluster deleted as depicted in FIG. 2c, so that the TK-mediated conversion of the nucleoside analog ganciclovir to a toxic triphospate analog is prevented. Therefore, only ES cells with targeting on the same allele survive the ganciclovir selection. Surviving ES cell clones were further analysed by PCR to confirm that the mouse Cyp2c cluster was deleted and PCR-positive clones were injected into blastocysts to generate chimeric mice. By subsequent crosses mice with a homozygous deletion of the Cyp2c cluster were generated.

The remaining wildtype loxP and the lox5171 sites in the ES cells can be used subsequently to insert replacement genes, e.g. the human CYP2C cluster, at the former position of the mouse cluster by Cre-mediated insertion. The remaining promoter, the ATG and in frame wildtype loxP site can be utilized to insert again a 5' deficient selection cassette, e.g. 5' deficient neomycin, to select for clones with correct insertion with high efficiency. The frt and f3 sites at both ends can be used to delete the selection cassettes introduced with the replacement genes by Flp-mediated deletion, provided that additional frt and f3 sites are co-introduced in the right orientation with the replacement cassette. PCR proof of the generation of this homozygous cluster KO is shown in FIG. 2d.

Example 3

Homozygous Cyp3a Cluster Knock-Out/Cyp2c Cluster Knock-Out Mice

A viable mouse (ID 234254) has been bred through crossing Cyp3a and Cyp2c KO mice together. This mouse carries a homozygous deletion of both the mouse Cyp3a cluster (7 genes deleted) and Cyp2c cluster (14 genes deleted).

FIG. 2e shows PCR confirmation of the absence of the mouse Cyp3a cluster from the genome in mouse ID 234254. FIG. 2f shows PCR confirmation of the absence of mouse Cyp2c cluster from the genome of the same animal.

The homozygous Cyp3a cluster KO/Cyp2c cluster KO mice will be characterised in terms of their histopathology, biochemistry, protein expression and mRNA transcript levels, as detailed in example 1. Additionally, further characterisation of the strain employing known and hypothetical Cyp2c P450 isoform substrates shall be performed.

Example 4

Cyp2d Cluster Deletion

The 3' end of the mouse Cyp2d cluster was targeted by homologous recombination, so that a frt, lox5171 and wildtype loxP site are inserted downstream of Exon1 of the Cyp2d26 gene as depicted in FIG. 3a. Furthermore, a hygromycin resistance cassette was co-introduced as depicted. As the subsequent deletion of the mouse cluster will leave behind an intact Cyp2d26 promoter and exon1 of the Cyp2d26 gene, which might interfere with the expression of human CYP2D6 to be inserted at the 5' end of the cluster as described below, a splice acceptor polyadenylation motif (sApA) was included into the 3' targeting vector, which terminates the expression from the Cyp2d26 promoter.

Correctly targeted ES cells were further modified by a subsequent step of homologous recombination at the 5' end of the mouse Cyp2d cluster, so that a human CYP2D6 expression cassette flanked by an frt and a wildtype loxP site and a neomycin resistance cassette 3' to the loxP site are inserted downstream of Exon3 of the Cyp2d22 gene as depicted in FIG. 3b.

Deletion of the mouse Cyp2d cluster while maintaining the human expression cassette can be achieved by Cre-mediated recombination at the loxP sites and simultaneous deletion of the mouse cluster and the human expression cassette, resulting in a complete knockout of the Cyp2d locus (as depicted in FIG. 3c), is the result of Flp-mediated recombination at the frt sites.

To allow the deletion of the mouse Cyp2d cluster by Cre- or Flp-mediated recombination, the targeting at both ends of the cluster has to be on the same allele. Therefore, double targeted ES clones were further analyzed by in vitro deletion with Cre, followed by a PCR analysis with a primer pair that allows the detection of the deletion of the cluster. PCR analysis was performed on a pool of deleted and undeleted clones, as in vitro Cre-deletion occurs only in a fraction of transfected cells and there is no possibility to select for individual cells in which the deletion was successful. PCR-positive undeleted parental clones were injected into blastocysts to generate chimeric mice. By crosses with either Cre- or Flp-deleter strains or strains with tissue specific expression of the respective recombinase and subsequent intercrosses homozygous Cyp2d cluster deleted mice either with deletion in the whole body or in specific tissues and that contain or do not contain a human expression cassette will be generated.

PCR proof of the generation of this homozygous cluster KO is shown in FIG. 3d.

Bufuralol PK in Cyp2d KO Mice

The pharmacokinetics of Cyp2d specific substrate bufuralol was investigated in the Cyp2d KO mice (mice which are nulled of all Cyp2d isoforms). Wild type, C57BL/6J mice were used as a control. It was shown that AUC of bufuralol was markedly increased in Cyp2d KO mice when compared to the wild type (FIG. 3e). This correlated well with the in vitro data (Bogaards et al., 2000), where the rate of bufuralol hydroxylation was demonstrated to be ~10 times higher in mouse liver microsomes compared to human liver microsomes.

REFERENCES

Anderson, S. P., Dunn, C., Laughter, A., Yoon, L., Swanson, C., Stulnig, T. M., Steffensen, K. R., Chandraratna, R. A., Gustafsson, J. A., and Corton, J. C. (2004). Overlapping transcriptional programs regulated by the nuclear receptors peroxisome proliferator-activated receptor alpha, retinoid X receptor, and liver X receptor in mouse liver. *Mol Pharmacol* 66, 1440-52.

Bogaards J J, Bertrand M, Jackson P, Oudshoorn M J, Weaver R J, van Bladeren P J and Walther B (2000) Determining the best animal model for human cytochrome P450 activities: a comparison of mouse, rat, rabbit, dog, micropig, monkey and Bonkovsky H L, Hauri H P, Marti U, Gasser R and Meyer U A (1985) Cytochrome P450 of small intestinal epithelial cells. Immunochemical characterization of the increase in cytochrome P450 caused by phenobarbital. *Gastroenterology* 88:458-467.

Donato M T, Klocke R, Castell J V, Stenzel K, Paul D and Gomez-Lechon M J (2003) Constitutive and inducible expression of CYP enzymes in immortal hepatocytes derived from SV40 transgenic mice. *Xenobiotica* 33:459-473

Honkakoski, P, Auriola S and Lang M A (1992) Distinct induction profiles of three phenobarbital-responsive mouse liver cytochrome P450 isozymes. *Biochem Pharmacol* 43:2121-2128.

Kenworthy K E, Bloomer J C, Clark S E and Houston J B (1999) CYP3A4 drug interactions: correlation of 10 in vitro probe substrates. *Br J Clin Pharmacol* 48:716-727.

Ide, T., Shimano, H., Yoshikawa, T., Yahagi, N., Amemiya-Kudo, M., Matsuzaka, T., Nakakuki, M., Yatoh, S., Iizuka, Y., Tomita, S., Ohashi, K., Takahashi, A., Sone, H., Gotoda, T., Osuga, J., Ishibashi, S., and Yamada, N. (2003). Crosstalk between peroxisome proliferator-activated receptor (PPAR) alpha and liver X receptor (LXR) in nutritional regulation of fatty acid metabolism. II. LXRs suppress lipid degradation gene promoters through inhibition of PPAR signaling. *Mol Endocrinol* 17, 1255-67.

Inc, A. t. (2007). Agilent Feature Extraction Software v9.5 User Guide. *Agilent Publication number g4460-90005*, 1-250.

Mohri K and Uesawa Y (2001) Enzymatic activities in the microsomes prepared from rat small intestinal epithelial cells by differential procedures. *Pharm Res* 18:1232-1236.

Perloff M D, von Moltke L L, Court M H, Kotegawa T, Shader R I and Greenblatt D J (2000) Midazolam and triazolam biotransformation in mouse and human liver microsomes: relative contribution of CYP3A and CYP2C isoforms. *J Pharmacol Exp Ther* 292:618-628.

Rowland M and Tozer N (1995) *Clinical Pharmacokinetics: Concepts and Applications*. Lippincot Williams & Wilkins, Philadelphia, US.

Saini, S. P., Sonoda, J., Xu, L., Toma, D., Uppal, H., Mu, Y., Ren, S., Moore, D. D., Evans, R. M., and Xie, W. (2004). A novel constitutive androstane receptor-mediated and CYP3A-independent pathway of bile acid detoxification. *Mol Pharmacol* 65, 292-300.

Stresser D M, Turner S D, Blanchard A P, Miller V P and Crespi C L (2002). Cytochrome P450 fluorimetric substrates: identification of isoform-selective probes for rat CYP2D2 and human CYP3A4. *Drug Metab Dispos* 30:845-852.

van Waterschoot, R. A., van Herwaarden, A. E., Lagas, J. S., Sparidans, R. W., Wagenaar, E., van der Kruijssen, C. M., Goldstein, J. A., Zeldin, D. C., Beijnen, J. H., and Schinkel, A. H. (2007). Midazolam metabolism in Cytochrome P450 3A knockout mice can be attributed to upregulated CYP2C enzymes. *Mol. Pharmacol.* 73, 1029-36.

Weng, L., Dai, H., Zhan, Y., He, Y., Stepaniants, S. B., and Bassett, D. E. (2006). Rosetta error model for gene expression analysis. *Bioinformatics* 22, 1111-21.

Xu, C., Li, C. Y., and Kong, A. N. (2005). Induction of phase I, II and III drug metabolism/transport by xenobiotics. *Arch Pharm Res* 28, 249-68.

Zhou, J., Zhang, J., and Xie, W. (2005). Xenobiotic nuclear receptor-mediated regulation of UDP-glucuronosyl-transferases. *Curr Drug Metab.* 6, 289-98.

The invention claimed is:

1. A transgenic mouse whose genome comprises a homozygous disruption of a Cyp3a gene cluster, wherein the mouse does not have Cyp3a activity and does not contain a gene from the human gene cluster.

2. The mouse according to claim 1, wherein the disruption is a deletion of the entire Cyp3a gene cluster.

3. The mouse according to claim 2, wherein the deletion is made by homologous recombination.

* * * * *